(12) United States Patent
Pourquie et al.

(10) Patent No.: US 10,240,123 B2
(45) Date of Patent: Mar. 26, 2019

(54) METHOD FOR PREPARING INDUCED PARAXIAL MESODERM PROGENITOR (IPAM) CELLS AND THEIR USE

(75) Inventors: Olivier Pourquie, Illkrich (FR); Jérôme Chal, Illkrich (FR)

(73) Assignees: INSERM (INSTITUT NATIONAL DE LA SANTE ET DE LA RECHERCHE MEDICALE), Paris (FR); CNRS (CENTRE NATIONAL DE LA RECHERCHE SCIENTIFIQUE), Paris (FR); UNIVERSITE DE STRASBOURG, Strasbourg (FR); ASSOCIATION FRANCAISE CONTRE LE MYOPATHIES, Paris (FR)

( * ) Notice: Subject to any disclaimer, the term of this patent is extended or adjusted under 35 U.S.C. 154(b) by 271 days.

(21) Appl. No.: 14/342,251

(22) PCT Filed: Aug. 29, 2012

(86) PCT No.: PCT/EP2012/066793
§ 371 (c)(1),
(2), (4) Date: Jul. 31, 2014

(87) PCT Pub. No.: WO2013/030243
PCT Pub. Date: Mar. 7, 2013

(65) Prior Publication Data
US 2014/0363886 A1    Dec. 11, 2014

Related U.S. Application Data

(60) Provisional application No. 61/654,120, filed on Jun. 1, 2012, provisional application No. 61/528,348, filed on Aug. 29, 2011.

(30) Foreign Application Priority Data

Aug. 29, 2011  (EP) .................................... 11306080
Jun. 1, 2012   (EP) .................................... 12305610

(51) Int. Cl.
*C12N 5/071*     (2010.01)
*C12N 5/0735*    (2010.01)
(Continued)

(52) U.S. Cl.
CPC ......... *C12N 5/0606* (2013.01); *C12N 5/0625* (2013.01); *C12N 5/0653* (2013.01);
(Continued)

(58) Field of Classification Search
CPC .. C12N 5/0606; C12N 5/0625; C12N 5/0653; C12N 5/0654; C12N 5/0658;
(Continued)

(56) References Cited

U.S. PATENT DOCUMENTS

2008/0038820 A1    2/2008  Rudy-Reil

FOREIGN PATENT DOCUMENTS

WO    2009/055396 A1    4/2009
WO    2010/008100 A1    1/2010
(Continued)

OTHER PUBLICATIONS

Sakurai et al., Stem Cell Res., 3: 157-169, 2009.*
(Continued)

*Primary Examiner* — Thaian N Ton
(74) *Attorney, Agent, or Firm* — Polsinelli PC; Christopher M. Cabral

(57) ABSTRACT

The present invention relates to an ex vivo method for preparing induced paraxial mesoderm progenitor (iPAM) cells, said method comprising the step of culturing pluripotent cells in an appropriate culture medium comprising an effective amount of an activator of the Wnt signaling pathway and an effective amount of an inhibitor of the Bone Morphogenetic Protein (BMP) signaling pathway.

Figure 2:
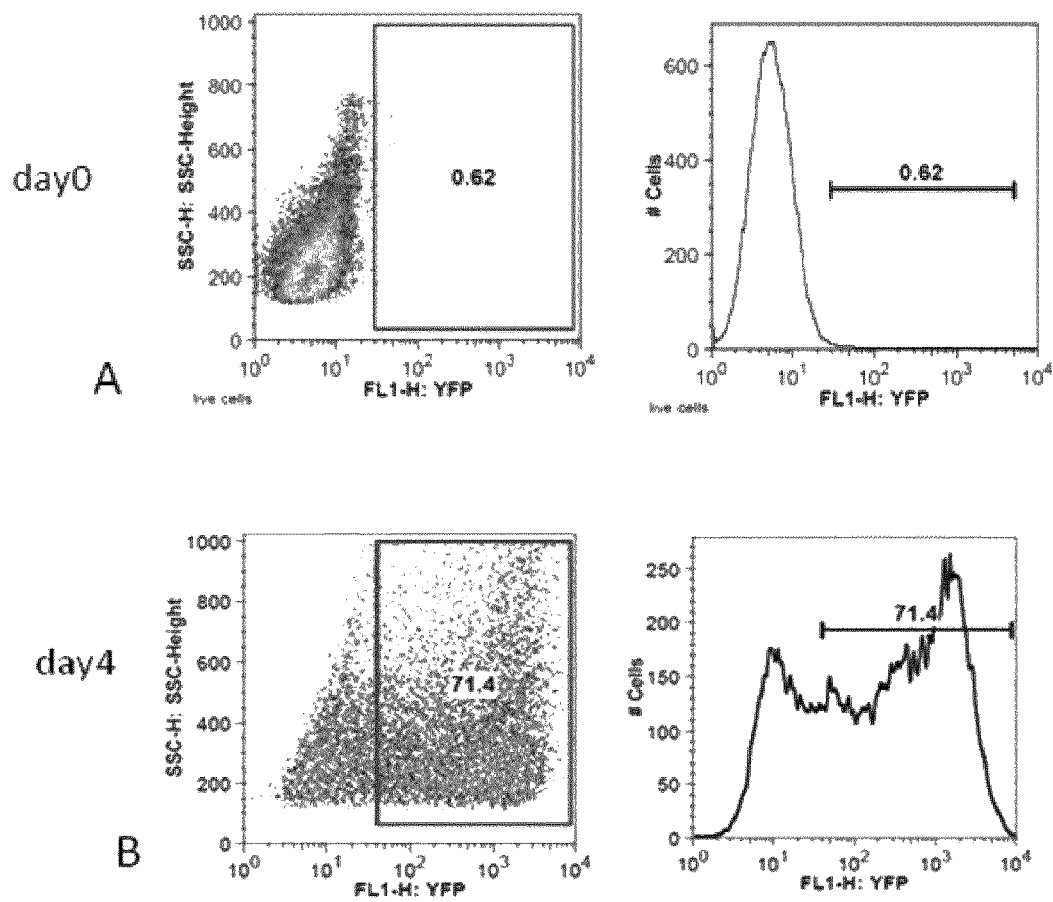

16 Claims, 19 Drawing Sheets
Specification includes a Sequence Listing.

(51) Int. Cl.
C12N 5/0775 (2010.01)
C12N 5/077 (2010.01)
(52) U.S. Cl.
CPC ......... *C12N 5/0654* (2013.01); *C12N 5/0658* (2013.01); *C12N 5/0662* (2013.01); *C12N 2500/62* (2013.01); *C12N 2501/155* (2013.01); *C12N 2501/40* (2013.01); *C12N 2501/415* (2013.01); *C12N 2501/727* (2013.01); *C12N 2506/02* (2013.01)
(58) Field of Classification Search
CPC .............. C12N 5/0662; C12N 2500/62; C12N 2501/155; C12N 2501/40; C12N 2501/415; C12N 2501/727; C12N 2506/02
See application file for complete search history.

(56) References Cited

FOREIGN PATENT DOCUMENTS

| WO | 2011/004911 A1 | 1/2011 |
|---|---|---|
| WO | WO 2011/025179 | 3/2011 |
| WO | 2016/009196 A1 | 1/2016 |
| WO | 2016/141084 A1 | 9/2016 |

OTHER PUBLICATIONS

"Muscle" from Encyclopaedia Britannica, accessed Jan. 19, 2017, published Feb. 1, 2012 at https://www.britannica.com/science/muscle, pp. 1-9.*
Rostovskaya et al., Phil. Trans. R. Soc. B, 370: 1-11, 2015.*
International Search Report (PCT/ISA/210) dated Nov. 9, 2012, by the European Patent Office as the International Searching Authority for International Application No. PCT/EP2012/066793.
Bakre, M., et al., "Generation of Multipotential Mesendodermal Progenitors from Mouse Embryonic Stem Cells via Sustained Wnt Pathway Activation," JBC, vol. 282, No. 43, pp. 31703-31712 (Oct. 26, 2007).
Barberi, T., et al., "Derivation of Engraftable Skeletal Myoblasts From Human Embryonic Stem Cells," Nature Medicine, vol. 13, No. 5, pp. 642-648 (May 2007).
Brevini, T., et al., "Embryonic Stem Cells in Domestic Animals No Shortcuts to Pig Embryonic Stem Cells," Theriogenology, vol. 74, pp. 544-550 (Apr. 18, 2010).
Brittan, M., et al., Gastrointestinal Stem Cells, J. of Path., vol. 197, pp. 492-509 (Jun. 3, 2002).
Cao, S., et al., "Isolation and Culture of Primary Bovine Embryonic Stem Cell Colonies by a Novel Method," J. of Exp. Zoo, vol. 311A, pp. 368-376 (Apr. 1, 2009).
Carmon, K., et al., "R-Spondins Function as Ligands of the Orphan Receptors Lgr4 and Lgr5 to Regulate Wnt/Beta-Catenin Signalling," PNAS, vol. 108, No. 28, pp. 11452-11457 (Jul. 12, 2011).
Chal, J., et al., "Differentiation of Pluripotent Stem Cells to Muscle Fiber to Model Duchenne Muscular Dystrophy," Nature Biotechnology, vol. 33, No. 9, pp. 1-11, doi: 10.1038/nbt.3297, Advance on-line publication (Aug. 3, 2015).
Chal, J., et al., "Differentiation of Pluripotent Stem Cells to Muscle Fiber to Model Duchenne Muscular Dystrophy," Nature Biotechnology, vol. 33, No. 9, pp. 1-11, doi: 10.1038/nbt.3297, Supplementary Information (Aug. 3, 2015).
Chal, J., et al., "Patterning and Differentiation of the Vertebrate Spine," The Skeletal System, Chapter 3, Cold Spring Harbor Laboratory Press, pp. 41-116, (2009).
Chalamalasetty, R., et al. "The Wnt3a/β-catenin target gene Mesogenin1 controls the segmentation clock by activating a Notch signalling program," Nature Communications, vol. 2, No. 390, doi:10.1038/ncomms1381 (Jul. 12, 2011).

Chamberlain, G., et. al., "Concise Review: Mesenchymal Stem Cells: Their Phenotype, Differentiation Capacity, Immunological Features, and Potential for Homing," Stem Cells, vol. 25, pp. 2739-2749 (Jul. 17, 2007).
Chambers, I., "The Molecular Basis of Pluripotency in Mouse Embryonic Stem Cells," Cloning Stem Cells, vol. 6, Issue. 4, pp. 386-391 (Dec. 16, 2004).
Chapman, D. L., et al. "Tbx6, a Mouse T-Box Gene Implicated in Paraxial Mesoderm Formation at Gastrulation," Dev Biol, vol. 180, Article No. 0326, pp. 534-542 (Jul. 23, 1996).
Clevers, H., "Wnt/beta-catenin Signaling in Development and Disease," Cell, vol. 127, pp. 469-480 (Nov. 3, 2006).
Cohen, P., et al., "GSK3 Inhibitors: Development and Therapeutic Potential," Nat Rev Drug Discov., vol. 3, pp. 479-487 (Jun. 2004).
Constam, D., et al., "Tissue-Specific Requirements for the Proprotein Convertase Furin/SPC1 During Embryonic Turning and Heart Looping", Development, vol. 127, pp. 245-254 (Jan. 15, 2000).
Cuny, G., et al., "Structure—Activity Relationship Study of Bone Morphogenetic Protein (Bmp) Signaling Inhibitors," Bioorganic & Medicinal Chemistry Letters, vol. 18, pp. 4388-4392 (Jun. 27, 2008).
Darabi, R., et al., "Assessment of the Myogenic Stem Cell Compartment Following Transplantation of Pax3/Pax7-Induced Embryonic Stem Cell-Derived Progenitors," Stem Cells, vol. 29, No. 5, pp. 777-790 (May 2011).
Darabi, R., et al., "Functional Skeletal Muscle Regeneration From Differentiating Embryonic Stem Cells," Nat Med, vol. 14, pp. 134-143 (Feb. 2008).
Davidson, K., et al., "Wnt/β-Catenin Signaling Promotes Differentiation, Not Self-Renewal, of Human Embryonic Stem Cells and Is Repressed by Oct4." PNAS, vol. 109, No. 12, pp. 4485-4490 (Mar. 20, 2012).
De Lau, W., et al. "The R-spondin protein family," Genome Biology, vol. 13, No. 242, pp. 1-10 (Mar. 22, 2012).
De Lau, W., et al., "Lgr5 Homologues Associate With Wnt Receptors and Mediate R-Spondin Signalling," Nature, vol. 476, pp. 293-298 (Aug. 18, 2011).
Dekel, I., et al., "Conditional Conversion of Es Cells to Skeletal Muscle by an Exogenous MyoD1 Gene," New Biol, vol. 4, pp. 217-224 (Mar. 1992).
Derynck, R., et al., "TGF-β and the TGF-β Family," The TGF-β Family, Chapter 2, Cold Spring Harbor Laboratory Press pp. 29-43 (2008).
Dimos, J., "Induced Pluripotent Stem Cells Generated From Patients With Als Can Be Differentiated Into Motor Neurons," Science, vol. 321, pp. 1218-1221 (Mar. 25, 2011).
Dinsmore, J., et al., "Embryonic Stem Cells Differentiated In Vitro as a Novel Source of Cells for Transplantation" Cell Transplant, vol. 5, pp. 131-143 (Mar.-Apr. 1996).
Fukada, S., et al., "Purification and Cell-Surface Marker Characterization of Quiescent Satellite Cells From Murine Skeletal Muscle by a Novel Monoclonal Antibody," Exp Cell Res, vol. 296, pp. 245-255 (Mar. 2004).
Gayraud-Morel, B., et al., "Myf5 Haploinsufficiency Reveals Distinct Cell Fate Potentials for Adult Skeletal Muscle Stem Cells," Journal of Cell Science, vol. 125, pp. 1738-1749 (May 7, 2012).
Gayraud-Morel, B., et al., "Skeletal Muscle as a Paradigm for Regenerative Biology and Medicine," Regen. Med. vol. 4, No. 2, pp. 293-319 (Mar. 2009).
Haegele, L., et al., "WNT Signalling Inhibits Neural Differentiation of Embryonic Stem Cells by Controlling Bone Morphogenetic Protein Expression," Mol. Cell Neuroscince, vol. 24, No. 3, pp. 696-708 (Nov. 2003).
Han, X., "A WNT/Beta-Catenin Signaling Activator, R-Spondin, Plays Positive Regulatory Roles During Skeletal Myogenesis" J Biol Chem, vol. 286, pp. 10649-10659 (Mar. 25, 2011).
Hankenson, K. et al., "Thrombospondins and Novel TSR-Containing Proteins, R-Spondins, Regulate Bone Formation and Remodeling," Curr Osteoporos Rep, vol. 8, pp. 68-76 (Apr. 14, 2010).
Hirsinger, E., "Somite Formation and Patterning" Int Rev Cytol, vol. 198, pp. 1-65 (2000).

(56) References Cited

OTHER PUBLICATIONS

Hoffman, L., et al. "Characterization and Culture of Human Embryonic Stem Cells," Nature Biotech., vol. 23, No. 6, pp. 699-708 (Jun. 2005).
Hollnagel, A., et al., "Id Genes Are Direct Targets of Bone Morphogenetic Protein Induction in Embryonic Stem Cells," The Journal of Biological Chemistry, vol. 274, No. 28, pp. 19838-19845 (Jul. 9, 1999).
Hug, B., et. al., "tbx6, a Brachyury-Related Gene Expressed by Ventral Mesendodermal Precursors in the Zebrafish Embryo," Developmental Biology, vol. 183, pp. 61-73 (Mar. 1, 1997).
Jin, Y, et al., "The Canonical WNT Signaling Activator, R-spondin2, Regulates Craniofacial Patterning and Morphogenesis Within the Branchial Arch Through Ectodermal-Mesenchymal Interaction" Dev Biol vol. 352, pp. 1-13 (Apr. 1, 2011).
Kazanskaya, O., "R-Spondin2 is a secreted activator of Wnt/beta-catenin signaling and is required for Xenopus myogenesis," Dev Cell, vol. 7, pp. 525-534 (Oct. 2004).
Kazanskaya, O., et al., "The WNT Signaling Regulator R-Spondin 3 Promotes Angioblast and Vascular Development" Development, vol. 135, pp. 3655-3664 (Sep. 8, 2008).
Kennedy, K., et al., "Retinoic acid enhances skeletal muscle progenitor formation and bypasses inhibition by bone morphogenetic protein 4 but not dominant negative beta-catenin," BMC Biol, vol. 7, pp. 1-21 (Oct. 8, 2009).
Kim, K. et al., "R-Spondin Family Members Regulate the WNT Pathway by a Common Mechanism" Mol Biol Cell, vol. 19, pp. 2588-2596 (Jun. 2008).
Krol, A., et al., "Evolutionary Plasticity of Segmentation Clock Networks," Development, vol. 138, No. 13, pp. 2783-2792 (Apr. 26, 2011).
Lako, M., et al., "Characterisation of WNT Gene Expression During the Differentiation of Murine Embryonic Stem Cells In Vitro: Role of Wnt3 in Enhancing Haematopoietic Differentiation," Mech. Dev., vol. 103, No. 1-2, pp. 49-59 (May 2001).
Lange, C., et al., "WNT signal pathways and neural stem cell differentiation. Neurodegenerative Diseases," vol. 3, pp. 76-86 (May 17, 2006).
Li, W., et al., "Human Pluripotent Stem Cells: Decoding the Naïve State," Sci. Transl. Med., vol. 3, Issue 76, pp. 1-4 (Mar. 30, 2011).
Loser, P., et al., "Human Embryonic Stem Cell Lines and Their Use in International Research," Stem Cells, vol. 28, pp. 240-246 (Feb. 2010).
McBurney, M., et al., "Control of Muscle and Neuronal Differentiation in a Cultured Embryonal Carcinoma Cell Line," Nature, vol. 299, pp. 165-167 (Jun. 28, 1982).
McMahon, J., et al., "Noggin-mediated antagonism of BMP signaling is required for growth and patterning of the neural tube and somite," Genes & Development, vol. 12, pp. 1438-1452 (Mar. 16, 1998).
Metallo, C. et al., "Engineering the Stem Cell Microenvironment," Biotechnol Prog, vol. 23, pp. 18-23 (Jan. 5, 2007).
Mizuno, Y., et al., "Generation of Skeletal Muscle Stem/Progenitor Cells From Murine Induced Pluripotent Stem Cells," FASEB J, vol. 24, pp. 2245-2253, (Feb. 24, 2010).
Montcouquiol, M., et al., "Noncanonical WNT Signaling and Neural Polarity," Annu Rev Neurosci, vol. 29, pp. 363-386, (Jul. 2006).
Myers, E., et al., "Optimal Alignments in Linear Space," CABIOS, vol. 4, No. 1, p. 11-17 (Mar. 1, 1988).
Nam, J., et al., "Dynamic expression of R-spondin family genes in mouse development," Gene Expr Patterns, vol. 7, pp. 306-312 (Jan. 2, 2007).
Nam, J., et al., "Mouse Cristin/R-spondin Family Proteins Are Novel Ligands for the Frizzled 8 and LRP6 Receptors and Activate Beta-Catenin-Dependent Gene Expression," J Biol Chem, vol. 281, pp. 13247-13257 (May 12, 2006).
Nusse, R., "WNT Signaling and Stem Cell Control," Cell Res., vol. 18, pp. 523-527 (Apr. 8, 2008).
Ohkawara, B., "Rspo3 Binds Syndecan 4 and Induces Wnt/Pcp Signaling via Clathrin-Mediated Endocytosis to Promote Morphogenesis," Dev Cell, vol. 20, pp. 303-314 (Mar. 15, 2011).
Okuda, T., et al., "RUNX1/AML1: A Central Player in Hematopoiesis", Int J of Hematology, vol. 74, pp. 252-257 (May 23, 2001).
Paris, D, et al., "Theriogenology, Equine Embryos and Embryonic Stem Cells: Defining Reliable Markers of Pluripotency," vol. 74, pp. 516-524 (Sep. 1, 2010).
Park, I., et al., "Disease-Specific Induced Pluripotent Stem Cells," Cell, vol. 134, pp. 877-886 (Sep. 5, 2008).
Park, I., et al., "Reprogramming of Human Somatic Cells to Pluripotency With Defined Factors," Nature, vol. 451, pp. 141-145 (Jan. 10, 2008).
Pourquié, O., et al., "Lateral and Axial Signals Involved in Avian Somite Patterning: A Role for BMP4," Cell, vol. 84, pp. 461-471 (Feb. 9, 1996).
Prelle, K., et al., "Overexpression of Insulin-Like Growth Factor-11 in Mouse Embryonic Stem Cells Promotes Myogenic Differentiation." Biochem Biophys Res Commun, vol. 277, pp. 631-638 (Nov. 2, 2000).
Reshef, R., et al., "Regulation of Dorsal Somitic Cell Fates: BMPs and Noggin Control the Timing and Pattern of Myogenic Regulator Expression," Genes & Development, vol. 12, pp. 290-303 (Feb. 1, 1998).
Ring, D. et al., "Selective Glycogen Synthase Kinase 3 Inhibitors Potentiate Insulin Activation of Glucose Transport and Utilization In Vitro and In Vivo," Diabetes, vol. 52, pp. 588-595 (Mar. 2003).
Rohwedel, J., et al., "Muscle Cell Differentiation of Embryonic Stem Cells Reflects Myogenesis In Vivo: Developmentally Regulated Expression of Myogenic Determination Genes and Functional Expression of Ionic Currents," Dev Biol, vol. 164, pp. 87-101 (Feb. 8, 1994).
Sakurai, H., et al., "Bidirectional Induction Toward Paraxial Mesodermal Derivatives From Mouse Es Cells in Chemically Defined Medium," Stem Cell Research, vol. 3, pp. 157-169 (Aug. 8, 2009).
Sakurai, H., et al., "In Vitro Modelling of Paraxial and Lateral Mesoderm Differentiation Reveals Early Reversibility," Stem Cells, vol. 24, No. 3, pp. 575-586 (Mar. 1, 2006).
Sakurai, H., et al., "Paraxial mesodermal progenitors derived from mouse embryonic stem cells contribute to muscle regeneration via differentiation into muscle satellite cells," Stem Cells, vol. 26, No. 7, pp. 1865-1873 (May 1, 2008).
Sato, N., et al., "Maintenance of Pluripotency in Human and Mouse Embryonic Stem Cells Through Activation of Wnt Signaling by a Pharmacological Gsk-3-Specific Inhibitor," Nature Medicine, vol. 10, No. 1, pp. 55-63 (Jan. 2004).
Schlessinger, K, et al., "WNT Signaling Pathways Meet Rho Gtpases," Genes Dev, vol. 23, pp. 265-277 (Feb. 2009).
Schröder, Arnopld Günter, "Differenzierung embryonaler Stammzellen der Maus zu paraxialem Mesoderm in vitro," Universitätsbibliothek der Freien Universität Berlin, Front page-105 (Jun. 6, 2011) http://www.diss.fu-berlin.de/diss/receive/FUDISS_thesis_000000023130—English abstract.
Scott, I., et al., "Spatiotemporal Expression Patterns of Mammalian Chordin During Postgastrulation Embryogenesis and in Postnatal Brain," Developmental Dynamics, vol. 217, pp. 449-456 (Jan. 11, 2000).
Shani, M., et al., "The Consequences of a Constitutive Expression of Myod1 in Es Cells and Mouse Embryos," Symp Soc Exp Biol, vol. 46, pp. 19-36 (Dec. 1991).
Shelton, M., et al., "Derivation and Expansion of PAX7-Positive Muscle Progenitors from Human and Mouse Embryonic Stem Cells," Stem Cell Reports, vol. 3, pp. 516-529 (Sep. 2014).
Skerjanc, I. S., "Cardiac and Skeletal Muscle Development in P19 Embryonal Carcinoma Cells," Trends Cardiovasc Med, vol. 9, pp. 139-143 (Jul. 1999).
Stafford, D., et al., "Cooperative Activity of Noggin and Gremlin 1 in Axial Skeleton Development," Development, vol. 138, No. 5, pp. 1005-1014 (Feb. 8, 2011).
Szeto, D., et al., "Combinatorial Gene Regulation by Bmp and Wnt in Zebrafish Posterior Mesoderm Formation," Development, vol. 131, No. 15, pp. 3751-3760 (Apr. 21, 2004).

(56) References Cited

OTHER PUBLICATIONS

Taelman, V. F., "Wnt Signaling Requires Sequestration of Glycogen Synthase Kinase 3 Inside Multivesicular Endosomes," Cell, vol. 143, pp. 1136-1148 (Dec. 23, 2010).
Takahashi, K., et al., "Induction of Pluripotent Stem Cells From Adult Human Fibroblasts by Defined Factors," Cell, vol. 131, pp. 861-872 (Nov. 30, 2007).
Takahashi, K., et al., "Induction of Pluripotent Stem Cells From Mouse Embryonic and Adult Fibroblast Cultures by Defined Factors," Cell, vol. 126, pp. 663-676 (Aug. 25, 2006).
Takebe, A., et al., "Microarray Analysis of PDGFRα+ Populations in ES Cell Differentiation Culture Identifies Genes Involved in Differentiation of Mesoderm and Mesenchyme Including Arid3b That Is Essential for Development of Embryonic Mesenchymal Cells," Developmental Biology, vol. 293, pp. 25-37 (Mar. 13, 2006).
Takeuchi, J., et. al., "Tbx5 and Tbx4 Genes Determine the Wing/Leg Identity of Limb Buds," Nature, vol. 398, pp. 810-814 (Apr. 1999).
Tanaka, M., et al. "BMP Inhibition Stimulates WNT-Dependent Generation of Chondrogenic Mesoderm From Embryonic Stem Cells," Stem Cell Research, vol. 3, pp. 126-141 (Jul. 10, 2009).
Tomescot, A., et. al., "Differentiation In Vivo of Cardiac Committed Human Embryonic Stem Cells in Postmyocardial Infarcted Rats," Stem Cells, vol. 25, pp. 2200-2205 (May 23, 2007).
Tonegawa, A., et. al., "Mesodermal subdivision along the mediolateral axis in chicken controlled by different concentrations of BMP-4", Development, vol. 124, pp. 1975-1984 (Feb. 19, 1997).
Umeda, K., et al., "Human Chondrogenic Paraxial Mesoderm, Directed Specification and Prospective Isolation From Pluripotent Stem Cells," Scientific Report, vol. 2, No. 455, pp. 1-11 (May 22, 2012).
Verfaillie, C., et al., "Stem cells: hype and reality," Hematology, pp. 369-381 (Jan. 1, 2002).
Wijgerde, M., et al., "Noggin Antagonism of BMP4 Signaling Controls Development of the Axial Skeleton in the Mouse," Developmental Biology, vol. 286, pp. 149-157 (Aug. 24, 2005).
Wittler, L., et al., "Expression of Msgn1 in the Presomitic Mesoderm Is Controlled by Synergism of Wnt Signaling and Tbx6" EMBO Reports, vol. 8, No. 8, pp. 784-789 (Jul. 13, 2007).
Wu, D., et al., "GSK3: A Multifaceted Kinase in WNT Signaling," Trends Biochem Sci, vol. 35, No. 3, pp. 161-168 (Mar. 2010).
Yoon, J., et. al., "The bHLH Regulator pMesogenin1 Is Required for Maturation and Segmentation of Paraxial Mesoderm," Genes Development, vol. 14, pp. 3204-3214 (Nov. 2, 2000).
Yu, J., et al., "Dorsomorphin Inhibits BMP Signals Required for Embryogenesis and Iron Metabolism," Nat Chem Biol., vol. 4, No. 1, pp. 33-41 (Jan. 2008).
Yu, J., et al., "Induced pluripotent stem cell lines derived from human somatic cells," Science, vol. 318, pp. 1917-1920 (Dec. 21, 2007).
Zhou, J., et al., "High-Efficiency Induction of Neural Conversion in hESCs and hiPSCs with a Single Chemical Inhibitor of TGF-β Superfamily Receptors," Stem Cell, vol. 28, No. 10, pp. 1741-1750 (Oct. 2010).
Caron, L., et al., "A Human Pluripotent Stem Cell Model of Facioscapulohumeral Muscular Dystrophy-Affected Skeletal Muscles," Stem Cells Translational Medicine, vol. 5, pp. 1-17 (May 23, 2016).
Chetty, S., et al., "A Simple Tool to Improve Pluripotent Stem Cell Differentiation," Nat. Methods, vol. 10, No. 6, pp. 553-556 (Jun. 2013).
Choi, Y., et al., "Concordant but Varied Phenotypes Among Duchenne Muscular Dystrophy Patient-Specific Myoblasts Derived Using a Human iPSC-Based Model," Cell Reports, vol. 15, pp. 1-12 (Jun. 7, 2016).
Davies, O., et al., "Tcf15 Primes Pluripotent Cells for Differentiation," Cell Reports, No. 3, pp. 472-484 (Feb. 21, 2013).
Davis, R., et al., "Targeting a GFP Reporter Gene to the MIXL1 Locus of Human Embryonic Stem Cells Identifies Human Primitive Streak-Like Cells and Enables Isolation of Primitive Hematopoietic Precursors," Blood, vol. 111, No. 4, pp. 1876-1884 (Feb. 15, 2008).
Ding, G., et al., "Pdgf Receptor Alpha+ Mesoderm Contributes to Endothelial and Hematopoietic Cells in Mice," Developmental Dynamics, vol. 242, pp. 254-268 (Jan. 17, 2013).
Ema, M., et al., "Deletion of the Selection Cassette, but not Cis-Acting Elements, in Targeted Flk1-lacZ allele Reveals Flk1 Expression in Multipotent Mesodermal Progenitors," Hemostasis, Thrombosis, and Vascular Biology, vol. 107, No. 1, pp. 111-117 (Jan. 1, 2006).
Hwang, Y., et al., "WNT3A Promotes Myogenesis of Human Embryonic Stem Cells and Enhances in vivo Engraftment," Scientific Reports, vol. 4, pp. 1-9, (Aug. 1, 2014).
Kirilenko, P., et al., "Transient Activation of Meox1 Is an Early Component of the Gene Regulatory Network Downstream of Hoxa2," Molecular and Cellular Biology, vol. 31, No. 6, pp. 1301-1308 (Mar. 2011).
Li, F., et al., "Combined Activin A/LiCl/Noggin Treatment Improves Production of Mouse Embryonic Stem Cell-Derived Definitive Endoderm Cells," Journal of Cellular Biochemistry, vol. 112, pp. 1022-1104 (Mar. 11, 2011).
Loh, K., et al., Mapping the Pairwise Choices Leading from Pluripotency to Human Bone, Heart, and Other Mesoderm Cell Types, Cell, vol. 166, pp. 451-467 (Jul. 14, 2016).
Menendez, L., et al., "Wnt Signaling and a Smad Pathway Blockade Direct the Differentiation of Human Pluripotent Stem Cells to Multipotent Neural Crest Cells," PNAS, vol. 108, No. 48, pp. 19240-19245 (Nov. 29, 2011).
Motoike, T., et al., "Evidence for Novel Fate of Flk1+ Progenitor: Contribution to Muscle Lineage," Genesis vol. 35, pp. 153-159 (Feb. 6, 2003).
Pereira, L., et al., "The Mix Family of Homeobox Genes—Key Regulators of Mesendoderm Formation During Vertebrate Development," Developmental Biology, vol. 367, pp. 163-177 (Jul. 15, 2012).
Sudheer, S., et al., Different Concentrations of FGF Ligands, FGF2 or FGF8 Determine Distinct States of WNT-Induced Presomitic Mesoderm, Stem Cells, vol. 34, Issue 7, pp. 1790-1800 (Apr. 18, 2016).
Li, S., et al., Magazine of the Japanese Society for Regenerative Medicine, vol. 10, Suppl. 2011, p. 175 (2011) English translation Abstract.
Borchin, B., et al., "Derivation and FACS-Mediated Purification of PAX3+/PAX7+ Skeletal Muscle Precursors from Human Pluripotent Stem Cells," Stem Cell Reports, vol. I, pp. 620-631 (Dec. 17, 2013).
Chal, J., et al., "Generation of Human Muscle Fibers and Satellite-Like Cells from Human Pluripotent Stem Cells in vitro," Nature Protocols, vol. 11, No. 10, pp. 1833-1850 (Sep. 1, 2016).
Chal, J., et al., "Recapitulating Early Development of Mouse Musculoskeletal Precursors of the Paraxial Mesoderm in vitro," bioRxivi preprint first posted online May 22, 2017.
Chalamalasetty, R., et al., "Mesogenin 1 is a Master Regulator of Paraxial Presomitic Mesoderm Differentiation," Biologists, vol. 141, pp. 4285-4297 (Nov. 2014).
Iovino, S., "Myotubes Derived from Human-Induced Pluripotent Stem Cells Mirror in vivo Insulin Resistance," PNAS, vol. 113, No. 7, pp. 1889-1894 (Feb. 16, 2016).
Mendjan, S., et al., "NANOG and CDX2 Pattern Distinct Subtypes of Human Mesoderm During Exit from Pluripotency," Cell Stem Cell, vol. 15, pp. 310-325 (Sep. 4, 2014).
Shelton, M., et al., "Robust Generation and Expansion of Skeletal Muscle Progenitors and Myocytes from Human Pluripotent Stem Cells," Methods, vol. 101, pp. 73-84 (May 15, 2016).
Swartz, E., et al., "A Novel Protocol for Directed Differentiation of C9orf72-Associated Human Induced Pluripotent Stem Cells Into Contractile Skeletal Myotubes," Stem Cells Translational Medicine, vol. 5, pp. 1461-1472 (Jul. 1, 2016).
Ki, H., et al., "In Vivo Human Somitogenesis Guides Somite Development from hPSCs," Cell Reports, vol. 18, pp. 1573-1585 (Feb. 7, 2017).
Xu, C., et al., "A Zebrafish Embryo Culture System Defines Factors that Promote Vertebrate Myogenesis Across Species," Cell, vol. 155, pp. 909-921 (Nov. 7, 2013).

(56) References Cited

OTHER PUBLICATIONS

Yoon, J. et al., "The bHLH Class Protein pMesogenin1 Can Specify Paraxial Mesoderm Phenotypes," Developmental Biology, vol. 222, Issue 2, pp. 376-391 (Jun. 15, 2000).
MacDonald, B., et al., "Wnt/β-Catenin Signaling: Components, Mechanisms, and Diseases," Developmental Cell Review, No. 17, pp. 9-26 (Jul. 21, 2009).
Kim, Kyung-Ah, et al., "R-Spondin Proteins: A Novel Link to β-catenin Activation," Cell Cycle, vol. 5, No. 1, pp. 23-26 (Jan. 1, 2006).

\* cited by examiner

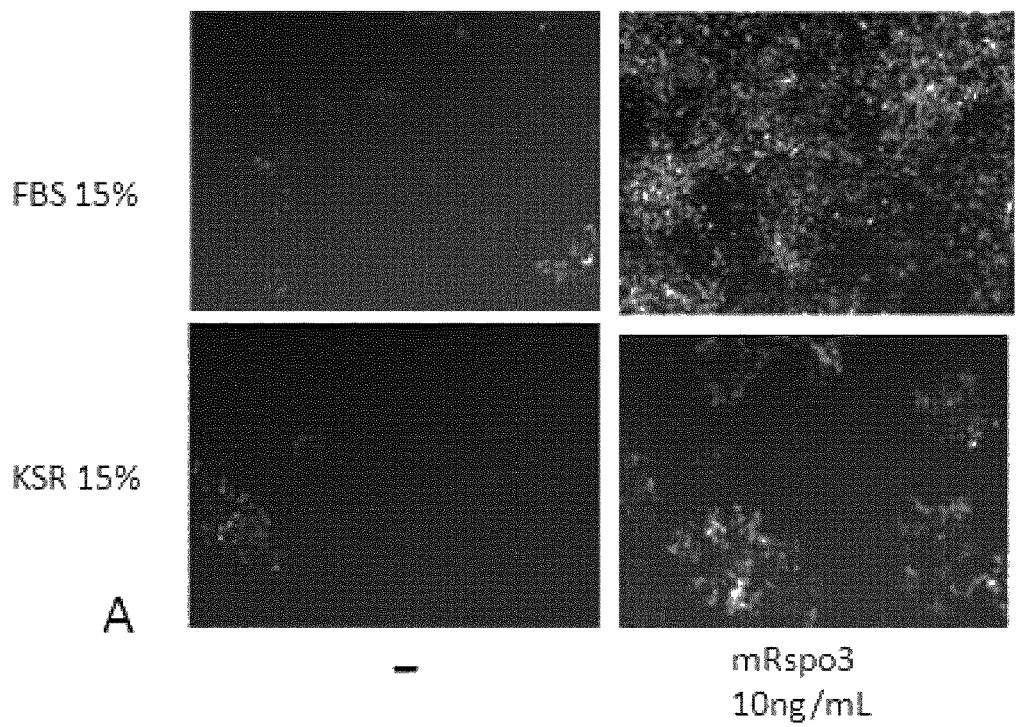
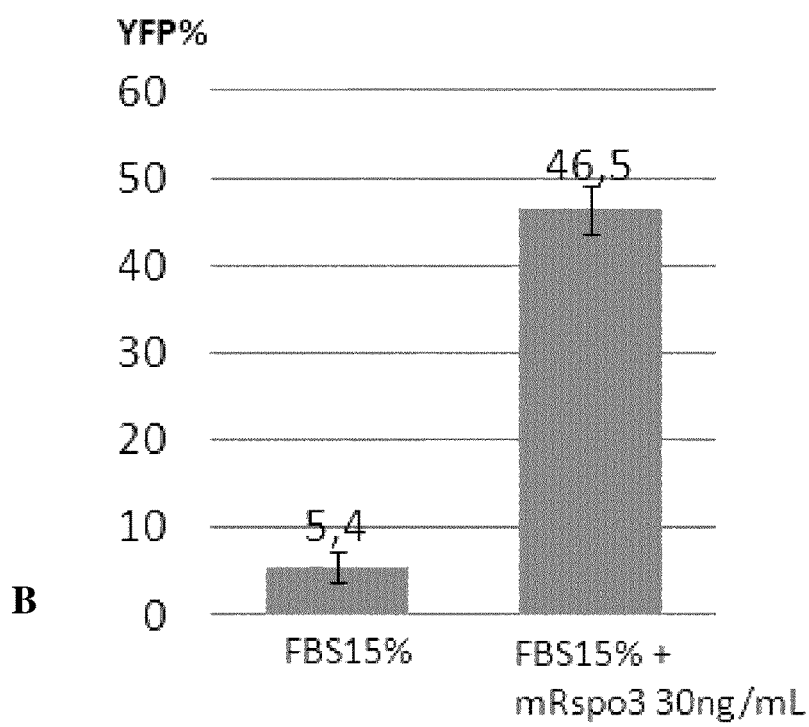
Figure 1

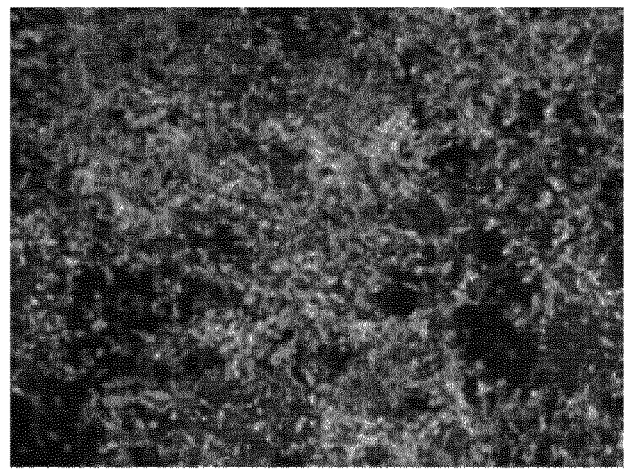
A
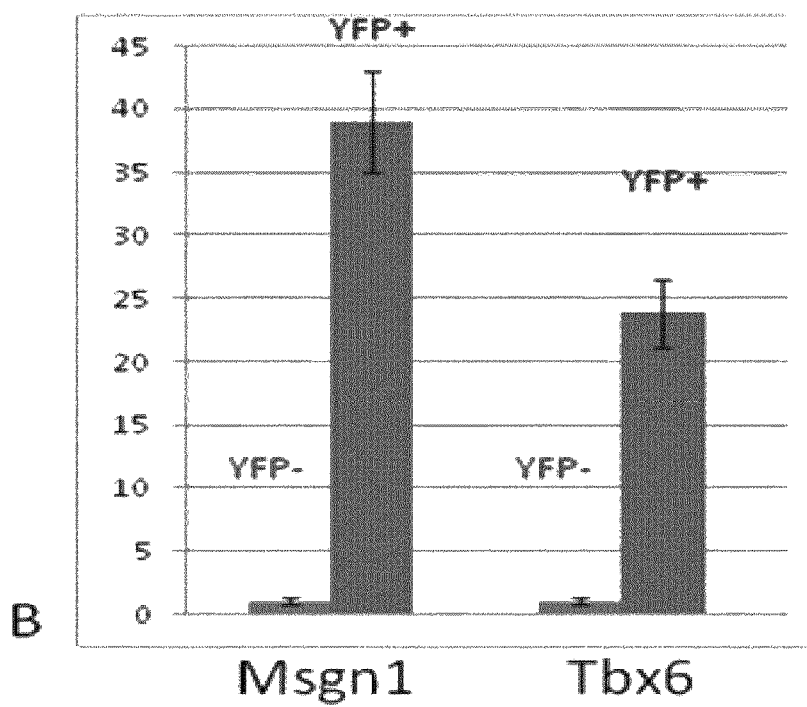
B
Figure 3

Desmin (day18)

PECAM1 (CD31) (day18)

Alcian blue (day18)

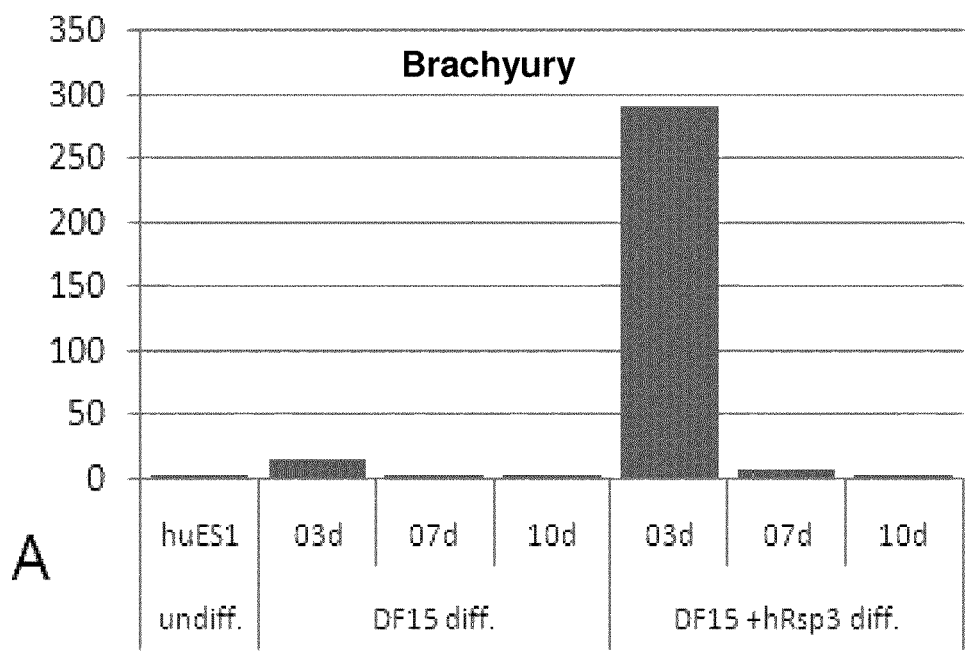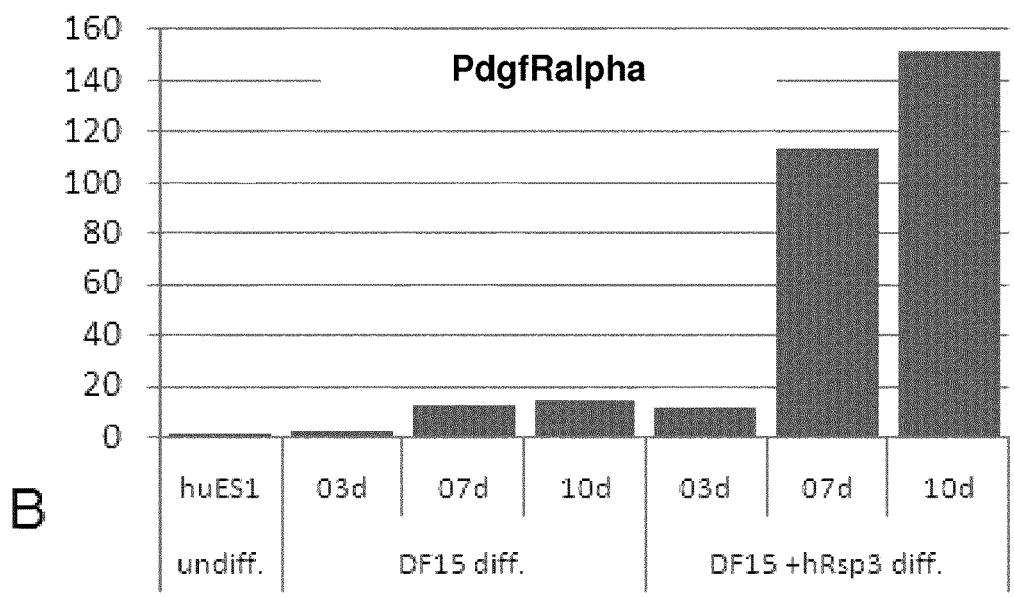
Figure 10 A and B

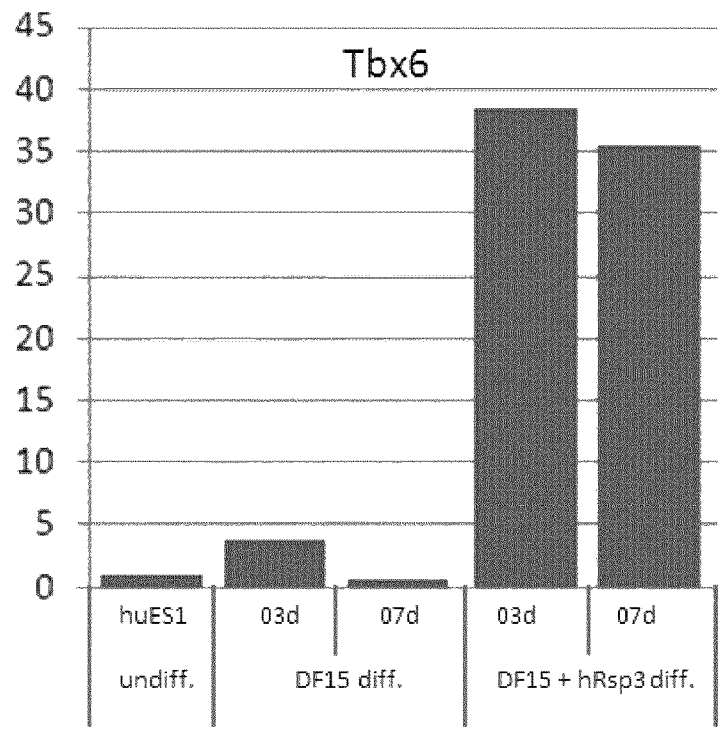
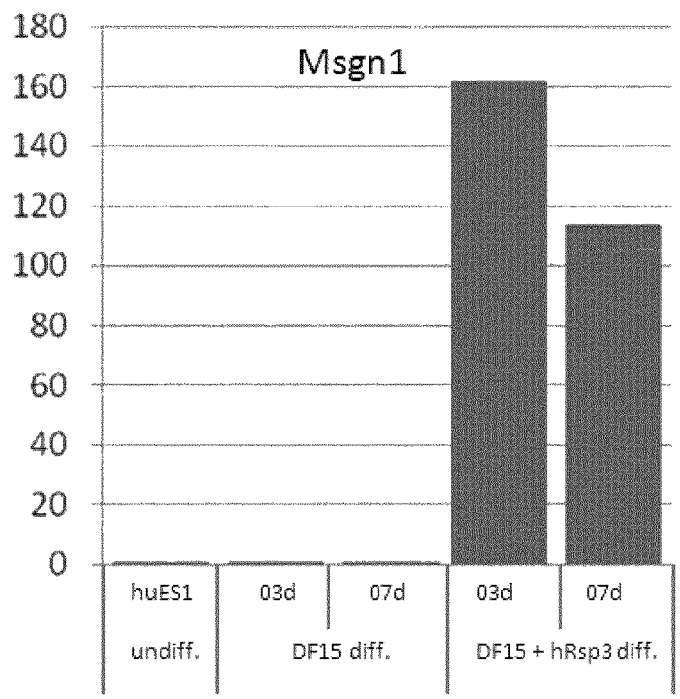
Figure 10 C and D

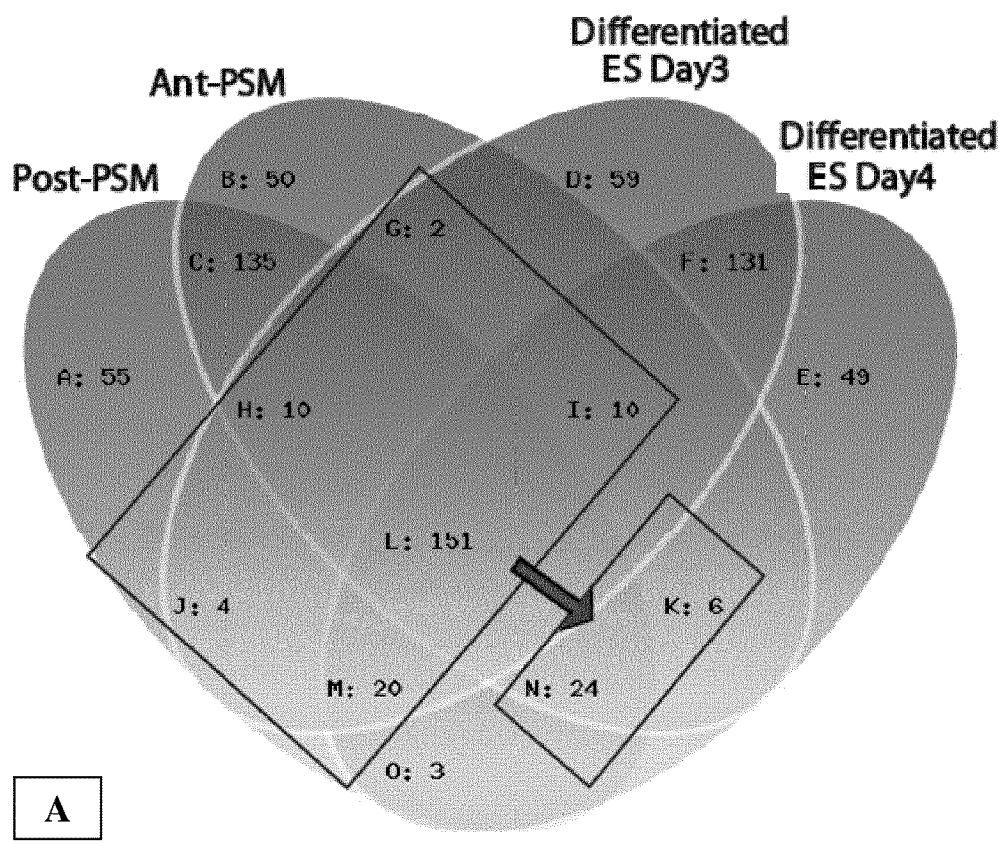
Figure 12 A and B

Figure 13:
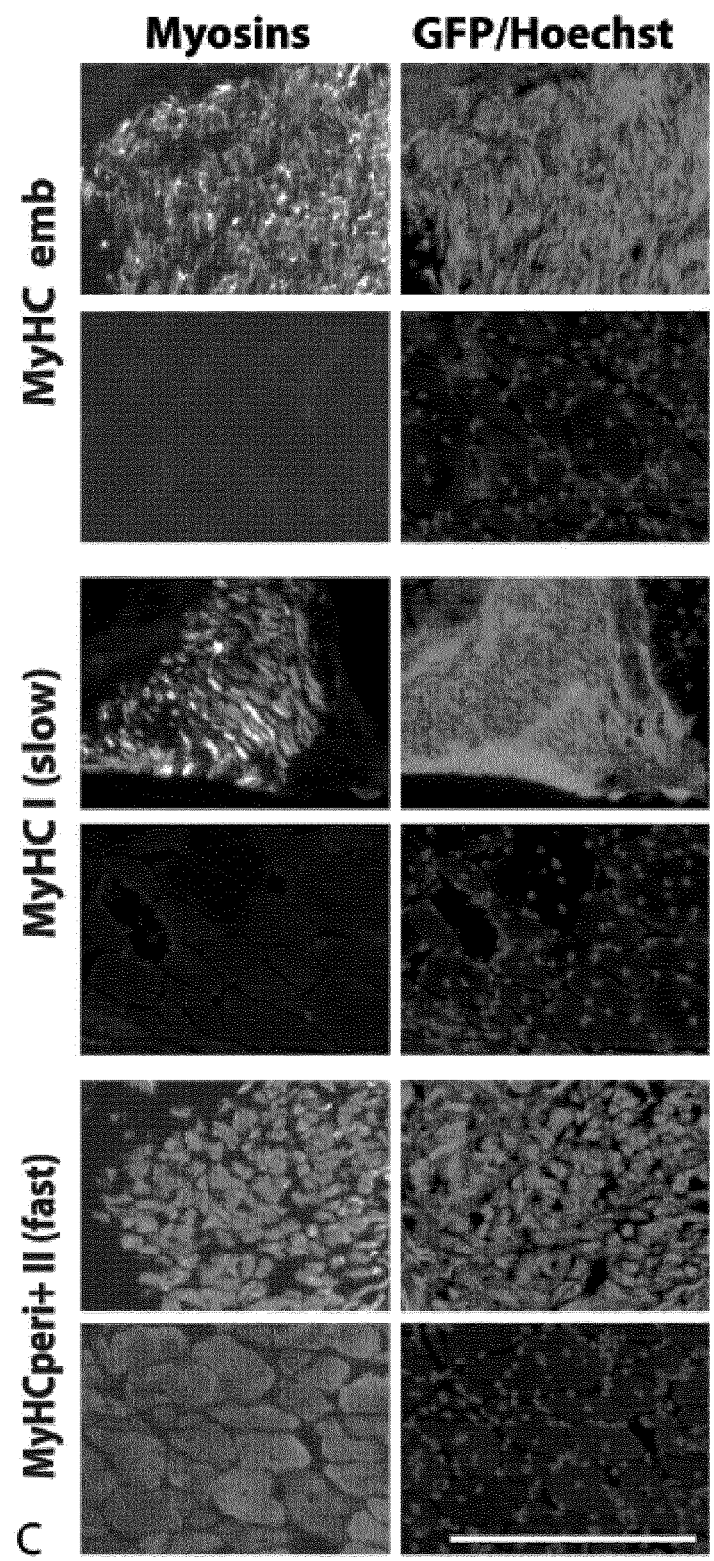

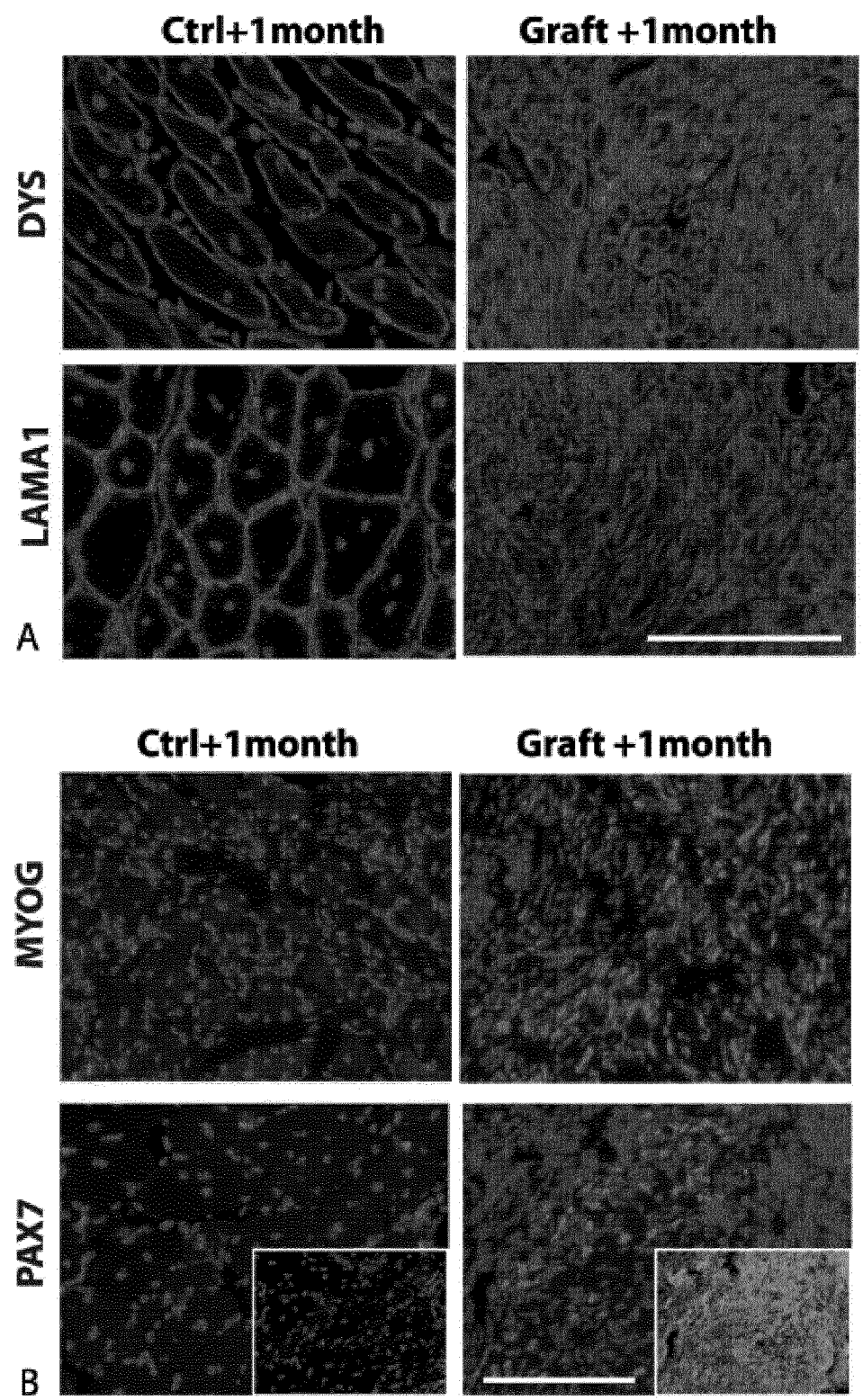
Figure 13 A and B

METHOD FOR PREPARING INDUCED PARAXIAL MESODERM PROGENITOR (IPAM) CELLS AND THEIR USE

FIELD OF THE INVENTION

The present invention relates to an ex vivo method for preparing induced paraxial mesoderm progenitor (iPAM) cells, said method comprising the step of culturing pluripotent cells in an appropriate culture medium comprising an effective amount of an activator of the Wnt signaling pathway and an effective amount of an inhibitor of the Bone Morphogenetic Protein (BMP) signaling pathway.

BACKGROUND OF THE INVENTION

Embryonic stem (ES) cell research offers unprecedented potential for understanding fundamental developmental processes, such as lineage differentiation. Embryonic stem cell lines are derived from early embryos and are characterized by their ability to self-renew, that is, to be maintained indefinitely in a proliferative and undifferentiated state in culture. ES cells are also pluripotent, meaning they retain the capacity to differentiate into the three embryonic lineages: ectoderm, mesoderm and endoderm plus all of their derivatives (Chambers I., 2004). The recent development of reprogramming technologies now allows ES-like stem cells to be generated from somatic cells, such as fibroblasts. Introduction into somatic cells of a small set of specific transcription factors—Oct4, Sox2, c-Myc, and Klf4 in the mouse (Takahashi and Yamanaka, 2006) and human (Park et al., 2008b; Takahashi et al., 2007), or Oct4, Sox2, Nanog and Lin28 in human (Yu et al., 2007)—can reprogram various differentiated cell types to an ES-like stem cell state (induced pluripotent stem cells or iPS). This strategy now allows the generation of ES-like cell lines from individual patients and, thus, offers the possibility to create highly relevant in vitro models of human genetic diseases. Such reprogrammed cell lines have already been generated from patients with a variety of diseases, such as Duchenne Muscular Dystrophy or Amyotrophic lateral sclerosis (ALS) and differentiation of the reprogrammed cells into the deficient tissue has been achieved for iPS cells from patients affected with several diseases such as ALS, thus, demonstrating the feasibility of the approach (Dimos et al., 2008; Park et al., 2008a).

Whereas some lineages such as cardiac myocytes or neurons are easily generated in vitro from ES cells, differentiating paraxial mesoderm derivatives such as skeletal muscle, dermis, cartilage or bone from ES or iPS cells has proven to be challenging. Given the promises offered by cellular replacement therapy for the cure of some muscular degenerative diseases or for orthopaedic surgery, the development of protocols for production of precursors of muscle and skeletal lineages is of key importance. In the embryo, the muscles, the dorsal dermis and the axial skeleton of the body derive from the paraxial mesoderm and more specifically from multipotent precursors forming the presomitic mesoderm (PSM). These precursors are characterized by expression of the genes Brachyury (T), Tbx6 and Mesogenin1 (Msgn1) (Chapman et al., 1996; Yoon and Wold, 2000) and they mostly differentiate into skeletal muscles, dermis, skeletal lineages, as well as in a variety of other derivatives including adipocytes and endothelial cells. In the mouse embryo, Rspo3 (also called Cristin1, Thsd2) is strongly expressed in the PSM and somites, as well as later in condensing mesenchymal cells, (Kazanskaya et al., 2004; Nam et al., 2007). R-spondins (Rspo1 to 4 genes) are secreted molecules containing a thrombospondin domain, that can activate canonical Wnt signaling and Beta-Catenin, via the Fzd/LRP/Lgr4/Lgr5 co-receptors complex (Carmon et al., 2011; de Lau et al., 2011; Kim et al., 2008; Nam et al., 2006), but they were also shown to bind Syndecan4 and induce Wnt/PCP signaling (Ohkawara et al., 2011). Interestingly, biochemical assays show that Rspo2 and 3 are more potent to activate Wnt signaling than Rspo1 and 4 (Kim et al., 2008). R-spondins have also been shown to be implicated in bone formation and chondrogenesis (Hankenson et al., 2010; Jin et al., 2011; Ohkawara et al., 2011), myogenesis (Han et al., 2011; Kazanskaya et al., 2004) and angiogenesis (Kazanskaya et al., 2008).

Bone Morphogenetic Proteins (BMPs) are secreted molecules of the TGFbeta superfamily that can dimerize and activate BMP signaling and bind to a receptor complex constituted of BMP receptor type I and type II (BMPR-I and -II). More precisely, BMPR-I can consist of Activin receptor-like kinase (ALK)-2/3 and 6 (also known as ActR-IA, BMPR-IA and BMPR-IB respectively). Similarly, BMPR-II can consist of BMPR-II, ActR-IIA and ActR-IIB. The BMP receptor complex is formed by an heterotetrameric complex of two BMPR-I and two BMPR-II. The BMP receptor contains an intracytoplasmic serine/threonine kinase domain which allows the phosphorylation of Smad 1/5/8 upon binding of the BMP dimer. Phosphorylated Smad1/5/8 then associate to Smad4 and shuttle to the nucleus to activate target genes, which include the inhibitor of DNA binding (Id) 1/2/3 genes [Hollnagel A et al., 1999]. Importantly, numerous BMP/TGFβ secreted agonists and antagonists have been described to regulate and fine-tune BMP signaling during development. Most notably noggin, chordin, follistatin and gremlin block BMP signaling by sequestrating secreted BMP, preventing its binding to the receptor. BMP ligands (prominently BMP2, 4 and 7), BMP receptors, Smads, Co-Smads and BMP agonists/antagonists have been implicated in mesoderm specification and organogenesis during development [Derynck Rik, 2008; Reshef R. et al, Gen Dev 1998; Wijgerde M. et al, 2005; McMahon J A et al, 1998; Stafford D A et al, 2011; Pourquié O. et al, 1996 and Tonegawa A. et al, 1997].

Differentiation of ES cells into paraxial mesoderm and its derivatives is highly inefficient in vitro. Limited spontaneous skeletal muscle differentiation has been described following culture of mouse embryoid bodies and DMSO treatment (Dinsmore et al., 1996; Rohwedel et al., 1994), or Retinoic acid treatment (Kennedy et al., 2009). Two distinct strategies to differentiate mouse and human ES cells in vitro to the muscle lineage have been reported. The first one involves the sorting of precursors using surface markers. For instance, Studer's group reported the isolation of human ES cells-derived CD73+ mesenchymal precursors and their subsequent differentiation into skeletal muscle following a culture period in serum containing medium (Barberi et al., 2007). The antibody against satellite cells SM/C-2.6 was also used to isolate myogenic cells differentiated from mouse ES and iPS cells (Fukada et al., 2004; Mizuno et al., 2010). Finally, mesoderm precursors differentiated from mouse ES cells were also isolated based on their expression of other surface markers such as the Platelet derived growth factor receptor alpha (PDGFRa) or Vascular endothelial growth factor receptor 2 (VEGFR2) ((Sakurai et al., 2009; Sakurai et al., 2008) Sakurai H. et al., 2006; Takebe A. et al, 2006). Whether this combination of markers is strictly specific for paraxial mesoderm precursors has however not been demonstrated. The second strategy is based on forced expression of the transcription factors Pax3 or MyoD, or of the secreted factor Insulin Growth Factor 2 (IGF-2) in mouse ES cells (Darabi et al., 2008; Darabi et al., 2011; Dekel et al., 1992; Prelle et al., 2000; Shani et al., 1992). However, these strategies show either limited efficiency or require introduction of exogenous DNA in the ES cells which is a major hurdle for the development of safe cell therapies and the differentiated cells often show limited proliferation and engraftment potential.

Therefore, there is a need to develop better ES and iPS cell differentiation strategies to produce muscle cells and paraxial mesoderm derived lineages for the development of applications in regenerative medicine.

The present invention fulfils this need by providing a method for preparing multipotent progenitor cell lines expressing markers of the paraxial mesoderm progenitors and referred to as induced Paraxial Mesoderm progenitor cells or iPAM to distinguish them from the natural embryo Paraxial Mesoderm progenitor cells. Like their in vivo counterpart, the iPAM cells are capable of giving rise to cell lineages of the muscular, skeletal (bone and cartilage), dermal tissue, and derivatives such as adipocytes and endothelium. The inventors have shown that embryonic stem cells or pluripotent reprogrammed cells (iPS) can be differentiated into induced Paraxial Mesoderm progenitor (iPAM) cells using a limited number of factors. In particular, the inventors have made the surprising finding that it is possible to efficiently obtain induced Paraxial Mesoderm progenitor (iPAM) cells by treatment with specific factors, without any genetic modification of the target cells. They have shown that the obtained induced Paraxial Mesoderm progenitor (iPAM) cells exhibit characteristics of endogenous Paraxial mesoderm progenitor cells. To the applicant's knowledge, the invention is the first description of a method for obtaining unlimited amounts of cells suitable for use as progenitor cells for regenerating either muscle, skeletal, adipose or dermal tissues and paraxial mesoderm derived endothelium. Therefore the invention is highly useful in particular in regenerative medicine.

SUMMARY OF THE INVENTION

Thus, the present invention relates to an ex vivo method for preparing induced paraxial mesoderm progenitor (iPAM) cells, said method comprising the step of culturing pluripotent cells in an appropriate culture medium comprising an effective amount of an activator of the Wnt signaling pathway.

Particularly, the present invention relates to an ex vivo method for preparing induced paraxial mesoderm progenitor (iPAM) cells, said method comprising the step of culturing pluripotent cells in an appropriate culture medium comprising an effective amount of an activator of the Wnt signaling pathway and an effective amount of an inhibitor of the Bone Morphogenetic Protein (BMP) signaling pathway.

More particularly, the invention relates to an ex vivo method for preparing induced paraxial mesoderm progenitor (iPAM) cells, said method comprising the step of culturing pluripotent cells in an appropriate culture medium comprising an effective amount of a member of the R-spondin family and an effective amount of an inhibitor of the Bone Morphogenetic Protein (BMP) signaling pathway.

The invention also relates to an alternate method comprising the step of culturing pluripotent cells in an appropriate culture medium comprising an effective amount of a member of an inhibitor of the GSK-3ß and an effective amount of an inhibitor of the Bone Morphogenetic Protein (BMP) signaling pathway.

DETAILED DESCRIPTION OF THE INVENTION

Method for Preparing Induced Paraxial Mesoderm Progenitor (iPAM) Cells

A first aspect of the invention relates to an ex vivo method for preparing induced Paraxial Mesoderm progenitor (iPAM) cells, said method comprising the step of culturing pluripotent cells in an appropriate culture medium comprising an effective amount of an activator of the Wnt signaling pathway.

In another particular aspect, the invention also relates to an ex vivo method for preparing a population of induced Paraxial Mesoderm progenitor (iPAM) cells, said method comprising the step of culturing pluripotent cells in an appropriate culture medium comprising an effective amount of an activator of the Wnt signaling pathway.

In a particular aspect, the invention also relates to an ex vivo method for preparing induced Paraxial Mesoderm progenitor (iPAM) cells, said method comprising the step of culturing pluripotent cells in an appropriate culture medium comprising an effective amount of an activator of the Wnt signaling pathway and an effective amount of an inhibitor of the Bone Morphogenetic Protein (BMP) signaling pathway.

In a particular aspect, the invention relates to an ex vivo method for preparing a population of induced Paraxial Mesoderm progenitor (iPAM) cells, said method comprising the step of culturing pluripotent cells in an appropriate culture medium comprising an effective amount of an activator of the Wnt signaling pathway and an effective amount of an inhibitor of the Bone Morphogenetic Protein (BMP) signaling pathway.

As used herein, the term "Wnt signaling pathway" denotes a signaling pathway which may be divided in two pathways: the "canonical Wnt/beta catenin signaling pathway" and the "Wnt/PCP signaling pathway". As used herein, the term "canonical Wnt/beta catenin signaling pathway" or "Wnt/PCP signaling pathway" in its general meaning denotes a network of proteins and other bioactive molecules (lipids, ions, sugars . . . ) best known for their roles in embryogenesis and cancer, but also involved in normal physiological processes in adult animals. The "canonical Wnt/beta catenin signaling pathway" is characterized by a Wnt dependant inhibition of glycogen synthase kinase 3ß (GSK-3ß), leading to a subsequent stabilization of ß-catenin, which then translocates to the nucleus to act as a transcription factor. The "Wnt/PCP signaling pathway" does not involve GSK-3ß or ß-catenin, and comprises several signaling branches including Calcium dependant signaling, Planar Cell Polarity (PCP) molecules, small GTPases and C-Jun N-terminal kinases (JNK) signaling. These pathways are well described in numerous reviews such as (Clevers, 2006; Montcouquiol et al., 2006; Schlessinger et al., 2009).

In one embodiment, the Wnt signaling pathway is the canonical Wnt/ß-catenin signaling pathway.

In another preferred embodiment, the Wnt signaling pathway is the Wnt/PCP signaling pathway.

In another preferred embodiment, the Wnt signaling pathway is the canonical Wnt/ß-catenin signaling pathway and Wnt/PCP signaling pathway.

As used herein the term "activator" denotes a substance that enhances Wnt signaling activity. For example, for the canonical Wnt/ß-catenin signaling pathway, this activity can be measured by Wnt reporter activity using established multimers of LEF/TCF binding sites reporters, and/or inhibition of GSK-3ß, and/or activation of canonical Wnt target genes such as T, Tbx6, Msgn1, or Axin2.

As used herein the term "induced Paraxial Mesoderm progenitor cells" or "iPAM" refers to cells derived from any cell type but exhibiting characteristics of progenitor cells of the Paraxial Mesoderm. In one embodiment, the iPAM cells are characterized by the following properties:

a) they express biomarkers characteristic of Paraxial mesoderm progenitor cells such as Tbx6, EphrinA1, EphrinB2, EPHA4, PDGFRalpha, Sall1, Sall4, Dll1, Dll3, Papc (Pcdh8), Lfng, Hes7, Ripply1, Ripply2, Brachyury (T), Cdx2, Cdx4, Evx1, Cxcr4, Il17rd, Fgf8, Fgf17, Gbx2, Wnt3a, Wnt5b, Rspo3, SP5, SP8, Has2, Dkk1, Dact1, Pax3, Pax7, Mesp1, Mesp2 or Msgn1 genes. Preferentially Msgn1 gene as measured for example with a gene reporter assay comprising the Msgn1 promoter, and;

b) they are multipotent cells, capable of differentiating into at least skeletal, dermis or muscle cell lineages;

c) optionally, they may have long term self-renewal properties, e.g., they can be maintained in culture more than 6 months.

The multipotency of said induced Paraxial Mesoderm progenitor (iPAM) cells can be tested in vitro, e.g., by in vitro differentiation into skeletal, dermal or muscle cell lineages using the protocols described below, and in particular in the Examples.

As used herein, the term "multipotent" refers to cells that can differentiate in more than one cell lineage depending on the environmental and culture conditions. Contrary to embryonic stem cells which are pluripotent and can differentiate into all types of somatic cell lineages, the induced paraxial mesoderm progenitor cells of the present invention have limited differentiation capacity.

The term "pluripotent cells" as used herein refers to mammalian undifferentiated cells which can give rise to a variety of different cell lineages. Typically, pluripotent cells may express the following markers Oct4, SOX2, Nanog, SSEA 3 and 4, TRA 1/81, see International Stem Cell Initiative recommendations, 2007.

In one embodiment, the pluripotent cells are human pluripotent cells.

In another embodiment, the pluripotent cells are non-human mammalian pluripotent cells.

In one embodiment, the pluripotent cells are stem cells. Typically, said stem cells are embryonic stem cells.

In another embodiment, the pluripotent cells are human embryonic stem cells (hES cells). Typically, hES cell lines (Loser et al., 2010) such as the one described in the following table may be employed for the method of the invention:

| line | karyotype | passage available | country of origin | origin |
|---|---|---|---|---|
| SA01 | 46XY | 25 | Sweden | Cellartis AB |
| VUB01 | 46XY | 73 | Belgium | AZ-VUB Bruxel |
| HUES 24, | 46XY | 26 | USA | Harvard |
| H1 | 46XY, 20q11.21 | 26 | USA | Wicell research Institute |
| H9 | 46XX | 27 | USA | Wicell research Institute |
| WT3 | 46XY | 35 | UK | UKSCB |
| HUES1 | 46XX | 33 | USA | Harvard |

In one embodiment, the pluripotent cells are non-human embryonic stem cells, such as mouse stem cells, rodent stem cells or primate stem cells.

In one embodiment, the pluripotent cells are induced pluripotent stem cells (iPS). Induced pluripotent stem cells (iPS cells) are a type of pluripotent stem cells artificially derived from a non-pluripotent, typically an adult somatic cell, by inducing a "forced" expression of certain genes. iPS cells were first produced in 2006 from mouse cells (Takahashi and Yamanaka, 2006) and in 2007 from human cells (Takahashi et al., 2007; Yu et al., 2007).

In another embodiment, the activator of the canonical Wnt/ß-catenin signaling pathway or the Wnt/PCP signaling pathway according to the invention is a member of the R-spondin family, originating from a vertebrate species or modified.

In another embodiment, the member of the R-spondin family is a member of the mammalian R-spondin family.

In a particular embodiment, the member of the R-spondin family according to the invention is selected in the group consisting of R-spondin 1, R-spondin 2, R-spondin 3 and R-spondin 4.

In a particular embodiment, the member of the R-spondin family according to the invention is R-spondin 3.

In a particular embodiment, the member of the R-spondin family according to the invention is R-spondin 2.

As used herein, the term "R-spondin3" or "R-spondin2" refers to members of the family of secreted proteins in vertebrates that activate the Wnt signaling pathway.

An exemplary sequence for human R-spondin3 protein is deposited in the database under accession number NP_116173.2 (SEQ ID NO:1). An exemplary sequence for mouse R-spondin3 protein is deposited in the database under accession number NP_082627.3 (SEQ ID NO:2). An exemplary sequence for human R-spondin2 protein is deposited in the database under accession number NP_848660.3 (SEQ ID NO:3). An exemplary sequence for mouse R-spondin2 protein is deposited in the database under accession number NP_766403.1 (SEQ ID NO:4).

As used herein, the term "R-spondin3" also encompasses any functional variants of R-spondin3 wild type (naturally occurring) protein, provided that such functional variants retain the advantageous properties of differentiating factor for the purpose of the present invention. In one embodiment, said functional variants are functional homologues of R-spondin3 having at least 60%, 80%, 90% or at least 95% identity to the most closely related known natural R-spondin3 polypeptide sequence, for example, to human or mouse polypeptide R-spondin3 of SEQ ID NO:1 or SEQ ID NO:2 respectively, and retaining substantially the same Wnt activation activity as the related wild type protein. In another embodiment, said functional variants are fragments of R-spondin3, for example, comprising at least 50, 100, or 200 consecutive amino acids of a wild type R-spondin3 protein, and retaining substantially the same Wnt activation activity. In another embodiment, such functional variant can consist in R-spondin3 gene product isoforms such as the isoform 2 of the human R-spondin3 as described under the ref. Q9BXY4-2 and CAI20142.1 (SEQ ID NO:5).

As used herein, the term "R-spondin2" also encompasses any functional variants of R-spondin2 wild type (naturally occurring) protein, provided that such functional variants retain the advantageous properties of differentiating factor for the purpose of the present invention. In one embodiment, said functional variants are functional homologues of R-spondin2 having at least 60%, 80%, 90% or at least 95% identity to the most closely related known natural R-spondin2 polypeptide sequence, for example, to human or mouse polypeptide R-spondin2 of SEQ ID NO:3 or SEQ ID NO:4 respectively, and retaining substantially the same Wnt activation activity as the related wild type protein. In another embodiment, said functional variants are fragments of R-spondin2, for example, comprising at least 50, 100, or 200 consecutive amino acids of a wild type R-spondin2 protein, and retaining substantially the same Wnt activation activity. In another embodiment, said functional variants can consist in R-spondin2 gene product isoforms such as the isoform 2 or the isoform 3 of the human R-spondin2 such as described respectively under the ref. Q6UXX9-2 (SEQ ID NO:6) or under the ref. Q6UXX9-3 (SEQ ID NO:7).

As used herein, the percent identity between the two amino-acid sequences is a function of the number of identical positions shared by the sequences (i.e., % identity=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described below.

The percent identity between two amino-acid sequences can be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4.

In another embodiment, the activator according to the invention is a combination of the R-spondin 3 and R-spondin 2.

In another embodiment, the activator according to the invention may be the human R-spondin-3 isoform 2 of sequence SEQ ID NO:5.

In another embodiment, the activator according to the invention may be the human R-spondin-2 isoform 2 of sequence SEQ ID NO:6, or the human R-spondin-2 isoform 3 of sequence SEQ ID NO:7.

In a particular embodiment, the concentration of R-spondin3 used for culture of pluripotent cells is between 0.1 ng/ml and 500 ng/ml, preferably between 1 ng/ml and 500 ng/ml and more preferably between 5 ng/ml and 30 ng/ml.

In a particular embodiment, the concentration of R-spondin2 used for culture of pluripotent cells is between 1 ng/ml and 500 ng/ml, preferably between 5 ng/ml and 30 ng/ml.

In a particular embodiment, the concentration of R-spondin3 or R-spondin2 is 10 ng/ml. With a concentration of 10 ng/ml, more than 50% up to 70% of pluripotent cells are differentiated in induced Paraxial Mesoderm progenitor (iPAM) cells.

In another embodiment, pluripotent cells are cultured with R-spondin3 or R-spondin2 during 1 to 15 days, or for a shorter time period. In a particular embodiment, pluripotent cells are cultured with R-spondin3 or/and R-spondin2 during at least 10 days at a concentration of 10 ng/ml.

As used herein, the term "inhibitor of the BMP signaling pathway" denotes any compound, natural or synthetic, which results in a decreased activation of the BMP (bone morphogenetic protein) signaling pathway, which is characterized by the binding of a dimer BMP proteins to an heterocomplex constituted of BMP type I and type II receptors, which results in a phosphorylation cascade leading to the phosphorylation of Smad1/5/8, and resulting in target genes activation, such as Id genes. Typically, an inhibitor of the BMP signaling pathway provokes a decrease in the levels of phosphorylation of the proteins Smad 1, 5 and 8 (Gazzero and Minetti, 2007).

The skilled person in the art knows how to assess whether a given compound is an inhibitor of the BMP signaling pathway. Typically, a compound is deemed to be an inhibitor of the BMP signaling pathway if, after culturing cells in the presence of said compound, the level of phosphorylated Smad 1, 5 or 8 is decreased compared to cells cultured in the absence of said compound. Levels of phosphorylated Smad proteins can be measured by Western blot using antibodies specific for the phosphorylated form of said Smad proteins.

Target genes activation, such as Id genes, can typically be measured by direct Id1/2/3 transcripts (mRNA) production, via quantitative real-time PCR (qRT-PCR) and expression levels can be compared to control situation, in the absence of said compound.

The inhibitor of the BMP signaling pathway may be a BMP antagonist, a chemical compound that blocks BMP type I and/or type II receptors activity (BMP type I/II receptor inhibitor), an inhibitor of BMP type I and/or type II gene expression, or a molecule which inhibits any downstream step of the BMP signaling pathway. The inhibitor of BMP signaling may be a natural or a synthetic compound. When the inhibitor of the BMP signaling pathway is a protein, it may be a purified protein or a recombinant protein or a synthetic protein.

In one embodiment, the inhibitor of the BMP signaling pathway is a BMP type I receptors inhibitor.

Many methods for producing recombinant proteins are known in the art. The skilled person can readily, from the knowledge of a given protein's sequence or of the nucleotide sequence encoding said protein, produce said protein using standard molecular biology and biochemistry techniques.

In one embodiment of the invention, the inhibitor of the BMP signaling pathway is selected from the group consisting of Noggin, Chordin and related proteins (Chordin-like 1/2/3), Follistatin and related proteins (Follistatin-like 1/2/3/4/5), proteins of the Dan family (including Cerberus1, Gremlin 1 and 2, Cer1-2 (Coco), SOST (Sclerostin), SOSTDC1 (Wise)) and variants and fragments thereof which inhibit the BMP signaling pathway.

In another embodiment of the invention, the inhibitor of the BMP signaling pathway is selected from the group consisting of BMP-1/Tolloid-like proteins, TWSG1 (twisted gastrulation), TMEFFs (Tomoregulins), Biglycan, TSK (Tsukushi), BMPER (Crossveinless 2), Ogon (Sizzled), AMN (Amnionless), CTGF (Connective Tissue Growth Factor), and HSPGs (including Glypican3 and Syndecan4).

In another embodiment, the inhibitor of the BMP signaling pathway is noggin. Noggin can be murine (mouse noggin exemplified by GenPept accession number NP_032737, SEQ ID NO:10) or human noggin (human noggin exemplified by GenPept accession number EAW94528, SEQ ID NO:11). It may be purified or recombinant. It may be in monomeric or dimeric form.

In one embodiment, the inhibitor of the BMP signaling pathway is a compound that inhibits BMP signaling transduction cascade. In a particular embodiment, the compound that inhibits BMP signaling transduction cascade is a synthetic or a chemical compound.

In another embodiment, the inhibitor of the BMP signaling pathway is an inhibitor of BMP type I receptors.

As used herein, the term "BMP type I receptors" for "Bone Morphogenetic Protein" denotes transmembrane proteins with serine/threonine protein kinase activity that mediates the addition of phosphate molecules on certain serine and threonine amino acids on particular cellular substrates. It is well known in the art that an inhibitor of BMP type I receptors may block the BMP signaling pathway, see for example Yu et al, Nat Chem Biol. 2008.

In a preferred embodiment, the inhibitor of BMP type I receptors is Dorsomorphin, a chemical compound or any derivatives generated by structure-activity studies [Cuny G D et al., 2008]. Dorsomorphin (6-[4-(2-Piperidin-1-yl-ethoxy)phenyl]-3-pyridin-4-yl-pyrazolo [1,5-a]pyrimidine, also known as Compound C) is inhibiting specifically BMP type I receptors (ALK2, 3, and 6) [Yu P B et al., 2008].

Recombinant Noggin can be purchased from R&D Systems or Peprotech or can be produced using standard techniques as described above.

Typically, the inhibitor of the BMP signaling pathway is added to the culture medium of the invention in a concentration ranging from 1 to 10000 ng/ml, preferably from 5 to 1000 ng/ml, preferably from 5 to 500 ng/ml, preferably from 10 to 200 ng/ml, even more preferably at about 200 ng/ml.

Typically, noggin is added to the culture medium of the invention at a concentration ranging from 1 to 1000 ng/ml, preferably from 10 to 200 ng/ml, even more preferably at about 200 ng/ml.

Typically, Dorsomorphin is added to the culture medium of the invention in a concentration ranging from 0.1 to 2 µM, preferably at 1 µM.

In one embodiment, pluripotent cells are cultured with the inhibitor of the BMP signaling pathway during 1 to 4 days.

In one embodiment, the culture medium according to the invention comprises a Wnt activator and an inhibitor of BMP signaling pathway according to the invention to improve the differentiation of pluripotent cells into induced Paraxial Mesoderm progenitor (iPAM) cells.

In one embodiment, the Wnt activator is R-spondin3 and the inhibitor of BMP signaling pathway is Noggin.

In another embodiment, the culture medium according to the invention may further comprise DMSO (Dimethyl sulfoxide) or an equivalent of the DMSO to improve the differentiation of pluripotent cells into induced Paraxial Mesoderm progenitor (iPAM) cells.

As used herein, the term "equivalent" means a substance exhibiting the same properties as DMSO which is a solvent that dissolves both polar and nonpolar compounds.

In another embodiment, the culture medium according to the invention comprises R-spondin 3, Noggin and DMSO to improve the differentiation of pluripotent cells into induced Paraxial Mesoderm progenitor (iPAM) cells.

In another embodiment, the culture medium according to the invention comprises R-spondin 3 and DMSO to improve the differentiation of pluripotent cells into induced Paraxial Mesoderm progenitor (iPAM) cells.

In another embodiment, the culture medium according to the invention comprises R-spondin 2, Noggin and DMSO to improve the differentiation of pluripotent cells into induced Paraxial Mesoderm progenitor (iPAM) cells.

In another embodiment, the culture medium according to the invention comprises R-spondin 2 and DMSO to improve the differentiation of pluripotent cells into induced Paraxial Mesoderm progenitor (iPAM) cells.

In another embodiment, the culture medium according to the invention comprises R-spondin 3, Dorsomorphin and DMSO to improve the differentiation of pluripotent cells into induced Paraxial Mesoderm progenitor (iPAM) cells.

In another embodiment, the culture medium according to the invention comprises R-spondin 2, Dorsomorphin and DMSO to improve the differentiation of pluripotent cells into induced Paraxial Mesoderm progenitor (iPAM) cells.

In still another embodiment, the culture medium according to the invention comprises R-spondin 3, R-spondin 2, Noggin and DMSO to improve the differentiation of pluripotent cells into induced Paraxial Mesoderm progenitor (iPAM) cells.

In still another embodiment, the culture medium according to the invention comprises R-spondin 3, R-spondin 2 and DMSO to improve the differentiation of pluripotent cells into induced Paraxial Mesoderm progenitor (iPAM) cells.

In still another embodiment, the culture medium according to the invention comprises R-spondin 3, R-spondin 2, Dorsomorphin and DMSO to improve the differentiation of pluripotent cells into induced Paraxial Mesoderm progenitor (iPAM) cells.

Vertebrate recombinant R-spondins can be purchased commercially, or produced as conditioned culture medium. This involves expressing a construct containing the coding sequence of an R-spondin protein into competent cells, such as COS cells. R-spondin protein is secreted in the culture medium. Conditioned medium can be applied directly to pluripotent cells or prediluted in basal medium.

In another embodiment, the activator of the Wnt signaling pathway is an inhibitor of GSK-3β.

As used herein, the term "GSK-3 β" for "Glycogen synthase kinase 3 beta" denotes a serine/threonine protein kinase that mediates the addition of phosphate molecules on certain serine and threonine amino acids on particular cellular substrates. It is well known in the art that an inhibitor of GSK-3β may activate the Wnt signaling pathway, see for example (Cohen and Goedert, 2004; Sato et al., 2004; Taelman et al., 2010; Wu and Pan, 2010).

In a preferred embodiment, the inhibitor of GSK-3β is CHIR99021.

In another preferred embodiment, the following alternatives may be used for increasing the activity of R-spondin factor in the system:
1. enhancing endogenous expression of the gene encoding said R-spondin factor or a modified form of R-spondin,
2. allowing ectopic expression of said R-spondin factor by introducing an expression vector comprising a coding sequence of R-spondin factor operably linked to control sequences into the pluripotent cells to be differentiated, or by introducing in the cells coding RNA for R-spondin factor
3. introducing directly into the cells environment an appropriate amount of R-spondin factor, for example as recombinant R-spondin factor (family of R-spondin1, 2, 3 and 4) in the culture medium, or conditioned medium, or as substrate coating.
4. activating or inhibiting endogeneous expression of a gene involved in R-spondin factor signaling in said target cells; or,
5. overexpressing proteins involved in controlling R-spondin factor expression level, maturation and overall regulation in said target cells.

In one embodiment, the culture medium according to the invention comprises CHIR99021 and an inhibitor of BMP signaling pathway according to the invention which is Dorsomorphin to improve the differentiation of pluripotent cells into induced Paraxial Mesoderm progenitor (iPAM) cells.

In one embodiment, the culture medium according to the invention comprises CHIR99021, Dorsomorphin and DMSO to improve the differentiation of pluripotent cells into induced Paraxial Mesoderm progenitor (iPAM) cells.

In one embodiment, the culture medium according to the invention comprises a Wnt activator which is a combination of R-spondin2, R-spondin3 and CHIR99021; and an inhibitor of BMP signaling according to the invention which is a combination of Noggin and Dorsomorphin to improve the differentiation of pluripotent cells into induced Paraxial Mesoderm progenitor (iPAM) cells.

In still another embodiment, the culture medium according to the invention comprises R-spondin 3, R-spondin 2, CHIR99021, Dorsomorphin and DMSO to improve the differentiation of pluripotent cells into induced Paraxial Mesoderm progenitor (iPAM) cells.

In still another embodiment, the culture medium according to the invention comprises R-spondin 3, R-spondin 2, CHIR99021, Noggin and DMSO to improve the differentiation of pluripotent cells into induced Paraxial Mesoderm progenitor (iPAM) cells.

In another embodiment, introducing directly into the cells environment an appropriate amount of pharmacological GSK-3β inhibitor, for example the chemical compound CHIR99021 is used as an alternative for increasing the activity of Wnt signaling pathway in the system, alone or in combination with R-spondin.

The invention relates to a composition for preparing induced Paraxial Mesoderm progenitor (iPAM) cells from pluripotent cells wherein said composition comprises an effective amount of an activator of the Wnt signaling pathway according to the invention and an effective amount of an inhibitor of the Bone Morphogenetic Protein (BMP) signaling pathway.

The invention also relates to a composition for preparing induced Paraxial Mesoderm progenitor (iPAM) cells from pluripotent cells wherein said composition comprises an effective amount of an activator of the Wnt signaling pathway according to the invention.

The invention also relates to a kit for preparing induced Paraxial Mesoderm progenitor (iPAM) cells, said kit comprising:
 a) an activator of the Wnt signaling pathway
 b) an inhibitor of the Bone Morphogenetic Protein (BMP) signaling pathway.
 c) optionally, instructions for preparing induced Paraxial Mesoderm progenitor (iPAM) cells.

The invention also relates to a kit for preparing induced Paraxial Mesoderm progenitor (iPAM) cells, said kit comprising:
 a) an activator of the Wnt signaling pathway
 b) optionally, instructions for preparing induced Paraxial Mesoderm progenitor (iPAM) cells.

In a preferred embodiment, the activator is a member of the R-spondin family.

In another embodiment, the activator is selected from the group consisting of R-spondin 1, R-spondin 2, R-spondin 3 and R-spondin 4.

In another preferred embodiment, the activator is the R-spondin 2 or the R-spondin 3.

In another preferred embodiment, the activator is an inhibitor of GSK-3β such as CHIR99021.

In another embodiment, the inhibitor according to the invention is a secreted antagonist of the BMP/TGFbeta family.

In another embodiment, the inhibitor of BMP signaling pathway is selected from the group consisting of Noggin, Chordin, Chordin-like 1/2/3, Follistatin, Follistatin-like 1/2/3/4/5, a member of the Dan family, including Cerberus 1, Gremlin 1/2.

In another preferred embodiment, the inhibitor is Noggin or Follistatin.

In another preferred embodiment, the inhibitor is a chemical inhibitor of BMP signaling such as Dorsomorphin.

In a specific embodiment, said kit for preparing induced Paraxial Mesoderm progenitor (iPAM) cells comprises,
 a) a composition comprising members of the R-spondin family;
 b) a composition comprising an inhibitor of the BMP signaling pathway and
 c) DMSO or an equivalent.

In another specific embodiment, said kit for preparing induced Paraxial Mesoderm progenitor (iPAM) cells comprises,
 a) a composition comprising members of the R-spondin family;
 b) DMSO or an equivalent.

In a specific embodiment, said kit for preparing induced Paraxial Mesoderm progenitor (iPAM) cells comprises,
 a) a composition comprising a chemical compound inhibitor of GSK-3β;
 b) a composition comprising a chemical compound inhibitor of BMP type I receptors and
 c) DMSO or an equivalent.

Populations Comprising Induced Paraxial Mesoderm Progenitor (iPAM) Cells Obtainable from the Methods of the Invention The invention further relates to populations comprising induced Paraxial Mesoderm progenitor (iPAM) cells obtainable from the method as described above.

These populations typically may comprise other cell types in addition to induced Paraxial Mesoderm progenitor (iPAM) cells. In one embodiment, the populations of the invention are characterized in that they comprise at least 10%, 20%, 30%, 40%, 50%, 60%, 70%, 80% and preferably at least 90% of cells that exhibit high expression of at least one biomarker characteristic of paraxial mesoderm progenitor cells, for example Msgn1 gene product.

Other biomarkers characteristic of paraxial mesoderm progenitor cells include, without limitation, one or more of the following proteins: Tbx6, EphrinA1, EphrinB2, EPHA4, PDGFRalpha, Sall1, Sall4, Dll1, Dll3, Papc (Pcdh8), Lfng, Hes7, Ripply1, Ripply2, Brachyury (T), Cdx2, Cdx4, Evx1, Cxcr4, Il17rd, Fgf8, Fgf17, Gbx2, Wnt3a, Wnt5b, Rspo3, SP5, SP8, Has2, Dkk1, Dact1, Pax3, Pax7, Mesp1, Mesp2.

Any methods known in the art for measuring gene expression may be used, in particular, quantitative methods such as, real time quantitative PCR or microarrays, or methods using gene reporter expression, said gene reporter comprising Msgn1 promoter as described in the Examples, or qualitative methods such as immunostaining or cell sorting methods identifying cells exhibiting specific biomarkers, including cell surface markers.

As used herein, the Msgn1 gene refers to the gene encoding Mesogenin1. Examples of a nucleotide sequence of a gene encoding Mesogenin1 in mouse and human are given in SEQ ID NO:8 (NM_019544.1) and SEQ ID NO:9 (NM_001105569.1) respectively.

In one embodiment, expression of Msgn1 is considered high if expression is detectable in a quantitative assay for gene expression. In another embodiment, it is high if the expression level is significantly higher than the expression level observed in the original pluripotent cells, or in cells differentiating under non specific conditions such as Basal culture medium without LIF (Leukemia Inhibitory Factor) for mouse pluripotent cells or without FGF (Fibroblast Growth Factor) for human pluripotent cells. Expression levels between the control and the test cells may be normalized using constitutively expressed genes such as GAPDH or Beta Actin.

Populations comprising induced Paraxial Mesoderm progenitor (iPAM) cells may be cultured indefinitely under appropriate growth conditions. Appropriate growth conditions may be established by the skilled person in the art based on established growth conditions for embryonic stem cells or induced pluripotent stem cells (iPS cells) for example or as described in the Examples below. Growth conditions may advantageously comprise for example the use of serum replacement medium, KSR (Gibco), ESGRO (Chemicon/Millipore) supplemented with growth factors like FGFs, WNTs, or chemical compounds modulating the respective signaling pathways.

The induced Paraxial Mesoderm progenitor (iPAM) cells may be purified or the populations may be enriched in induced Paraxial Mesoderm progenitor (iPAM) cells by selecting cells expressing markers specific of induced Paraxial Mesoderm progenitor (iPAM) cells. In one embodiment, markers specific of induced Paraxial Mesoderm progenitor (iPAM) cells for purification or enrichment of a population of induced Paraxial Mesoderm progenitor (iPAM) cells may be selected among one or more of the following markers: Msgn1, Tbx6, EphrinA1, EphrinB2, EPHA4, PDGFRalpha, Sall1, Sall4, Dll1, Dll3, Papc (Pcdh8), Lfng, Hes7, Ripply1, Ripply2, Brachyury (T), Cdx2, Cdx4, Evx1, Cxcr4, Il17rd, Fgf8, Fgf17, Gbx2, Wnt3a, Wnt5b, Rspo3, SP5, SP8, Has2, Dkk1, Dact1, Pax3, Pax7, Mesp1, Mesp2, or selected negatively with markers of other lineages/cell type such as neural fate.

Purification or induced Paraxial Mesoderm progenitor (iPAM) cells enrichment may be achieved using cell sorting technologies, such as fluorescence activated cell sorting (FACS) or magnetic beads comprising specific binders of said cell surface markers of induced Paraxial Mesoderm progenitor (iPAM) cells, or fluorescent reporters for paraxial mesoderm progenitor markers. Another method consists in taking advantage of the differential adhesion properties of induced Paraxial Mesoderm progenitor (iPAM) cells, by selective attachment on defined substrates.

After purification or enrichment, the population may thus comprise more than 10%, 20%, 30%, 40%, 50%, 60%; 70%, 80%, 90% or more than 95% of cells having a high expression of a biomarker characteristic of induced Paraxial Mesoderm progenitor (iPAM) cells, for example, Msgn1 gene product.

In another preferred embodiment, the invention relates to a composition comprising a population of induced Paraxial Mesoderm progenitor (iPAM) cells obtainable from the method as described above.

Methods for Preparing Cell Lineages by Differentiation of Induced Paraxial Mesoderm Progenitor (iPAM) Cells The induced Paraxial Mesoderm progenitor (iPAM) cells may advantageously be cultured in vitro under differentiation conditions to generate skeletal muscle, bone, cartilage, dermal cells, as well as other derivatives of the paraxial mesoderm including but not restricted to adipocytes or endothelial cells.

Thus, the invention relates to a method for preparing populations comprising skeletal muscle, bone, cartilage, dermal cell, adipocytes or endothelial cells lineages said method comprising the steps of (a) providing a population comprising induced Paraxial Mesoderm progenitor (iPAM) cells; and, (b) culturing said population comprising induced Paraxial Mesoderm progenitor (iPAM) cells, under appropriate conditions for their differentiation into the desired cell lineages selected among the paraxial mesoderm derivatives which include skeletal muscle, bone, cartilage, dermal cell, adipocyte or endothelial cell lineages.

The invention further relates to a composition for preparing populations of cell lineages comprising induced Paraxial Mesoderm progenitor (iPAM) cells according to the invention and appropriate conditions for their differentiation into the desired cell lineages.

In one specific embodiment, the present invention provides a method for preparing a population comprising skeletal muscle cell lineages, said method comprising the steps of (a) providing a population comprising induced Paraxial Mesoderm progenitor (iPAM) cells;

(b) culturing said population comprising induced Paraxial Mesoderm progenitor (iPAM) cells in the presence of a differentiation medium comprising at least the following components:
  (i) an extracellular matrix material; and,
  (ii) compounds activating or inhibiting the signaling pathways known to control of the differentiation of said lineages which include but are not restricted to retinoic acid, BMP, TGFß (Transforming Growth Factorß), Hedgehog, Notch, FGF, Wnt, myostatin, insulin, PDGF, VEGF, MAPK, PI3K; and, (c) optionally, culturing said population obtained from step (b) in a second differentiation medium comprising at least one or more compounds activating or inhibiting the Wnt, FGF, HGF (Hepatocyte growth factor), Activin, EGF (Epidermal growth factor), insulin, and IGF signaling pathways or compounds known to promote myogenic differentiation such as horse serum or transferrin, thereby obtaining a population comprising skeletal muscle cell lineages, that can be identified by markers such as Desmin, or Myosin Heavy Chain.

The use of engineered extracellular matrices or three dimensional scaffolds has been widely described in the Art (Metallo et al., 2007). In specific embodiments, the extracellular matrix material is selected from the group consisting of Collagen I, Collagen IV, Fibronectin, Laminin, gelatin, poly-lysine, PDMS and Matrigel.

The invention further relates to a composition for preparing skeletal muscle cell lineages from induced Paraxial Mesoderm progenitor (iPAM) cells, characterized in that it further comprises:
  i. an extracellular matrix material,
  ii. at least one or more compounds activating or inhibiting the retinoic acid, BMP (Bone morphogenetic protein), TGFß, Hedgehog, Notch, FGF, Wnt, myostatin, insulin, PDGF (Platelet derived growth factor), VEGF (Vascular endothelial growth factor), MAPK, PI3K pathways. The composition further comprises at least another compound activating or inhibiting the Wnt, FGF, HGF, Activin, EGF, insulin, and IGF signaling pathways or compounds known to promote myogenic differentiation such as horse serum or transferrin.

In another embodiment, the present invention provides a method for preparing a population comprising dermal cell lineages, said method comprising the steps of culturing a population comprising induced Paraxial Mesoderm progenitor (iPAM) cells in the presence of an efficient amount of at least one or more compounds activating or inhibiting BMP, TGFß, Wnt, FGF, EGF, retinoic acid, Notch and Hedgehog pathways. Dermal cells can be identified using markers such as Dermo-1.

The invention further relates to a composition for preparing dermal cell lineages from induced Paraxial Mesoderm progenitor (iPAM) cells, characterized in that it further comprises at least one or more compounds activating or inhibiting BMP, TGFß, Wnt, FGF, EGF, retinoic acid, Notch and Hedgehog pathways.

In another specific embodiment, the present invention provides a method for preparing a population comprising bone or cartilage cell lineages, comprising the step of culturing a population comprising induced Paraxial Mesoderm progenitor (iPAM) cells in the presence of an efficient amount of at least one or more compounds activating or inhibiting the retinoic acid, Wnt, Hedgehog, PTHrP, TGFß, BMP pathways, or compounds known to promote bone or cartilage differentiation such as dexamethasone, ascorbic acid, vitamin D3, and beta-glycerophosphate. Cartilage cells can be identified by classical staining such as Alcian Blue and bone cells with alizarin red or Von Kossa stain.

The invention further relates to a composition for preparing bone or cartilage cell lineages from induced Paraxial Mesoderm progenitor (iPAM) cells, characterized in that it further comprises at least one or more compounds activating or inhibiting retinoic acid, Wnt, Hedgehog, PTHrP, TGFß, BMP pathways, or compounds known to promote bone or cartilage differentiation such as dexamethasone, ascorbic acid, vitamin D3 and beta-glycerophosphate.

In yet another embodiment, the present invention provides a method for preparing a population comprising adipocytes, said method comprising the steps of culturing the population comprising induced Paraxial Mesoderm progenitor (iPAM) cells in the presence of an efficient amount of at least one or more compounds known to promote adipocyte differentiation including dexamethasone, isobutylxanthine and insulin. Adipocytes can be detected by OilRedO staining.

The invention further relates to a composition for preparing adipocytes from induced Paraxial Mesoderm progenitor (iPAM) cells, characterized in that it further comprises at least one compound known to promote adipocyte differentiation including dexamethasone, isobutylxanthine and insulin.

In yet another embodiment, the present invention provides a method for preparing a population comprising endothelial cells, said method comprising the steps of culturing the population comprising induced Paraxial Mesoderm progenitor (iPAM) cells in the presence of an efficient amount of at least one or more compounds activating or inhibiting the VEGF or FGF pathways. Endothelium can be detected by PECAM-1 (CD31) immunostaining.

The invention further relates to a composition for preparing endothelial cells from induced Paraxial Mesoderm progenitor (iPAM) cells, characterized in that it further comprises at least one or more compounds activating or inhibiting the VEGF or FGF pathways.

Several examples of suitable conditions for differentiating induced Paraxial Mesoderm progenitor (iPAM) cells into cartilage, muscles or endothelial cells are described in Examples below.

In another embodiment, the present invention provides populations comprising skeletal muscle, bone, cartilage, dermal cell, adipocytes or endothelial cells lineages as well as other derivatives derived from induced Paraxial Mesoderm progenitor (iPAM) cells.

In a preferred embodiment, the present invention provides populations comprising skeletal muscle, bone, cartilage, dermal cell, adipocytes or endothelial cells lineages as well as other derivatives derived from induced Paraxial Mesoderm progenitor (iPAM) cells obtained with a composition according to the invention.

In another embodiment, the invention relates to a composition comprising skeletal muscle, bone, cartilage, dermal cell, adipocyte or endothelial cell lineages obtainable by a method according to the invention.

iPAM Cells, Population of Cells Derived from iPAM Cells and Uses Thereof

Another aspect of the invention relates to the use of said populations comprising induced Paraxial Mesoderm progenitor (iPAM) cells, or said populations comprising skeletal muscle, bone, cartilage or dermal cell lineages derived from differentiation of induced Paraxial Mesoderm progenitor (iPAM) cells, but also adipose tissue and endothelial paraxial mesoderm derivatives, hereafter referred as the Populations of the Invention.

The Populations of the Invention may be used in a variety of applications, in particular, in research or therapeutic field.

One major field of application is cell therapy or regenerative medicine. For example, cells obtained from a patient suffering from a genetic defect may be cultured and genetically corrected according to methods known in the art, and subsequently reprogrammed into iPS cells and differentiated into induced Paraxial Mesoderm progenitor (iPAM) cells or its derivatives for re-administration into the patient.

Similarly, regenerative medicine can be used to potentially cure any disease that results from malfunctioning, damaged or failing tissue by either regenerating the damaged tissues in vivo by direct in vivo implantation of a population comprising induced Paraxial Mesoderm progenitor (iPAM) cells or their derivatives comprising appropriate progenitors or cell lineages.

Therefore, in one aspect, the invention relates to the induced Paraxial Mesoderm progenitor (iPAM) cells or their derivatives or the Populations of the Invention for use as a cell therapy product for implanting into a mammal, for example human patient.

In one specific embodiment, the invention relates to a pharmaceutical composition comprising a population of induced Paraxial Mesoderm progenitor (iPAM) cells obtained according to the invention. In another preferred embodiment, the invention relates to a pharmaceutical composition comprising a population of induced Paraxial Mesoderm progenitor (iPAM) cells including for example at least $10^2$, $10^3$, $10^4$, $10^5$, $10^6$, $10^7$, $10^8$, or at least $10^9$ Msgn1 expressing cells. In another embodiment, this composition comprises a pharmaceutically acceptable vehicle.

In one specific embodiment, the Populations of the Invention are used for the treatment of a muscle genetic disorder, for example Duchenne muscular dystrophy, or any other genetic muscular dystrophy.

In an embodiment, induced Paraxial Mesoderm progenitor (iPAM) cells are co-cultured with various cell types to induce their differentiation toward the desired lineage. In another embodiment, induced Paraxial Mesoderm progenitor (iPAM) cells are directly grafted into a recipient host. For regenerative medicine purposes, induced Paraxial Mesoderm progenitor (iPAM) cells can be grafted after genetic correction by methods known in the art.

In another specific embodiment, the Populations of the Invention are used in orthopaedic surgery for the treatment of joint or cartilage or bone damages caused by aging, disease, or by physical stress such as occurs through injury or repetitive strain.

In another specific embodiment, the Populations of the Invention may also be used advantageously for the production of dermal tissues, for example, skin tissues, for use in regenerative medicine or in research, in particular in the cosmetic industry or for treatment of burns and plastic surgery.

In another preferred embodiment, the invention relates to a composition comprising the Populations of the Invention. The composition comprising the Population of the invention may be used in cell therapy or regenerative medicine.

The invention will be further illustrated by the following figures and examples. However, these examples and figures should not be interpreted in any way as limiting the scope of the present invention.

FIGURES AND TABLES

TABLE 1

Sequences of the invention

| Proteins | Bank Reference number | SEQ ID | Sequences |
|---|---|---|---|
| hRspondin3 | NP-116173.2 (CAI20141.1) or Q9BXY4-1 | SEQ ID NO: 1 | MHLRLISWLF IILNFMEYIG SQNASRGRRQ RRMHPNVSQG CQGGCATCSD YNGCLSCKPR LFFALERIGM KQIGVCLSSC PSGYYGTRYP DINKCTKCKA DCDTCFNKNF CTKCKSGFYL HLGKCLDNCP EGLEANNHTM ECVSIVHCEV SEWNPWSPCT KKGKTCGFKR GTETRVREII QHPSAKGNLC PPTNETRKCT VQRKKCQKGE RGKKGRERKR KKPNKGESKE AIPDSKSLES SKEIPEQREN KQQQKKRKVQ DKQKSVSVST VH |
| mRspondin3 | NP-082627.3 | SEQ ID NO: 2 | MHLRLISCFF IILNFMEYIG SQNASRGRRQ RRMHPNVSQG CQGGCATCSD YNGCLSCKPR LFFVLERIGM KQIGVCLSSC PSGYYGTRYP DINKCTKCKV DCDTCFNKNF CTKCKSGFYL HLGKCLDSCP EGLEANNHTM ECVSIVHCEA SEWSPWSPCM KKGKTCGFKR GTETRVRDIL QHPSAKGNLC PPTSETRTCI VQRKKCSKGE RGKKGRERKR KKLNKEERKE TSSSSDSKGL ESSIETPDQQ ENKERQQQQK RRARDKQQKS VSVSTVH |
| hRspondin2 | NP-848660.3 or Q6UXX9-1 | SEQ ID NO: 3 | MQFRLFSFAL IILNCMDYSH CQGNRWRRSK RASYVSNPIC KGCLSCSKDN GCSRCQQKLF FFLRREGMRQ YGECLHSCPS GYYGHRAPDM NRCARCRIEN CDSCFSKDFC TKCKVGFYLH RGRCFDECPD GFAPLEETME CVEGCEVGHW SEWGTCSRNN RTCGFKWGLE TRTRQIVKKP VKDTILCPTI AESRRCKMTM RHCPGGKRTP KAKEKRNKKK KRKLIERAQE QHSVFLATDR ANQ |
| mRspondin2 | NP-766403.1 | SEQ ID NO: 4 | MRFCLFSFAL IILNCMDYSQ CQGNRWRRNK RASYVSNPIC KGCLSCSKDN GCSRCQQKLF FFLRREGMRQ YGECLHSCPS GYYGHRAPDM NRCARCRIEN CDSCFSKDFC TKCKVGFYLH RGRCFDECPD GFAPLDETME CVEGCEVGHW SEWGTCSRNN RTCGFKWGLE TRTRQIVKKP AKDTIPCPTI AESRRCKMAM RHCPGGKRTP KAKEKRNKKK RRKLIERAQE QHSVFLATDR VNQ |
| hRspondin3 isoform2 | CAI20142.1 or Q9BXY4-2 | SEQ ID NO: 5 | MHLRLISWLF IILNFMEYIG SQNASRGRRQ RRMHPNVSQG CQGGCATCSD YNGCLSCKPR LFFALERIGM KQIGVCLSSC PSGYYGTRYP DINKCTKCKA DCDTCFNKNF CTKCKSGFYL HLGKCLDNCP EGLEANNHTM ECVSIVHCEV SEWNPWSPCT KKGKTCGFKR GTETRVREII QHPSAKGNLC PPTNETRKCT VQRKKCQKGE RGKKGRERKR KKPNKGESKE AIPDSKSLES SKEIPEQREN KQQQKKRKVQ DKQKSGIEVT LAEGLTSVSQ RTQPTPCRRR YL |
| hRspondin2 isoform2 | Q6UXX9.2 | SEQ ID NO: 6 | MRQYGECLHS CPSGYYGHRA PDMNRCARCR IENCDSCFSK DFCTKCKVGF YLHRGRCFDE CPDGFAPLEE TMECVEGCEV GHWSEWGTCS RNNRTCGFKW GLETRTRQIV KKPVKDTILC PTIAESRRCK MTMRHCPGGK RTPKAKEKRN KKKKRKLIER AQEQHSVFLA TDRANQ |

TABLE 1-continued

Sequences of the invention

| Proteins | Bank Reference number | SEQ ID | Sequences |
|---|---|---|---|
| hRspondin2 isoform3 | Q6UXX9-3 | SEQ ID NO: 7 | FRLFSFAL IILNCMDYSH CQGNRWRRSK RGCRIENCDS CFSKDFCTKC KVGFYLHRGR CFDECPDGFA PLEETMECVG CEVGHWSEWG TCSRNNRTCG FKWGLETRTR QIVKKPVKDT ILCPTIAESR RCKMTMRHCP GGKRTPKAKE KRNKKKKRKL IERAQEQHSV FLATDRANQ |
| mMsgn1 | NM.019544.1 | SEQ ID NO: 8 | ATGGACAACC TGGGTGAGAC CTTCCTCAGC CTGGAGGATG GCCTGGACTC TTCTGACACC GCTGGTCTGC TGGCCTCCTG GGACTGGAAA AGCAGAGCCA GGCCCTTGGA GCTGGTCCAG GAGTCCCCCA CTCAAAGCCT CTCCCCAGCT CCTTCTCTGG AGTCCTACTC TGAGGTCGCA CTGCCCTGCG GGCACAGTGG GGCCAGCACA GGAGGCAGCG ATGGCTACGG CAGTCACGAG GCTGCCGGCT TAGTCGAGCT GGATTACAGC ATGTTGGCTT TTCAACCTCC CTATCTACAC ACTGCTGGTG GCCTCAAAGG CCAGAAAGGC AGCAAAGTCA AGATGTCTGT CCAGCGGAGA CGGAAGGCCA GCGAGAGAGA GAAACTCAGG ATGCGGACCT TAGCCGATGC CCTCCACACG CTCCGGAATT ACCTGCCGCC TGTCTACAGC CAGAGAGGCC AACCGCTCAC CAAGATCCAG ACACTCAAGT ACACCATCAA GTACATCGGG GAACTCACAG ACCTCCTCAA CAGCAGCGGG AGAGAGCCCA GGCCACAGAG TGTGTGA |
| hMsgn1 | NM001105569.1 | SEQ ID NO: 9 | ATGGACAACC TGCGCGAGAC TTTCCTCAGC CTCGAGGATG GCTTGGGCTC CTCTGACAGC CCTGGCCTGC TGTCTTCCTG GGACTGGAAG GACAGGGCAG GGCCCTTTGA GCTGAATCAG GCCTCCCCCT CTCAGAGCCT TTCCCCGGCT CCATCGCTGG AATCCTATTC TTCTTCTCCC TGTCCAGCTG TGGCTGGGCT GCCCTGTGAG CACGGCGGGG CCAGCAGTGG GGGCAGCGAA GGCTGCAGTG TCGGTGGGGC CAGTGGCCTG GTAGAGGTGG ACTACAATAT GTTAGCTTTC CAGCCCACCC ACCTTCAGGG CGGTGGTGGC CCCAAGGCCC AGAAGGGCAC CAAAGTCAGG ATGTCTGTCC AGCGGAGGCG GAAAGCCAGC GAGAGGGAGA AGCTCAGGAT GAGGACCTTG GCAGATGCCC TGCACACCCT CCGGAATTAC CTGCCACCTG TCTACAGCCA GAGAGGCCAG CCTCTCACCA AGATCCAGAC ACTCAAGTAC ACCATCAAGT ACATCGGGGA ACTCACAGAC CTCCTTAACC GCGGCAGAGA GCCCAGAGCC CAGAGCGCGT GA |
| mNoggin | NP_032737 | SEQ ID NO: 10 | MERCPSLGVT LYALVVVLGL RAAPAGGQHY LHIRPAPSDN LPLVDLIEHP DPIFDPKEKD LNETLLRSLL GGHYDPGFMA TSPPEDRPGG GGGPAGGAED LAELDQLLRQ RPSGAMPSEI KGLEFSEGLA QGKKQRLSKK LRRKLQMWLW SQTFCPVLYA WNDLGSRFWP RYVKVGSCFS KRSCSVPEGM VCKPSKSVHL TVLRWRCQRR GGQRCGWIPI QYPIISECKC SC |
| hNoggin | EAW94528 | SEQ ID NO: 11 | MERCPSLGVT LYALVVVLGL RATPAGGQHY LHIRPAPSDN LPLVDLIEHP DPIFDPKEKD LNETLLRSLL GGHYDPGFMA TSPPEDRPGG GGGAAGGAED LAELDQLLRQ RPSGAMPSEI KGLEFSEGLA QGKKQRLSKK LRRKLQMWLW SQTFCPVLYA WNDLGSRFWP RYVKVGSCFS KRSCSVPEGM VCKPSKSVHL TVLRWRCQRR GGQRCGWIPI QYPIISECKC SC |

FIG. 1: R-spondin induces induced Paraxial Mesoderm progenitor (iPAM) cells fate.

(A) Comparison of fluorescent Msgn1 Reporter activation (YFP positive cells (YFP+ cells)) after 4 days of differentiation of mES cells (Msgn1RepV), under default culture conditions in 15% FBS or 15% KSR medium, with or without recombinant mouse Rspo3 (10 ng/mL). YFP channel, 50×. (B) Robustness of iPAM cells induction in response to mouse Rspo3 in 15% FBS medium. Triplicate wells measurements by flow cytometry. Error bar is s.e.m.

FIG. 2: Flow-cytometry analysis of the induction of the Msgn1-YFP+ (induced Paraxial Mesoderm progenitor (iPAM) cells) population upon treatment with Rspo3.

(A) Flow-cytometry analysis on the Msgn1RepV mES cells at day 0 of differentiation in 15% FBS medium. YFP+ population represents less than 1%. (B) Flow-cytometry analysis at day 4 of differentiation in 15% FBS medium supplemented with R-spondin3 10 ng/mL. YFP+ population represents more than 70% of the total population.

FIG. 3: Paraxial mesoderm progenitors (induced Paraxial Mesoderm progenitor (iPAM) cells) characterization.

(A) Differentiation of mouse Msgn1RepV reporter mES cells into iPAM cells after 4 days in culture labeled with an anti-YFP antibody and co-stained with Hoechst, ×10. (B) qRT-PCR analysis of FACS sorted iPAM YFP positive population for the paraxial mesoderm progenitors specific genes Msgn1 and Tbx6, relative expression normalized to non iPAM YFP negative population expression level (fold enrichment).

Figure 4:
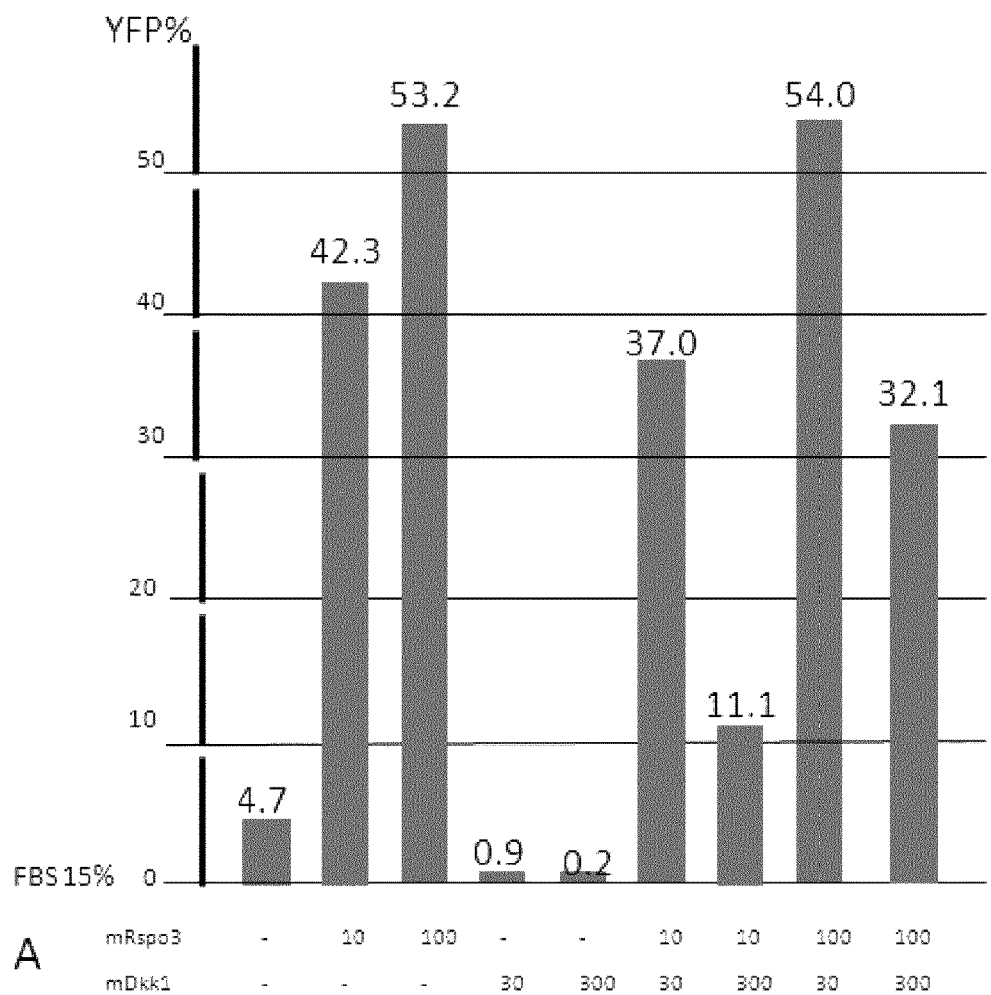
Figure 4:
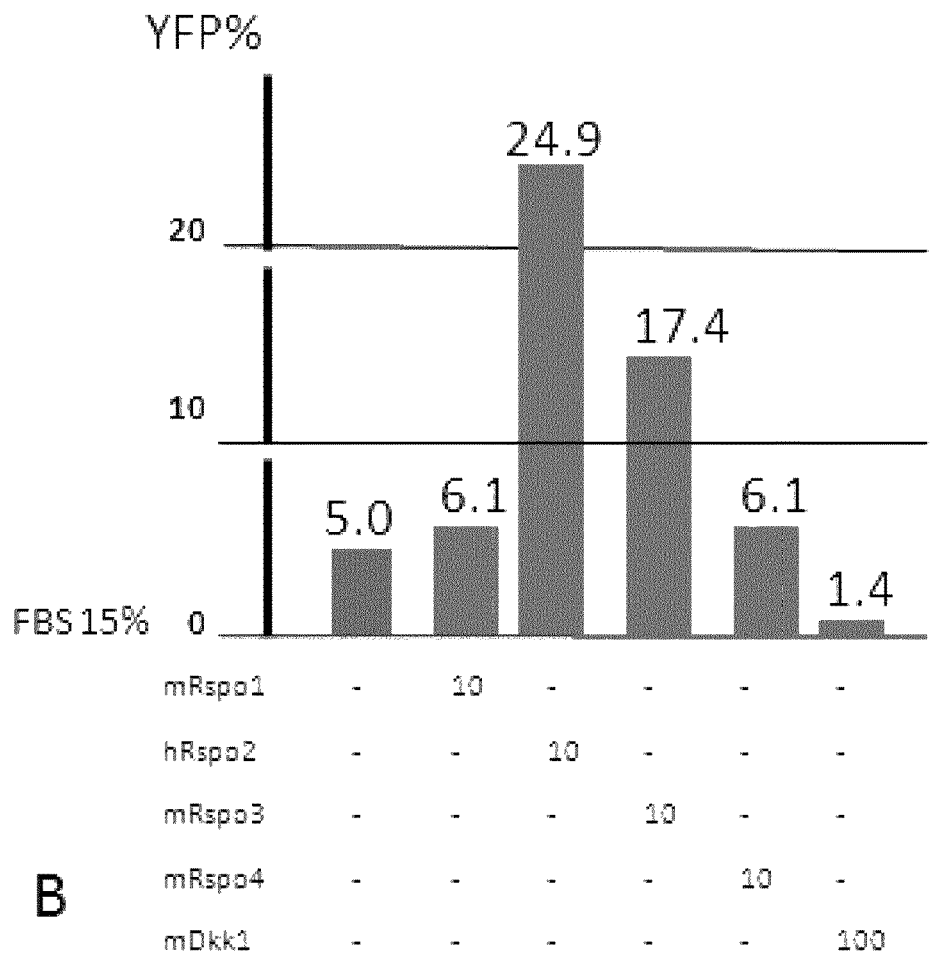
Figure 4:
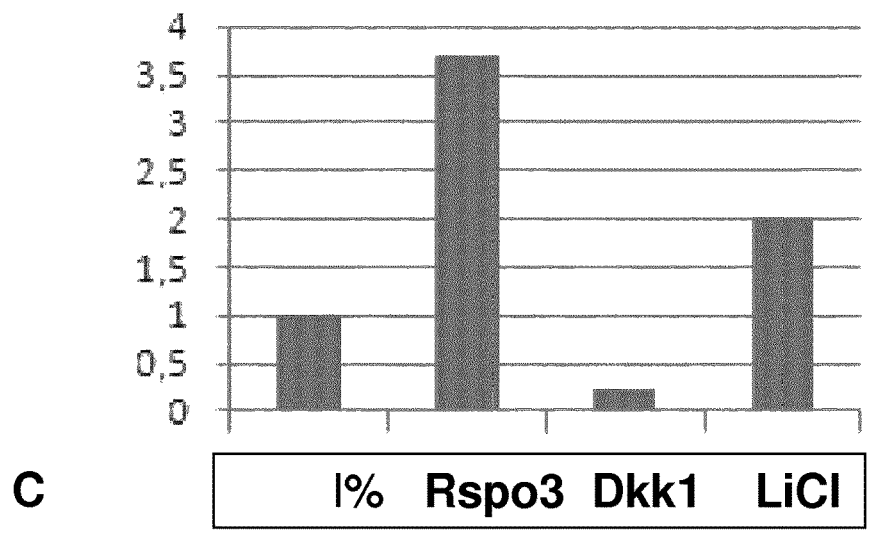

FIG. 4: R-spondin activity in induced Paraxial Mesoderm progenitor (iPAM) cells mediated by canonical Wnt signaling.

(A) Comparison of the effect of different doses of Rspo3 on iPAM induction (% YFP positive cells) after 4 days of differentiation in 15% FBS medium in the presence or absence of the canonical Wnt inhibitor Dkk1. Concentrations in ng/mL. (B) Comparison of the efficiency of the four recombinant Rspo family members on iPAM induction (% YFP positive cells) after 4 days in differentiation in 15% FBS medium. Concentrations in ng/mL. (C) Luciferase detection in Msgn1RepV reporter mES cells transfected with a Batluc reporter construct for canonical Wnt signaling activation and cultured in the presence of Rspo3 (10 ng/mL), Dkk1 (50 ng/mL) and LiCl (5 mM) in low serum (1% FBS) containing medium. Treatment with Rspo3 strongly activates the canonical Wnt response in differentiating ES cells.

Figure 5:
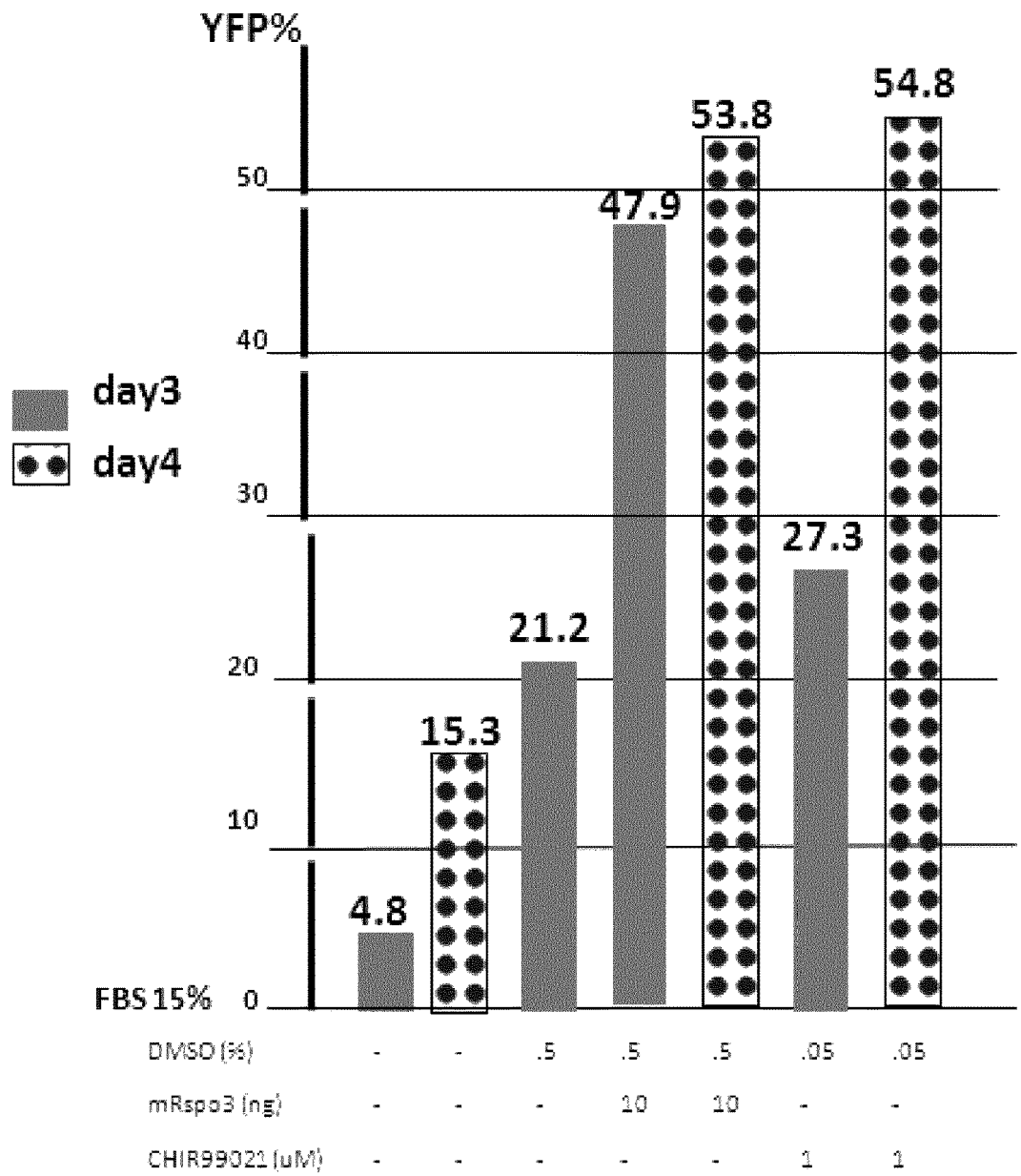

FIG. 5: R-spondin activity can be mimicked by the GSK3beta inhibitor CHIR99021.

Comparison of the efficiency of Rspo3 and CHIR99021 on iPAM induction (% YFP positive cells) after 3 and 4 days in differentiation 15% FBS medium. Concentrations are in ng/mL for Rspo3 or in µM for CHIR99021.

Figure 6:
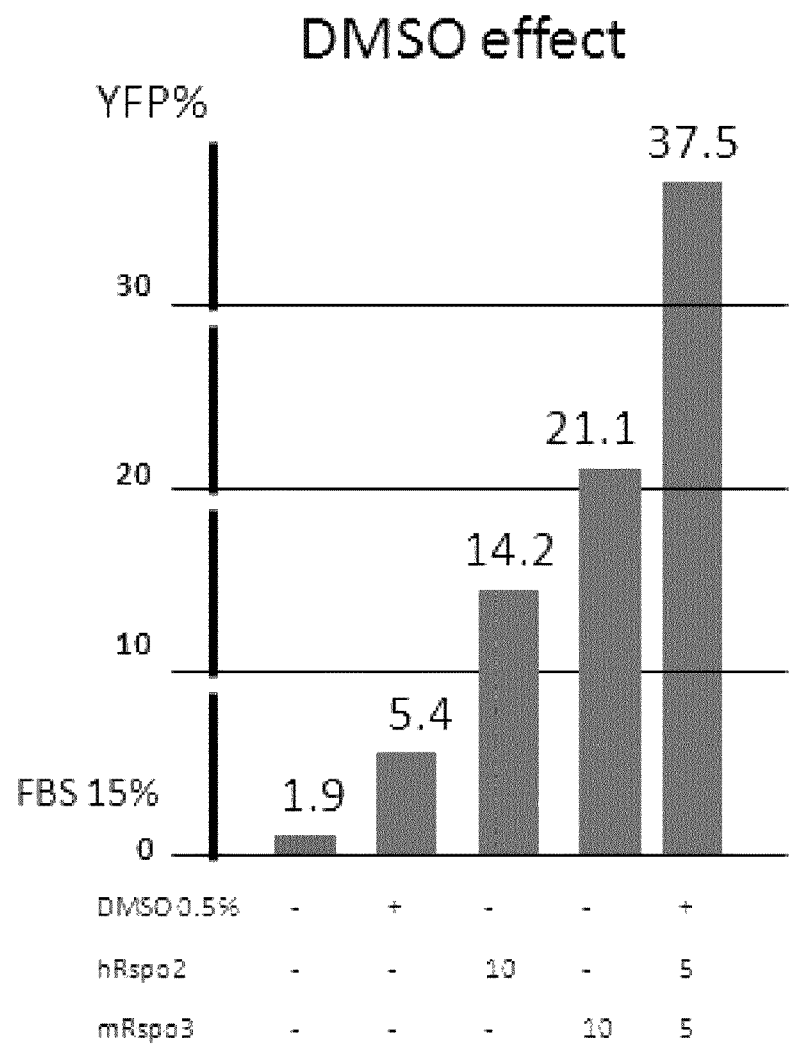

FIG. 6: DMSO has a positive effect on induced Paraxial Mesoderm progenitor (iPAM) cells induction.

iPAM induction after 4 days of differentiation in 15% FBS medium containing 0.5% DMSO. Optimal iPAM induction is obtained by combining R-spondins and DMSO. Concentrations in ng/mL.

Figure 7:
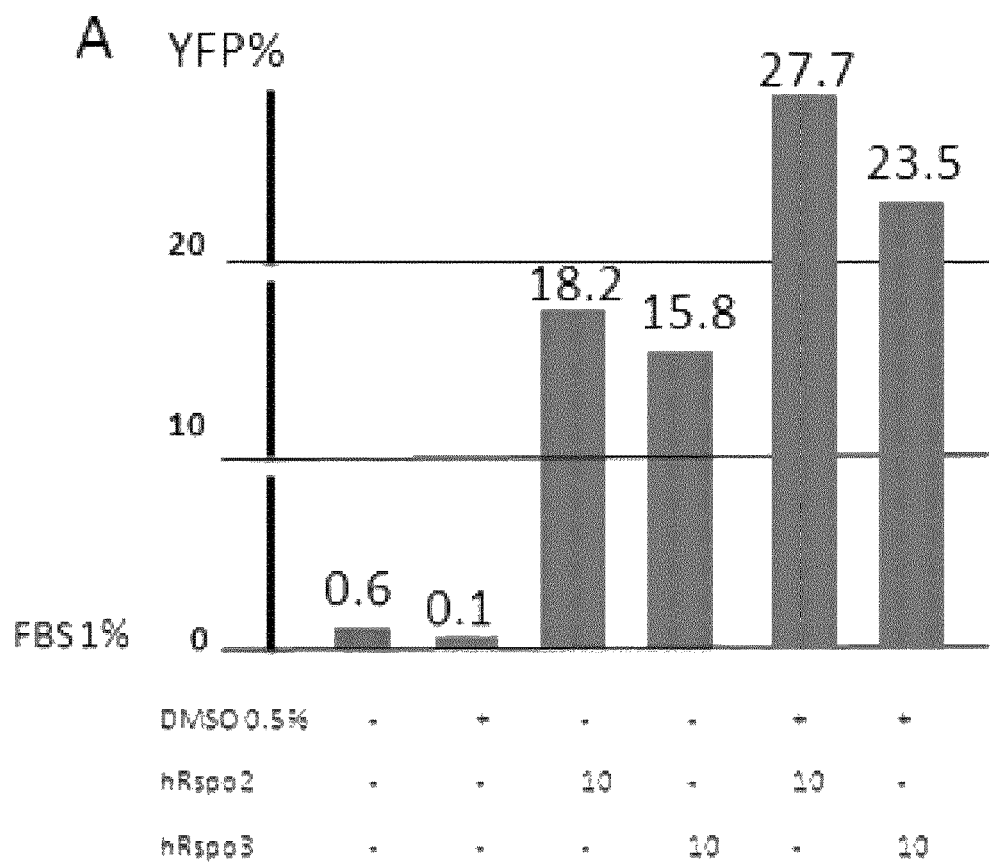
Figure 7:
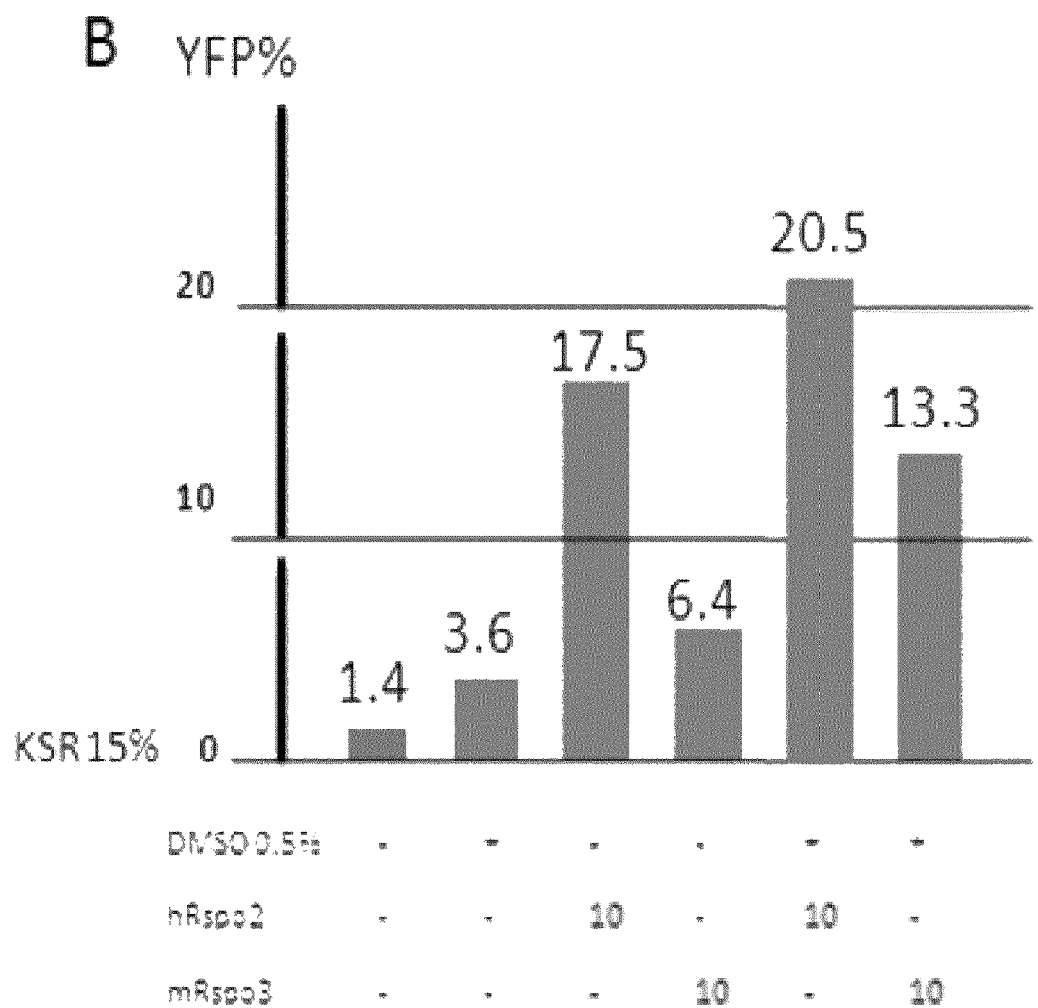

FIG. 7: Rspo2 and 3 activity in defined medium.

Analysis of the effect of recombinant mouse and human R-spondin 2 and 3 effect on iPAM induction (% of YFP positive cells) after 4 days of differentiation in 1% FBS (A) or 15% KSR (B) media. Concentrations in ng/mL.

Figure 8:
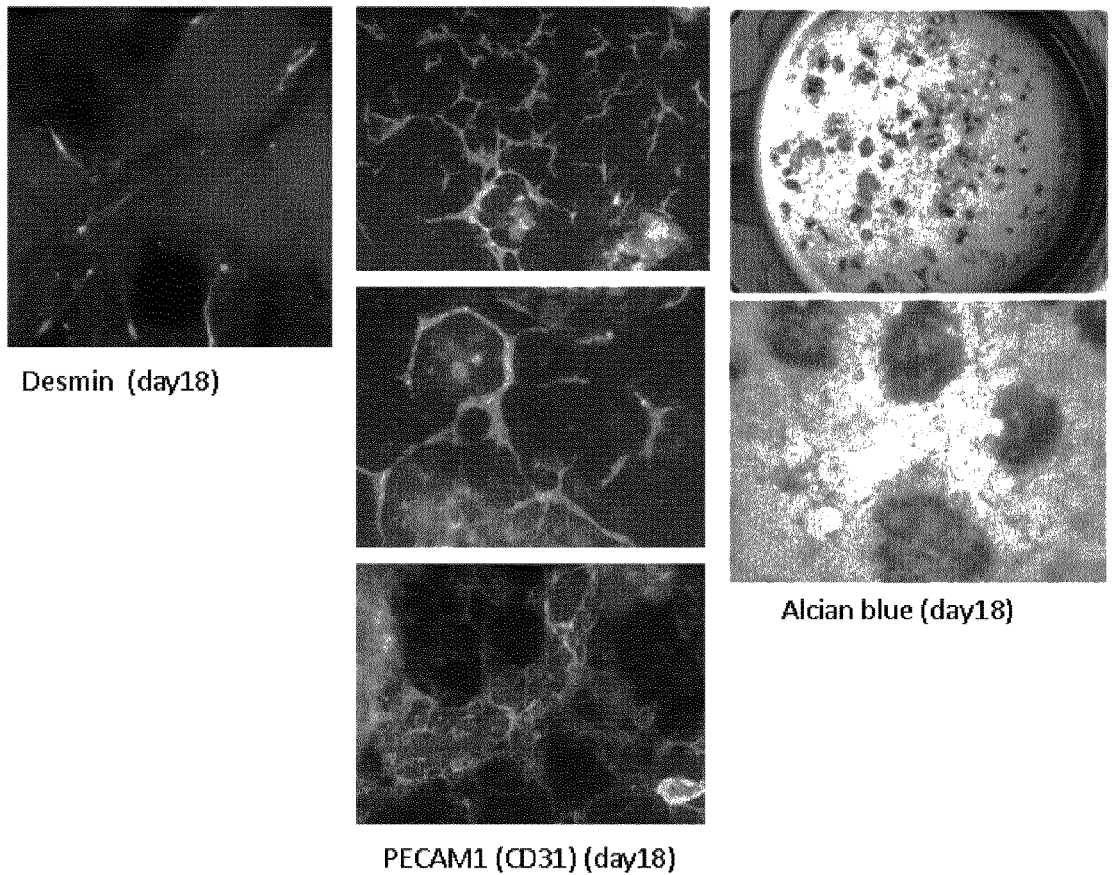

FIG. 8: Characterization of Populations of the Invention at day 18 of differentiation.

From day 0 to day 4, mouse ES cells were differentiated in presence of Rspo3, followed by 15% FBS medium until day 18. Cell types were identified by tissue-specific antibody staining, namely Muscle (Desmin, green), Endothelium (PECAM1/CD31, green) and Cartilage (Alcian Blue).

Figure 9:
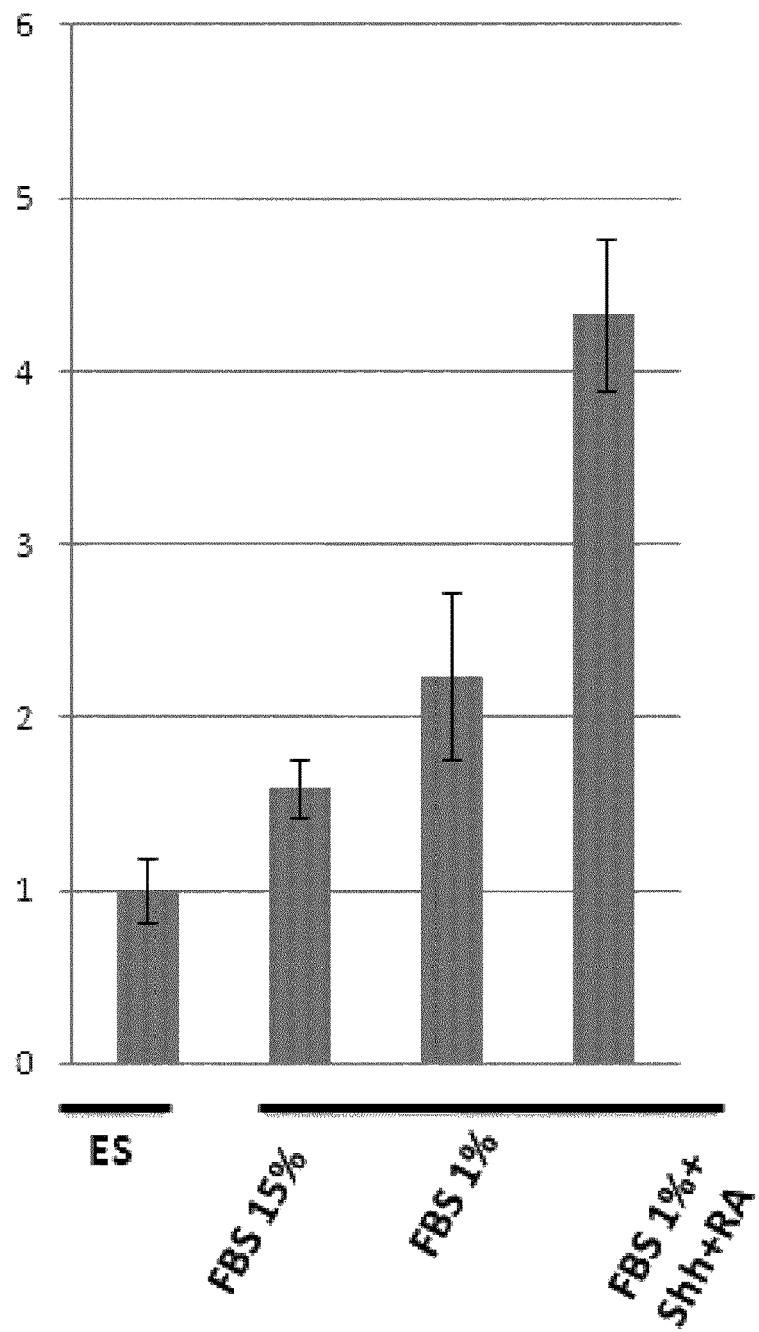
Figure 9:
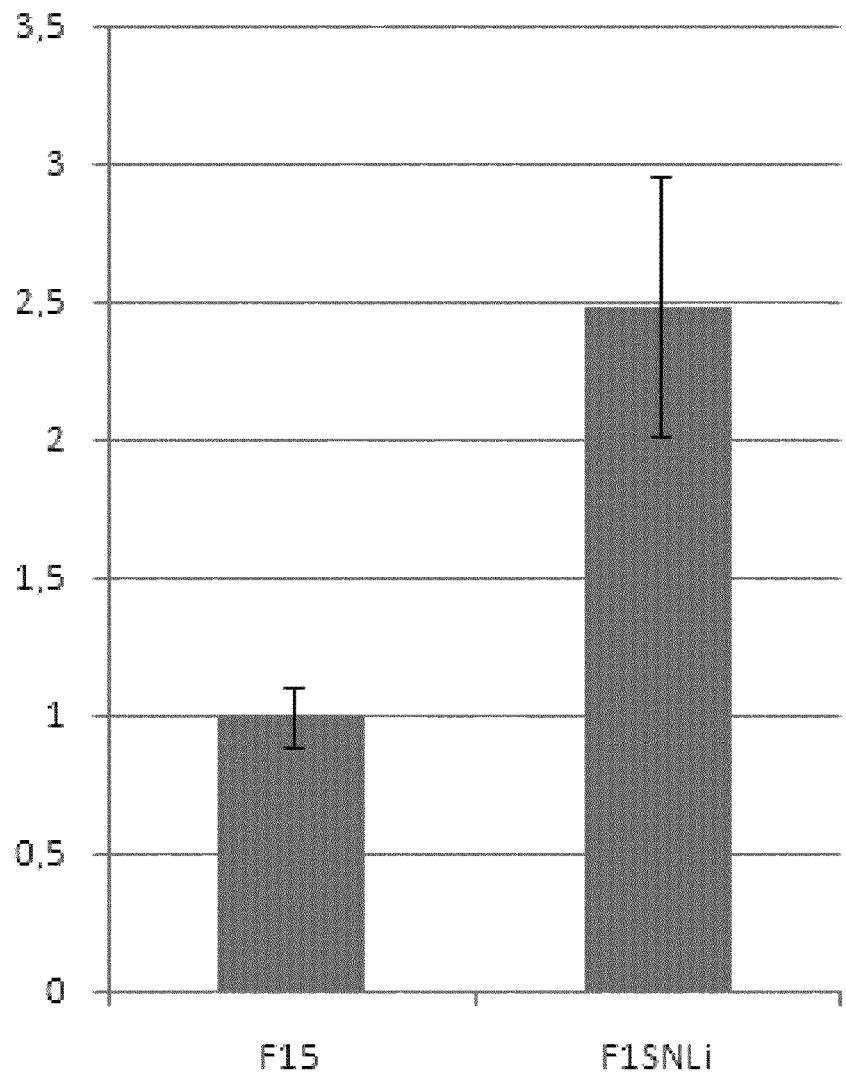

FIG. 9: Dermal and myogenic differentiation of the iPAM cells after 5 days of culture.

ES cells were cultured for 4 days in FBS15%, DMSO 0.5% and 10 ng/ml Rspo3 and then switched to FBS 15% or FBS 1% or FBS1% plus Sonic Hedgehog (Shh) and Retinoic acid (F1ShhRA) or plus Shh, Noggin and LiCl (F1SNLi). Cells were harvested the next day and analyzed by qRT-PCR for the dermal marker Dermo1 (A) and the muscle marker Myf5 (B). Graphs show fold enrichment.

FIG. 10: R-spondin induces iPAM fate in human ES cells.

Comparison of the expression of paraxial mesoderm progenitor markers Brachyury (A), PDGFRa (B), Tbx6 (C), Msgn1 (D) measured by Q RT-PCR in HUES1 undifferentiated or cultured in 15% FBS containing medium with or without Rspo3 for up to 10 days. Relative expression to undifferentiated HUES1 cells is shown (fold induction).

Figure 11:
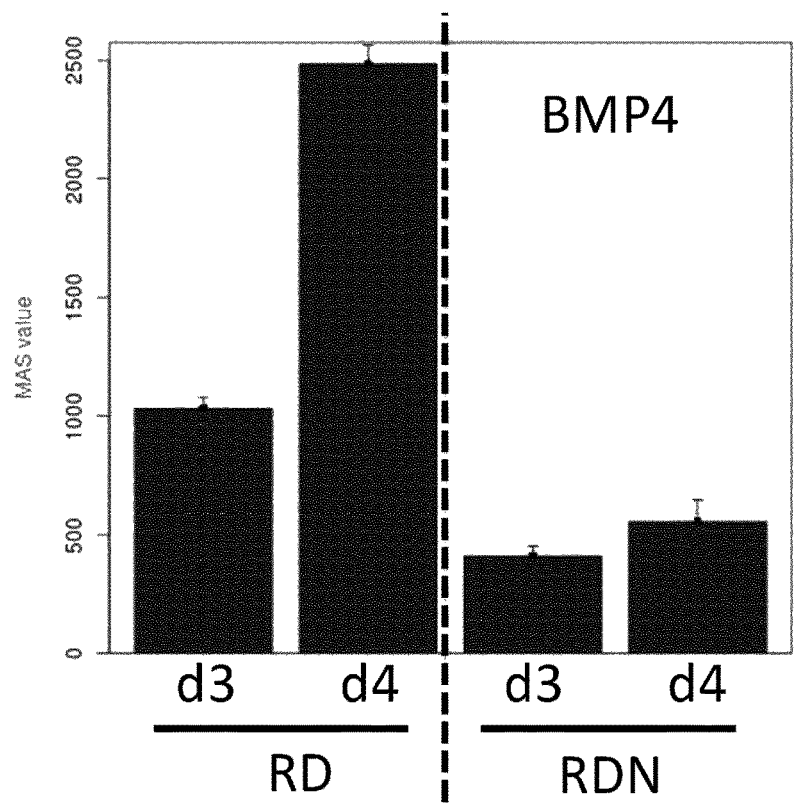

FIG. 11: Noggin promotes iPAM fate by counteracting BMP4 activity.

BMP4 expression at day3 (d3) and day4 (d4) of differentiation in the presence of 10 ng/ml Rspo3 and DMSO 0.5%, with (RDN) or without (RD) addition of Noggin (200 ng/ml) Data are shown as normalized expression value. Grey colored data point is considered non significant. Data points are means of biological triplicate samples.

FIG. 12: Molecular characterization of early stages of paraxial mesoderm differentiation.

(A). Venn diagram comparing gene signature lists (GSL method) of posterior and anterior PSM domains and of the in vitro differentiated Msgn1RepV Venus positive ES cells harvested at day3 and 4, respectively, in presence of 10 ng/ml Rspo3, DMSO 0.5% and 200 ng/ml Noggin. Key signature genes shared between the PSM in vivo and in vitro the Venus positive ES cells (induced Paraxial Mesoderm progenitor (iPAM) cells) are highlighted (black boxes). Red arrow shows the gene signature shift between day3 and day4 of ES cells differentiation.

(B) Representative genes from the Signature Gene lists common to the PSM and to the Msgn1RepV cells differentiated in vitro for 3 and 4 days (induced Paraxial Mesoderm progenitor (iPAM) cells). The genes shown were validated as strongly expressed and paraxial mesoderm specific by in-situ hybridization (data not shown). Whereas genes activated at day 3 were mostly specific to the posterior PSM, genes activated at day 4 clearly showed acquisition of anterior PSM identity.

FIG. 13: Pax3-positive PSM progenitors differentiated from ES cells in vitro can generate muscle fibers in vivo.

(A) Tibialis anterior muscles were collected after 1 month post-transplantation with in vitro differentiated Pax3-positive cells (induced Paraxial Mesoderm progenitor (iPAM) cells) labeled with a CAG-GFP lentivirus (Transverse section). Control (Crtl, non-grafted area) and engrafted area were stained (red) with antibodies against Dystrophin (DYS) and Laminin (LAMA1). Engrafted progenitors produce large areas of muscle fibers expressing dystrophin and Laminin. Nuclei are counterstained with Hoechst. Scale bar, 100 µm.

(B) Tibialis anterior muscle collected after 1 month post-transplantation (Transverse section). Control (Crtl) and Engrafted area were stained with antibodies against Myogenin (MYOG) and PAX7 (red). Nuclei are counterstained with Hoechst. For PAX7 panels, insert panels show GFP distribution. Scale bar, 100 µm.

(C) Engrafted cells express the embryonic myosin MyHCemb, MyHCI (slow) and MyHCperi/MyHC II (fast) (Left panel), and overlay with corresponding GFP/Hoechst conterstaining is shown in Right panel. For each antibody, grafted tissue is shown on top and control tissue is shown below. Scale bar, 200 µm.

EXAMPLES

Material & Methods

Cell Culture

Undifferentiated mouse ES cells Msgn1RepV (E14 derived) were maintained on gelatin-coated dishes in DMEM supplemented with 15% fetal bovine serum (FBS; from PAA), penicillin, streptomycin, 2 mM L-Glutamine, 0.1 mM non essential amino acids, 1 mM sodium pyruvate, 0.2% β-mercaptoethanol and 1,500 U/mL LIF. ES cells were co-cultured with mytomicin-inactivated MEFs (feeders). Undifferentiated human ES cells were cultured on plates coated with matrigel (BD Biosciences) in mTeSR medium (STEMCELL Technologies). Cultures were maintained in an incubator in 5% CO2 at 37° C.

Differentiation of ES Cells

ES cells were trypsinized and plated at various densities in gelatin coated, feeder-free, 24 well plates directly in serum-based (15% FBS) or serum-replacement (15% KSR, Invitrogen) conditions supplemented with factors, and DMSO (Sigma). Recombinant proteins were obtained commercially (R&D) and stock solutions were prepared according to manufacturer's recommendation. The GSK-3ß inhibitor CHIR99021 and the BMP type I receptors inhibitor Dorsomorphin were purchased from Stemgent and prepared according to the manufacturer's recommendations. Fluorescent reporter analysis and image acquisition were done on a Zeiss Axiovert system.

FACS Analysis and Cell Sorting

Cell cultures were dissociated by trypsinization, analyzed by flow cytometry on a FACScalibur (BD Biosciences) according to YFP expression. Data were further analyzed with MoFlo software (Beckman Coulter) and FlowJo software.

DNA Microarrays

Mouse E9.5 embryo PSMs were microdissected and processed as previously described (Krol et al, 2011), and prepared samples were run on Affymetrix GeneChip arrays. For differentiated cell cultures, iPAMs were sorted by flow-cytometry based on their Msgn1-YFP+ expression, and samples were prepared for microarrays. Experiments were conducted on biological triplicates. Datasets were processed using Affymetrix Microarray Suite (MAS) 5.0.

Gene Signature Lists Method

A gene expression reference was created by using all microarrays of wild-type mouse tissues deposited in GEO corresponding to Affymetrix Mouse Genome 430 2.0 Arrays (GEO platform id GPL1261). Normalization was done by calculating the mean values for each microarray. The median values for the distribution of those mean values across all microarrays were determined. This median is then used as a scaling factor for each value on each microarray. Once all microarrays have been normalized, the median expression value for each probeset is defined as the reference value. Gene signature list specific to one experimental condition was generated by normalizing the corresponding microarray data like the reference dataset. Probeset whose normalized expression value is 10 times higher than the corresponding reference value is considered to be a signature gene of that condition.

Quantitative RT-PCR

Total RNA was extracted from ES cell cultures using Trizol (Invitrogen) or with the Rnaeasy plus mini-kit (Qiagen). RT-PCR was performed on 5 ng total RNA using QuantiFast SYBR Green RT-PCR Kit (Qiagen), appropriate primers and run on a LightCycler 480II (Roche). GAPDH was used as the internal control.

Differentiated Culture Phenotyping

Cell cultures were fixed with PFA 4% overnight at 4° C. Cells were incubated 20 minutes with a blocking solution composed of 1% fetal bovine serum and 0.1% Triton in Tris Buffered Saline (TBS). Primary antibodies incubation was performed overnight at 4° C. and antibodies working dilutions were as follow: anti-GFP (Abcam) was 1:1,000, anti-Desmin (DSHB) was 1:100, anti-CD31 (BD Pharmingen) was 1:100. After TBS washes, cells were incubated with AlexaFluor488-conjugated secondary antibodies (Molecular probes) at 1:500 for 30 minutes, and counterstained with Hoechst. Alcian Blue staining was done according to standard protocol.

Cells Preparation and Transplantations in Injured Tibialis Anterior Muscles

Msgn1RepV ES cell cultures were trypsinized after 4 days of differentiation, and iPAMs were sorted based on YFP fluorescence using a FACS Aria, or Moflow Astrios (BD). iPAMS were permanently labeled by transduction overnight with a CAG-GFP lentivirus (MOI of 20-30). To remove non-integrated viral particles, cells were washed several time and reincubated, 1 hour in medium before preparation for transplantation. Grafted muscles were collected after 1 month and processed for immunohistochemistry. Dissected Tibialis Anterior muscles were prepared for cryosections (12 µm) as described previously [B. Gayraud-Morel B. et al., 2012]. Antibodies used in this study are anti-Dystrophin (Sigma), anti-Laminin (Sigma), Myogenin (Dako), Pax7 (DSHB) and GFP (Abcam). Antibodies for Myosins isoforms have been described in (S. J. Mathew Dev 138, 371 (2011). Tissue sections were incubated overnight with primary antibodies. Secondary antibodies conjugated with AlexaFluor (Molecular probes) were used at 1:500. Imaging was performed on a Zeiss Axio observer and images processed with Adobe photoshop.

Results

Example 1: Use of an Activator of the Wnt Signaling Pathway

Production of Induced Paraxial Mesoderm Progenitor (iPAM) Cells In-Vitro

We first aimed at identifying key molecular players promoting differentiation of the paraxial mesoderm lineage from ES cells. First, we investigated the time-course of paraxial mesoderm induction during mouse ES cell differentiation after formation of embryoid bodies, in DMEM based medium supplemented with 15% Fetal Bovine serum (FBS15%). Differentiation in paraxial mesoderm progenitor cells was characterized by activation of the Brachyury/T, Tbx6, and Msgn1 markers detected by PCR. Our data suggest that between day 1 and 4 of culture, some differentiated cells are in a presomitic mesoderm-like stage.

The Msgn1RepV Reporter ES Line Characterization.

In order to follow the differentiation of ES cells toward the first stage of paraxial mesoderm differentiation (ie presomitic fate), which represents the first step of skeletal muscle differentiation after acquisition of a mesodermal identity, we generated a transgenic mouse ES cell line harboring a fluorescent reporter specifically expressed in paraxial mesoderm progenitors. We used the promoter from the mouse Msgn1, a gene specific for the presomitic mesoderm, to drive the expression of Venus (a modified YFP). The transgenic Msgn1RepV (Mesogenin1 Reporter Venus) mouse ES cell line was subsequently validated using the tetraploid aggregation method to generate embryos entirely derived from the transgenic ES cells. As expected, transgenic mouse embryos exhibit fluorescently labeled paraxial mesoderm tissue, thus, validating the tissue specificity of Venus expression in the transgenic ES cell line.

R-Spondins Identification.

In order to optimize the differentiation conditions for paraxial mesoderm progenitors, we developed a manual screening assay, testing candidate growth factors and drugs interfering with various signaling pathways on ES cells. The Msgn1RepV reporter cells were plated at a defined density in 24-well plates coated with gelatin (0.1%). Two basal culture media were selected: a DMEM based medium containing 15% fetal bovine serum (FBS, high serum) and a defined serum-free medium containing 15% KSR (Invitrogen/Gibco). These basal media were supplemented with candidate factors on day 0 of differentiation. Control and experimental conditions were cultured in parallel. Cells were left to differentiate for three to four days with medium changed on day 2 or 3. Cell cultures were analyzed on day 3 and 4 of differentiation visually and by flow cytometry for YFP+ population quantification.

After 4 days of differentiation, control differentiation in 15% FBS results in a low and variable induction of YFP+ cells (typically 1 to 15% of the culture), and differentiation in defined medium 15% KSR (Invitrogen) results in an even lower induction (typically 1%). Among the set of candidates tested, we identified the secreted R-spondin3 protein as being able to increase dramatically the induction of YFP+ cells. In our assay, R-spondin3 at 10 ng/mL is sufficient to increase significantly the induction of YFP+ cells both in FBS based medium and KSR based medium, up to 70% (FIGS. 1, 2 and 7). The R-spondin3 response saturated between 30 to 100 ng/mL. While at day 0, the YFP+ population is <1% of the cells, in R-spondin3 supplemented differentiation medium, YFP+ population can represent more than 50%, up to 70% of the cells at day4 (FIG. 2B). In human ES cells, induction of the paraxial mesoderm progenitor markers, Brachyury, PDGFRa, Tbx6 and Msgn1 is observed after 3 to 10 days of culture in 15% FBS containing medium when treating huES1 with R-spondin3 (FIG. 10).

Paraxial Mesoderm Progenitors Characterization.

To confirm induction of a paraxial mesoderm progenitor cell fate upon differentiation of ES cells in vitro, we sorted the YFP+ cell population after four days of differentiation in presence of R-spondin3 (FIG. 3A) and analyzed the YFP+ versus YFP− cells by qRT-PCR for the key paraxial mesoderm markers Msgn1 and Tbx6 (FIG. 3B). We confirmed that the YFP+ population strongly expresses the Msgn1 endogenous gene, as well as Tbx6, demonstrating that we are able to generate paraxial mesoderm progenitors (iPAM) in vitro.

R-Spondin Family and Wnt Signaling.

We next asked whether other members of the R-spondin family can induce paraxial mesoderm progenitor iPAM cells (Msgn1-YFP+ paraxial mesoderm progenitors). ES cells were cultured in medium containing recombinant R-spondin proteins (R-spondins 1-4) supplemented with 15% FBS and allowed to differentiate for 4 days (FIG. 4B). Two members of the family, R-spondin2 and R-spondin3, exhibit comparable activities and significantly increase the number of YFP+ cells. The activity of R-spondin family proteins has been associated with canonical Wnt/Beta catenin signaling (Kim et al., 2008; Nam et al., 2006) and more recently with Wnt/PCP signaling (Ohkawara et al., 2011). We analyzed the effect of the inhibition of canonical Wnt signaling on R-spondin dependent differentiation using the secreted Dkk1 inhibitor, (FIG. 4A). Supplementation of the medium with the extracellular Wnt antagonist Dkk1 results in a sharp decrease of YFP+ induction. Moreover, adding Dkk1 to FBS-containing medium blocks the effect of R-spondin3, suggesting that R-spondin3 effect is mediated by the Wnt canonical pathway. We also analyzed the expression of luciferase from a plasmid driven by a promoter responding to canonical Wnt signaling (BAT-luc) transfected in ES cells treated or not with R-spondin3, and with Dkk1 or with the compound LiCl which can activate the Wnt pathway (FIG. 4C). Luciferase was strongly activated by R-spondin3 treatment suggesting that it activates the canonical Wnt pathway in this context.

To further test whether R-spondin3 effect is mediated by the Wnt canonical pathway, we tested the effect of CHIR99021, a well described GSK-3ß inhibitor (Ring et al., 2003). FIG. 5 shows that after 4 days, CHIR99021 is as efficient as Rspo-3 in inducing YFP+ cells, suggesting that R-spondin3 effect is mediated by activation of the canonical Wnt pathway.

Dimethyl sulfoxide (DMSO) has been shown to promote the differentiation of several cell types, notably mesoderm from the P19 Embryonic Carcinoma (EC) cell line (McBurney et al., 1982; Skerjanc, 1999). The exact mechanism of action of DMSO in cell culture is not known, and it has been hypothesized that DMSO modifies the plasma membrane properties, making the cells more responsive to extracellular signals present in the differentiation medium. Addition of 0.5% of DMSO to FBS-containing medium, results in an increase of YFP+ cells after 4 days in culture (FIGS. 5, 6 and 7), although this increase is modest compared to the increase due to the addition of R-spondin2 or R-spondin3, or both. Interestingly, the addition of R-spondins and DMSO synergizes to enhance paraxial mesoderm progenitors differentiation (FIGS. 5, 6 and 7). Optimal conditions for paraxial mesoderm differentiation were observed when both DMSO and R-spondin 2 and/or 3 were combined (FIGS. 5, 6 and 7). Importantly, this effect is also seen in a serum-free, defined KSR based medium (FIG. 7B).

Paraxial Mesoderm Progenitors Differentiation Potential

We next explored the differentiation potential of the iPAM cell population. In vivo, paraxial mesoderm progenitor cells are fated to become skeletal muscles, vertebral tissues (cartilage, bone), dorsal dermis, endothelium, and other tissues such as adipose tissues.

Thus, we performed sequential differentiation protocols, aiming at first generating iPAM cells, and then differentiating them further in 15% FBS medium or by applying various described differentiation protocols (see below), in particular «Myogenic» and «Chondrogenic» media.

For example, between day0 to day4, ES cells were exposed to optimized differentiation conditions (ie. R-spondin3 10 ng/mL, DMSO 0.5%, in 15% FBS basal medium). On day 4, culture medium was changed and cells were exposed to specific differentiation media until day 18, with medium replacement every 3 days. At day 18, cell cultures were fixed and analyzed by tissue specific histochemical staining or immunofluorescence (FIG. 8). Under optimized differentiation conditions, cell cultures were positive for Cartilage (Alcian blue positive nodules), Muscles (Desmin positive fibers) and Endothelium (CD31/PECAM1). Alternatively, after 4 days in differentiation conditions (ie. Rspo3 10 ng/mL, DMSO 0.5%, in FBS15% basal medium), cells were switched to FBS 15% or FBS 1% or FBS1% plus Sonic Hedgehog (Shh) and Retinoic acid (F1ShhRA) or plus Shh, Noggin and LiCl (F1SNLi). Cells were harvested the next day and analyzed by qRT-PCR for the dermal marker Dermo1 and the muscle marker Myf5 (FIG. 9). Significant activation of these markers was observed indicating differentiation of the iPAM cells toward the dermal and muscle lineages respectively.

Myogenic Protocol:

Alternatively, induced paraxial mesoderm progenitors (iPAM) cells can be differentiated in two-dimensional culture into muscle cells using SFO3 medium complemented with BMP4, ActivinA and IGF-1 for 3 days, followed by 3 days of SFO3 medium complemented with LiCl and Shh.

Induced paraxial mesoderm progenitors (iPAM) cells can be cultured in a hanging drop for 3 days at 800 cells/20 uL in differentiation medium, composed of DMEM supplemented with 10% fetal calf serum (FCS), 5% horse serum (Sigma), 0.1 mM 2-mercaptoethanol, 0.1 mM nonessential aminoacids, and 50 ug/ml penicillin/streptomycin. After 3 days, the medium is changed and cell aggregates are transferred on a low attachment plate. At day 6, cells are plated and cultured in differentiation medium on plates coated with Matrigel (BD Bioscience, Bedford, Mass., USA). Myogenic differentiation is achieved by withdrawal of FBS from confluent cells and addition of 10 ug/ml insulin, 5 ug/ml transferrin, and 2% horse serum.

Induced paraxial mesoderm progenitors (iPAM) cells can also be cultured for 3 weeks in Skeletal Muscle Cell Medium (Lonza, Chemicon) complemented with EGF, insulin, Fetuin, dexamethasone, and bFGF (100 ng/mL).

Osteogenic Protocol:

For skeletal lineages, Induced paraxial mesoderm progenitors (iPAM) cells are exposed to 200 ng/ml human or mouse recombinant BMP4 or a combination of 1 uM retinoic acid and 10 mM Lithium Chloride. Alternatively, cells are plated on gelatin-coated plates at a density of $1-3 \times 10^3$ per well (24-well plate) and cultured for 28 days in bone differentiation medium (DMEM, 10% FBS, 2 mM 1-Glutamine, 1× Penicillin/streptomycin (P/S), 0.1 μM dexamethasone, 50 μM ascorbic acid 2-phosphate, 10 mM β-glycerophosphate, 10 ng/mL BMP4) in order to observe cells expressing bone specific markers or secreting alcian blue positive extracellular matrix. Differentiated skeletal cell lineages are identified using specific stainings for extracellular matrix components of bone and cartilage including alcian blue or alizarin red, as well as by immunofluorescence using chondrocyte- and/or osteocyte specific antibodies.

Induced paraxial mesoderm progenitors (iPAM) cells can also be differentiated into the bone lineage using the following differentiation medium composed of DMEM, 10% FBS, 2 mM L-Glutamine, 1×P/S, 0.1 mM Dexamethasone, 50 mM ascorbic acid 2-phosphate, 10 mM beta-glycerophosphate, and 10 ng/mL BMP4, and vitamin D3 for 20 days, with medium changed every 3 days. Bone formation can be confirmed by staining the differentiating culture with Alizarin red, well known in the art that results to stain differentiated bone in red. Extracellular accumulation of calcium can also be visualized by von Kossa staining. Alternatively, differentiating cells can be lysed and assayed for ALP activity using BBTP reagent. Alternatively, differentiating cells can be analyzed for osteoblast lineage markers expression, for example Osterix (Osx) and Cbfa1/Runx2, alkaline phosphatase, collagen type I, osteocalcin, and osteopontin.

Chondrogenic Protocol:

For chondrogenic cell differentiation, induced paraxial mesoderm progenitors (iPAM) cells are plated at a density of $8 \times 10^4$ per well (24-well plate) and cultured for 30 minutes in a 37 C incubator in cartilage differentiation medium (αMEM, 10% FBS, 2 mM 1-Glutamine, 1×P/S, 0.1 μM Dexamethasone, 170 μM ascorbic acid 2-phosphate). Next, an equal amount of cartilage cell differentiation medium with 10 ng/mL TGF beta3 is added to the well. After one week, the medium is replaced with cartilage differentiation medium supplemented with 10 ng/mL Bmp2. After 21 days cartilaginous nodules secreting extracellular matrix can be observed. Induced paraxial mesoderm progenitors (iPAM) cells can also be differentiated into cartilage cells using a differentiation medium based on alphaMEM, 10% FBS, 2 mM L-Glutamine, 1×P/S, 0.1 mM Dexamethasone, and 170 mM ascorbic acid 2-phosphate or DMEM supplemented with 0.1 mM dexamethasone, 0.17 mM ascorbic acid, 1.0 mM sodium pyruvate, 0.35 mM L-proline, 1% insulin-transferrin sodium, 1.25 mg/ml bovine serum albumin, 5.33 ug/ml linoleic acid, and 0.01 ug/ml transforming growth factor-beta), as well as TGFbeta3 or BMP2. Cells are cultured for several weeks, with medium changed every 3 days. Differentiation can also be performed at high density on 3D scaffold such as Alginate beads in a DMEM based medium containing 10% FBS and antibiotic supplemented with 100 ng/ml recombinant human Bone Morphogenic Protein-2 (BMP-2) and 50 mg ascorbic acid. Cartilage formation can be confirmed by Alcian Blue staining of the differentiating culture, well known in the art that results in the staining of Muco-glycoproteins in blue. Alternatively, a safranin O staining can be performed.

Dermal Fibroblast Protocol:

Induced paraxial mesoderm progenitors (iPAM) cells can be differentiated into dermal fibroblasts by culturing them on a scaffold of collagen in medium containing a fibroblast growth factor such as bFGF (basic Fibroblast Growth Factor) or a member of the Wnt family of growth factors.

Next, to confirm that R-spondin also induces paraxial mesoderm progenitors (iPAM) cells from human ES cells differentiation, HUES1 cells were plated as single cells and differentiated in 15% FBS containing medium with or without Rspo3. qRT-PCR time course analysis for paraxial mesoderm progenitor markers expression was performed (FIG. 10). Strong activation of Msgn1 and Tbx6 during hES cells differentiation in presence of R-spondin3, demonstrate that iPAM cells can be differentiated from hES cells.

Example 2: Use of an Activator of the Wnt Signaling Pathway and an Inhibitor of BMP Signaling Pathway Characterization of the Msgn1-YFP+ Cell Population Using R-spondin proteins and DMSO, we are able to produce in a single step 70% of Msgn1-YFP+ cells (FIG. 2B). To directly compare the transcriptome of Msgn1-YFP+ to their in-vivo counterpart (ie. presomitic mesoderm, PSM), we used microarrays to generate a global transcriptome profiling of consecutive mouse fragments representing progressively more mature stages of differentiation (data not shown). The PSM fragments spanned from the tail bud level to the somitic region where the myogenic program is first activated. Based on this microarray series, we were able to define sets of signature genes defining the progressive maturation stage of cells from the tail bud (epiblast) to the presomitic mesoderm and somitic stages. In parallel, we differentiated ES cells in presence of R-spondin3 and DMSO (RD), sorted the Msgn1-YFP+ cell population and generated microarrays of this population at day3 and day4 of differentiation respectively. Global transcriptomes and signature genes sets were compared between the in vivo PSM and in vitro differentiated Msgn1-YFP+ cells (data not shown).

We confirm that Msgn1-YFP+ cells express a number of key paraxial mesoderm markers already validated by Q-PCR such as Msgn1 and Tbx6 (FIG. 3B). We noticed that, in contrast to the native PSM cells, the Msgn1-YFP+ population also activates cardiac and angiogenic markers, which are a signature of more ventral/lateral mesoderm derivatives. Also, we found that TGFβ/BMP signaling tends to be up-regulated in Msgn1-YFP+. Unexpectedly, we found that the Msgn1-YFP+ cell population expresses BMP4 at a significant level whereas BMP4 is detected only at very low level in vivo in the PSM. This was problematic because BMP4 has been shown to prevent cells to acquire a paraxial mesoderm fate at the expenses of lateral plate fates (Pourquié O et al, 1996, Tonegawa A et al, 1997).

Noggin to Counteract BMP4 Signaling

To counteract this BMP4 activity, we tested the effect of addition of recombinant Noggin (Nog) protein known to inhibit BMP4, to the differentiation medium. We found that addition of Noggin from day 0 or day 1 of differentiation, Msgn1-YFP+ cells effectively repress BMP4 expression compared to cells cultured in differentiation medium lacking Noggin. We further defined both the optimal concentration and timing of Noggin addition. Noggin does not change the total number of Msgn1-YFP+ induced Paraxial Mesoderm progenitor (iPAM) cells (efficiency of production) or the total cell number in culture but rather changes the maturation of the Msgn1-YFP+ (efficiency of maturation). To better characterize the impact of Noggin on Msgn1-YFP+ cells, we performed microarrays on the Msgn1-YFP+ induced paraxial mesoderm progenitors (iPAM) population at day 3 and 4 of differentiation (FIG. 11, compare conditions RDN and RD).

We show that adding Noggin to the medium represses BMP4 expression in the Msgn1-YFP+ cells, leading to the upregulation of several PSM specific markers including Tbx6, Pcdh8, Pax3, Foxc1, Raldh2 and Ripply2 (FIG. 12B and data not shown).

BMP Inhibitors and BMP Signaling

We detected strong upregulation of the BMP inhibitors Follistatin (Fst) and Cerberus (Cer1) in the mouse PSM microarray series and other BMP inhibitors such as Chordin, Noggin, and Gremlin1 are known to be expressed by the adjacent tissues during development [McMahon J A et al, 1998; Stafford D A et al, D2011 and Scott I C et al, 2000]. This suggests that in vivo the PSM requires BMP inhibition to mature properly, and that in vitro BMP inhibition is also required to the proper maturation of iPAM cells.

We screened a set of BMP inhibitors, including recombinant proteins Noggin (Nog), Chordin (Chd), Chordin-like 1 (Chdl1), Follistatin (Fst), Follistatin-like 1 (Fstl1), Dan family protein including Cerberus 1 (Cerberus) and Gremlin 1 (Grem1); at varying concentration range (10-200 ng/mL), and various time-window (day 0-4, day 1-4) and analyzed the impact on BMP4 and the PSM marker Tbx6 expression. Additionally, we tested the chemical compound Dorsomorphin (Compound C), a specific BMP type I receptor inhibitor, at various concentration (0.1-1 µM) and various time-window (day 0-4, day 1-4). Addition of the BMP inhibitors does not affect the number of induced paraxial mesoderm progenitors (iPAM) cells or the total cell number in culture (data not shown). Among the set of candidates tested, we identified in particular Noggin (Nog), Follistatin (Fst) and Dorsomorphin as promoting induced paraxial mesoderm progenitors (iPAM) maturation by counteracting BMP4 and activating Msgn1 and Tbx6 expression (data not shown).

To monitor the PSM identity of Msgn1RepV cells differentiated in vitro, we purified them by FACS after both 3 and 4 days of differentiation in the presence of R-spondin3 and Noggin. qRT-PCR analysis confirmed that the sorted population strongly expresses Msgn1 and Tbx6, as expected for PSM cells (FIG. 3B). For a more systematic analysis, gene signatures were generated for both time-points as described above. Comparison of Day3 differentiated ES gene signature to that of the PSM transcriptional domains revealed that the differentiated ES cells expressed a large number of genes of the posterior PSM including T, Rspo3 and Fgf8 (FIG. 12A-B). Thus the cells expressing the Msgn1 reporter bear a close molecular resemblance to their counterparts in vivo.

We then asked whether the maturation process could be pursued further in vitro. Strikingly, Day4 but not Day3 differentiated ES cells were found to activate genes specific for the anterior PSM such as Mesp2, Ripply2 or Foxc1, indicating that these cells have acquired an anterior PSM identity (FIG. 12B). In particular, these Day4 cells significantly upregulated the Pax3 gene. Pax3 regulates the differentiation of the myogenic lineage and, recently, overexpression of Pax3 in ES cells was shown to induce muscle [Darabi, R et al., 2008]. This suggested that, over time, R-spondin3 and Noggin treatment can transform undifferentiated ES cells into bona fide Pax3 positive muscle progenitors without genetic manipulation.

In conclusion, these results demonstrate the potential use and the synergistic effect of an activator of the Wnt signaling pathway like R-spondin3 and of an inhibitor of the Bone Morphogenetic Protein (BMP) signaling pathway like Noggin to obtain induced paraxial mesoderm progenitor (iPAM) cells.

Example 3: Generation of Myogenic Lineage In Vivo

To further drive the terminal differentiation of these precursors, we next took an in vivo approach. Pax3-positive cells obtained after 4 days of differentiation in medium containing R-spondin3 and Noggin were transduced with a GFP-expressing lentivirus to permanently label them. They were then injected into the Tibialis anterior muscle of adult Rag2-/-:γc-/- immunocompromised mice that had been injured by intramuscular injection of the snake venom cardiotoxin [Gayraud-Morel B. et al., 2012]. Examination of the transplanted muscles after 1 month showed that the grafted GFP-expressing cells reconstituted large areas filled with muscle fibers expressing laminin and dystrophin (n=3; FIG. 13A). The fibers expressed high levels of the differentiation marker Myogenin, had a small diameter and were not aligned as in adult muscle suggesting that they might correspond to embryonic primary fibers (FIG. 13B) [Gayraud-Morel B. et al., 2009]. This was confirmed by showing that these fibers expressed embryonic and perinatal isoforms of myosin heavy chain (FIG. 13C). Remarkably, a significant population of cells expressing the satellite cell-specific marker Pax7 was observed in the engrafted regenerating area suggesting that the differentiated ES cells were also able to produce a progenitor pool of muscle cells (FIG. 13B). Thus, when transplanted in vivo in injured muscles, Pax3-positive cells derived in vitro are able to continue their differentiation toward the myogenic lineage.

REFERENCES

Throughout this application, various references describe the state of the art to which this invention pertains. The disclosures of these references are hereby incorporated by reference into the present disclosure.

Barberi, T., Bradbury, M., Dincer, Z., Panagiotakos, G., Socci, N. D. and Studer, L. (2007). Derivation of engraftable skeletal myoblasts from human embryonic stem cells. Nat Med 13, 642-8.

Carmon, K. S., Gong, X., Lin, Q., Thomas, A. and Liu, Q. (2011). R-spondins function as ligands of the orphan receptors LGR4 and LGR5 to regulate Wnt/{beta}-catenin signaling. Proc Natl Acad Sci USA 108, 11452-7.

Chal, J. and Pourquie, O. (2009). Patterning and Differentiation of the Vertebrate Spine. In The Skeletal System, (ed. O. Pourquie), pp. 41-116: Cold Spring Harbor Laboratory Press.

Chambers, I. (2004). The molecular basis of pluripotency in mouse embryonic stem cells. Cloning Stem Cells 6, 386-91.

Chapman, D. L., Agulnik, I., Hancock, S., Silver, L. M. and Papaioannou, V. E. (1996). Tbx6, a mouse T-Box gene implicated in paraxial mesoderm formation at gastrulation. Dev Biol 180, 534-42.

Clevers, H. (2006). Wnt/beta-catenin signaling in development and disease. Cell 127, 469-80.

Cohen, P. and Goedert, M. (2004). GSK3 inhibitors: development and therapeutic potential. Nat Rev Drug Discov 3, 479-87.

Cuny G D, Yu P B, Laha J K, Xing X, Liu J F, Lai C S, Deng D Y, Sachidanandan C, Bloch K D, Peterson R T. Structure-activity relationship study of bone morphogenetic protein (BMP) signaling inhibitors. Bioorg Med Chem. Lett. 2008 Aug. 1; 18(15):4388-92. Epub 2008 Jun. 27.

Darabi, R., Gehlbach, K., Bachoo, R. M., Kamath, S., Osawa, M., Kamm, K. E., Kyba, M. and Perlingeiro, R. C. (2008). Functional skeletal muscle regeneration from differentiating embryonic stem cells. Nat Med 14, 134-43.

Darabi, R., Santos, F. N., Filareto, A., Pan, W., Koene, R., Rudnicki, M. A., Kyba, M. and Perlingeiro, R. C. (2011). Assessment of the Myogenic Stem Cell Compartment Following Transplantation of Pax3/Pax7-Induced Embryonic Stem Cell-Derived Progenitors. Stem Cells.

de Lau, W., Barker, N., Low, T. Y., Koo, B. K., Li, V. S., Teunissen, H., Kujala, P., Haegebarth, A., Peters, P. J., van de Wetering, M. et al. (2011). Lgr5 homologues associate with Wnt receptors and mediate R-spondin signaling. Nature.

Dekel, I., Magal, Y., Pearson-White, S., Emerson, C. P. and Shani, M. (1992). Conditional conversion of ES cells to skeletal muscle by an exogenous MyoD1 gene. New Biol 4, 217-24.

Derynck Rik, 2008. The TGF-β Family. CSHL. Kōhei Miyazono Editors).

Dimos, J. T., Rodolfa, K. T., Niakan, K. K., Weisenthal, L. M., Mitsumoto, H., Chung, W., Croft, G. F., Saphier, G., Leibel, R., Goland, R. et al. (2008). Induced pluripotent stem cells generated from patients with ALS can be differentiated into motor neurons. Science 321, 1218-21.

Dinsmore, J., Ratliff, J., Deacon, T., Pakzaban, P., Jacoby, D., Galpern, W. and Isacson, O. (1996). Embryonic stem cells differentiated in vitro as a novel source of cells for transplantation. Cell Transplant 5, 131-43.

Fukada, S., Higuchi, S., Segawa, M., Koda, K., Yamamoto, Y., Tsujikawa, K., Kohama, Y., Uezumi, A., Imamura, M., Miyagoe-Suzuki, Y. et al. (2004). Purification and cell-surface marker characterization of quiescent satellite cells from murine skeletal muscle by a novel monoclonal antibody. Exp Cell Res 296, 245-55.

Gayraud-Morel B. et al., J Cell Sci 125, 1738 (Apr. 1, 2012).

Gayraud-Morel B., F. Chretien, S. Tajbakhsh, *Regen Med* 4, 293 (March, 2009).

Gayraud-Morel B. et al. J Cell Sci 125, 1738 (Apr. 1, 2012).

Han, X. H., Jin, Y. R., Seto, M. and Yoon, J. K. (2011). A WNT/beta-catenin signaling activator, R-spondin, plays positive regulatory roles during skeletal myogenesis. J Biol Chem 286, 10649-59.

Hankenson, K. D., Sweetwyne, M. T., Shitaye, H. and Posey, K. L. (2010). Thrombospondins and novel TSR-containing proteins, R-spondins, regulate bone formation and remodeling. Curr Osteoporos Rep 8, 68-76.

Hirsinger, E., Jouve, C., Dubrulle, J. and Pourquie, O. (2000). Somite formation and patterning. Int Rev Cytol 198, 1-65.

Hollnagel A, Oehlmann V, Heymer J, Rüther U, Nordheim A. Id genes are direct targets of bone morphogenetic protein induction in embryonic stem cells. J Biol. Chem. 1999 Jul. 9; 274(28):19838-45.

Jin, Y. R., Turcotte, T. J., Crocker, A. L., Han, X. H. and Yoon, J. K. (2011). The canonical Wnt signaling activator, R-spondin2, regulates craniofacial patterning and morphogenesis within the branchial arch through ectodermal-mesenchymal interaction. Dev Biol 352, 1-13.

Kazanskaya, O., Glinka, A., del Barco Barrantes, I., Stannek, P., Niehrs, C. and Wu, W. (2004). R-Spondin2 is a secreted activator of Wnt/beta-catenin signaling and is required for *Xenopus myogenesis*. Dev Cell 7, 525-34.

Kazanskaya, O., Ohkawara, B., Heroult, M., Wu, W., Maltry, N., Augustin, H. G. and Niehrs, C. (2008). The Wnt signaling regulator R-spondin 3 promotes angioblast and vascular development. Development 135, 3655-64.

Kennedy, K. A., Porter, T., Mehta, V., Ryan, S. D., Price, F., Peshdary, V., Karamboulas, C., Savage, J., Drysdale, T. A., Li, S. C. et al. (2009). Retinoic acid enhances skeletal muscle progenitor formation and bypasses inhibition by bone morphogenetic protein 4 but not dominant negative beta-catenin. BMC Biol 7, 67.

Kim, K. A., Wagle, M., Tran, K., Zhan, X., Dixon, M. A., Liu, S., Gros, D., Korver, W., Yonkovich, S., Tomasevic, N. et al. (2008). R-Spondin family members regulate the Wnt pathway by a common mechanism. Mol Biol Cell 19, 2588-96.

Krol A J, Roellig D, Dequéant M L, Tassy O, Glynn E, Hattem G, Mushegian A, Oates A C, Pourquié O. Evolutionary plasticity of segmentation clock networks. lopment. 2011 July; 138(13):2783-92.

Loser, P., Schirm, J., Guhr, A., Wobus, A. M. and Kurtz, A. (2010). Human embryonic stem cell lines and their use in international research. Stem Cells 28, 240-6.

McBurney, M. W., Jones-Villeneuve, E. M., Edwards, M. K. and Anderson, P. J. (1982). Control of muscle and neuronal differentiation in a cultured embryonal carcinoma cell line. Nature 299, 165-7.

McMahon J A, Takada S, Zimmerman L B, Fan C M, Harland R M, McMahon A P. Noggin-mediated antagonism of BMP signaling is required for growth and patterning of the neural tube and somite. Genes Dev. 1998 May 15; 12(10):1438-52.

Metallo, C. M., Mohr, J. C., Detzel, C. J., de Pablo, J. J., Van Wie, B. J. and Palecek, S. P. (2007). Engineering the stem cell microenvironment. Biotechnol Prog 23, 18-23.

Mizuno, Y., Chang, H., Umeda, K., Niwa, A., Iwasa, T., Awaya, T., Fukada, S., Yamamoto, H., Yamanaka, S., Nakahata, T. et al. (2010). Generation of skeletal muscle stem/progenitor cells from murine induced pluripotent stem cells. FASEB J 24, 2245-53.

Montcouquiol, M., Crenshaw, E. B., 3rd and Kelley, M. W. (2006). Noncanonical Wnt signaling and neural polarity. Annu Rev Neurosci 29, 363-86.

Nam, J. S., Turcotte, T. J., Smith, P. F., Choi, S, and Yoon, J. K. (2006). Mouse cristin/R-spondin family proteins are novel ligands for the Frizzled 8 and LRP6 receptors and activate beta-catenin-dependent gene expression. J Biol Chem 281, 13247-57.

Nam, J. S., Turcotte, T. J. and Yoon, J. K. (2007). Dynamic expression of R-spondin family genes in mouse development. Gene Expr Patterns 7, 306-12.

Ohkawara, B., Glinka, A. and Niehrs, C. (2011). Rspo3 binds syndecan 4 and induces Wnt/PCP signaling via clathrin-mediated endocytosis to promote morphogenesis. Dev Cell 20, 303-14.

Park, I. H., Arora, N., Huo, H., Maherali, N., Ahfeldt, T., Shimamura, A., Lensch, M. W., Cowan, C., Hochedlinger, K. and Daley, G. Q. (2008a). Disease-specific induced pluripotent stem cells. Cell 134, 877-86.

Park, I. H., Zhao, R., West, J. A., Yabuuchi, A., Huo, H., Ince, T. A., Lerou, P. H., Lensch, M. W. and Daley, G. Q. (2008b). Reprogramming of human somatic cells to pluripotency with defined factors. Nature 451, 141-6.

Pourquié O, Fan C M, Coltey M, Hirsinger E, Watanabe Y, Bréant C, Francis-West P, Brickell P, Tessier-Lavigne M, Le Douarin N M. Lateral and axial signals involved in avian somite patterning: a role for BMP4. Cell. 1996 Feb. 9; 84(3):461-71.

Prelle, K., Wobus, A. M., Krebs, O., Blum, W. F. and Wolf, E. (2000). Overexpression of insulin-like growth factor-II in mouse embryonic stem cells promotes myogenic differentiation. Biochem Biophys Res Commun 277, 631-8.

Reshef R, Maroto M, Lassar A B. Regulation of dorsal somitic cell fates: BMPs and Noggin control the timing and pattern of myogenic regulator expression. Genes Dev. 1998 Feb. 1; 12(3):290-303.

Ring, D. B., Johnson, K. W., Henriksen, E. J., Nuss, J. M., Goff, D., Kinnick, T. R., Ma, S. T., Reeder, J. W., Samuels, I., Slabiak, T. et al. (2003). Selective glycogen synthase kinase 3 inhibitors potentiate insulin activation of glucose transport and utilization in vitro and in vivo. Diabetes 52, 588-95.

Rohwedel, J., Maltsev, V., Bober, E., Arnold, H. H., Hescheler, J. and Wobus, A. M. (1994). Muscle cell differentiation of embryonic stem cells reflects myogenesis in vivo: developmentally regulated expression of myogenic determination genes and functional expression of ionic currents. Dev Biol 164, 87-101.

Sakurai, H., Inami, Y., Tamamura, Y., Yoshikai, T., Sehara-Fujisawa, A. and Isobe, K. (2009). Bidirectional induction toward paraxial mesodermal derivatives from mouse ES cells in chemically defined medium. Stem Cell Res 3, 157-69.

Sakurai, H., Okawa, Y., Inami, Y., Nishio, N. and Isobe, K. (2008). Paraxial mesodermal progenitors derived from mouse embryonic stem cells contribute to muscle regeneration via differentiation into muscle satellite cells. Stem Cells 26, 1865-73.

Sakurai H, Era T, Jakt L M, Okada M, Nakai S, Nishikawa S, Nishikawa S. In vitro modeling of paraxial and lateral mesoderm differentiation reveals early reversibility. Stem Cells. 2006 March; 24(3):575-86. Epub 2005 Dec. 9.

Sato, N., Meijer, L., Skaltsounis, L., Greengard, P. and Brivanlou, A. H. (2004). Maintenance of pluripotency in human and mouse embryonic stem cells through activation of Wnt signaling by a pharmacological GSK-3-specific inhibitor. Nat Med 10, 55-63.

Schlessinger, K., Hall, A. and Tolwinski, N. (2009). Wnt signaling pathways meet Rho GTPases. Genes Dev 23, 265-77.

Scott I C, Steiglitz B M, Clark T G, Pappano W N, Greenspan D S. Spatiotemporal expression patterns of mammalian chordin during postgastrulation embryogenesis and in postnatal brain. Dev Dyn. 2000 April; 217(4): 449-56.

Shani, M., Faerman, A., Emerson, C. P., Pearson-White, S., Dekel, I. and Magal, Y. (1992). The consequences of a constitutive expression of MyoD1 in ES cells and mouse embryos. Symp Soc Exp Biol 46, 19-36.

Skerjanc, I. S. (1999). Cardiac and skeletal muscle development in P19 embryonal carcinoma cells. Trends Cardiovasc Med 9, 139-43.

Stafford D A, Brunet L J, Khokha M K, Economides A N, Harland R M. Cooperative activity of noggin and gremlin 1 in axial skeleton development. Development. 2011 March; 138(5):1005-14.

Taelman, V. F., Dobrowolski, R., Plouhinec, J. L., Fuentealba, L. C., Vorwald, P. P., Gumper, I., Sabatini, D. D. and De Robertis, E. M. (2010). Wnt signaling requires sequestration of glycogen synthase kinase 3 inside multivesicular endosomes. Cell 143, 1136-48.

Takahashi, K., Tanabe, K., Ohnuki, M., Narita, M., Ichisaka, T., Tomoda, K. and Yamanaka, S. (2007). Induction of pluripotent stem cells from adult human fibroblasts by defined factors. Cell 131, 861-72.

Takahashi, K. and Yamanaka, S. (2006). Induction of pluripotent stem cells from mouse embryonic and adult fibroblast cultures by defined factors. Cell 126, 663-76.

Takebe A, Era T, Okada M, Martin Jakt L, Kuroda Y, Nishikawa S. Microarray analysis of PDGFR alpha+ populations in ES cell differentiation culture identifies genes involved in differentiation of mesoderm and mesenchyme including ARID3b that is essential for development of embryonic mesenchymal cells. Dev Biol. 2006 May 1; 293(1):25-37. Epub 2006 Mar. 13.

Tonegawa A, Funayama N, Ueno N, Takahashi Y. Mesodermal subdivision along the mediolateral axis in chicken controlled by different concentrations of BMP-4. Development. 1997 May; 124(10):1975-84.

Wijgerde M, Karp S, McMahon J, McMahon A P. Noggin antagonism of BMP4 signaling controls development of the axial skeleton in the mouse. Dev Biol. 2005 Oct. 1; 286(1):149-57.

Wittler, L., Shin, E. H., Grote, P., Kispert, A., Beckers, A., Gossler, A., Werber, M. and Herrmann, B. G. (2007). Expression of Msgn1 in the presomitic mesoderm is controlled by synergism of WNT signaling and Tbx6. EMBO Rep 8, 784-9.

Wu, D. and Pan, W. (2010). GSK3: a multifaceted kinase in Wnt signaling. Trends Biochem Sci 35, 161-8.

Yoon, J. K. and Wold, B. (2000). The bHLH regulator pMesogenin1 is required for maturation and segmentation of paraxial mesoderm. Genes Dev 14, 3204-14.

Yu, J., Vodyanik, M. A., Smuga-Otto, K., Antosiewicz-Bourget, J., Frane, J. L., Tian, S., Nie, J., Jonsdottir, G. A., Ruotti, V., Stewart, R. et al. (2007). Induced pluripotent stem cell lines derived from human somatic cells. Science 318, 1917-20.

Yu P B, Hong C C, Sachidanandan C, Babitt J L, Deng D Y, Hoyng S A, Lin H Y, Bloch K D, Peterson R T. Dorsomorphin inhibits BMP signals required for embryogenesis and iron metabolism. Nat Chem. Biol. 2008 January; 4(1):33-41. Epub 2007 Nov. 18.

The invention claimed is:

1. An ex vivo method for preparing a cell population comprising induced human paraxial mesoderm progenitor (iPAM) cells, the method comprising:

culturing human pluripotent cells in a basal culture medium comprising an effective amount of a R-spondin protein or a GSK-3β inhibitor, wherein the culturing results in the production of a human cell population comprising iPAM cells expressing Msgn1 and Tbx6.

2. An ex vivo method for preparing a cell population comprising induced human paraxial mesoderm progenitor (iPAM) cells, the method comprising:

culturing human pluripotent cells selected from the group consisting of human embryonic stem cells or human induced pluripotent stem (iPS) cells, in a basal culture medium comprising an effective amount of a BMP4 inhibitor, and an effective amount of a R-spondin protein or a GSK-3β inhibitor, wherein the culturing results in the production of a human cell population comprising iPAM cells expressing Msgn1 and Tbx6.

3. The ex vivo method according to claim 1, wherein the R-spondin protein is selected from the group consisting of R-spondin 3, R-spondin 2, and a combination of R-spondin 3 and R-spondin 2.

4. The ex vivo method according to claim 3, wherein the R-spondin 3 protein is human R-spondin 3 protein encoded by SEQ ID NO: 1, or human R-spondin 3 isoform 2 protein, encoded by SEQ ID NO: 5.

5. The ex vivo method according to claim 3, wherein the R-spondin 2 protein is human R-spondin 2 encoded by SEQ ID NO: 3, human R-spondin 2 isoform 2, encoded by SEQ ID NO: 6, or human R-spondin 2 isoform 3, encoded by SEQ ID NO: 7.

6. The ex vivo method according to claim 2, wherein the BMP4 inhibitor is a protein selected from the group consisting of Noggin, Follistatin and Dorsomorphin.

7. The ex vivo method according to claim 6, wherein the BMP4 inhibitor is Noggin.

8. The ex vivo method according to claim 2, wherein the BMP4 inhibitor is a chemical inhibitor.

9. The ex vivo method according to claim 1, wherein the culture medium further comprises DMSO.

10. The ex vivo method according to claim 2, wherein the basal culture medium further comprises DMSO.

11. The ex vivo method according to claim 1, wherein the GSK-3β inhibitor is a chemical inhibitor.

12. The ex vivo method according to claim 11, wherein the GSK-3β inhibitor is CHIR99021 or LiCl.

13. The ex vivo method according to claim 2, wherein the GSK-3β inhibitor is a chemical inhibitor.

14. The ex vivo method according to claim 13, wherein the GSK-3β inhibitor is CHIR99021 or LiCl.

15. The ex vivo method according to claim 1, wherein the basal culture medium further comprises serum or a serum substitute.

16. The ex vivo method according to claim 2, wherein the basal culture medium further comprises serum or a serum substitute.

* * * * *

SEQUENCE LISTING

<160> NUMBER OF SEQ ID NOS: 11

<210> SEQ ID NO 1
<211> LENGTH: 272
<212> TYPE: PRT
<213> ORGANISM: Homo sapiens

<400> SEQUENCE: 1

Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Gly Cys Ala Thr Cys
                35                  40                  45

Ser Asp Tyr Asn Gly Cys Leu Ser Cys Lys Pro Arg Leu Phe Phe Ala
        50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
            115                 120                 125

Cys Pro Glu Gly Leu Glu Ala Asn Asn His Thr Met Glu Cys Val Ser
        130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Lys Gly Arg Glu Arg Lys Arg Lys Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser Val Ser Val Ser Thr Val His
            260                 265                 270

<210> SEQ ID NO 2
<211> LENGTH: 277
<212> TYPE: PRT
<213> ORGANISM: Mus musculus

<400> SEQUENCE: 2

Met His Leu Arg Leu Ile Ser Cys Phe Phe Ile Ile Leu Asn Phe Met
1               5                   10                  15

Glu Tyr Ile Gly Ser Gln Asn Ala Ser Arg Gly Arg Gln Arg Arg
            20                  25                  30

Met His Pro Asn Val Ser Gln Gly Cys Gln Gly Gly Cys Ala Thr Cys
                35                  40                  45

Ser Asp Tyr Asn Gly Cys Leu Ser Cys Lys Pro Arg Leu Phe Phe Val

```
Leu Glu Arg Ile Gly Met Lys Gln Ile Gly Val Cys Leu Ser Ser Cys
 65                  70                  75                  80

Pro Ser Gly Tyr Tyr Gly Thr Arg Tyr Pro Asp Ile Asn Lys Cys Thr
                 85                  90                  95

Lys Cys Lys Val Asp Cys Asp Thr Cys Phe Asn Lys Asn Phe Cys Thr
                100                 105                 110

Lys Cys Lys Ser Gly Phe Tyr Leu His Leu Gly Lys Cys Leu Asp Ser
                115                 120                 125

Cys Pro Glu Gly Leu Glu Ala Asn Asn His Thr Met Glu Cys Val Ser
        130                 135                 140

Ile Val His Cys Glu Ala Ser Glu Trp Ser Pro Trp Ser Pro Cys Met
145                 150                 155                 160

Lys Lys Gly Lys Thr Cys Gly Phe Lys Arg Gly Thr Glu Thr Arg Val
                165                 170                 175

Arg Asp Ile Leu Gln His Pro Ser Ala Lys Gly Asn Leu Cys Pro Pro
            180                 185                 190

Thr Ser Glu Thr Arg Thr Cys Ile Val Gln Arg Lys Lys Cys Ser Lys
        195                 200                 205

Gly Glu Arg Gly Lys Lys Gly Arg Glu Arg Lys Arg Lys Lys Leu Asn
        210                 215                 220

Lys Glu Glu Arg Lys Glu Thr Ser Ser Ser Asp Ser Lys Gly Leu
225                 230                 235                 240

Glu Ser Ser Ile Glu Thr Pro Asp Gln Glu Asn Lys Glu Arg Gln
                245                 250                 255

Gln Gln Gln Lys Arg Arg Ala Arg Asp Lys Gln Gln Lys Ser Val Ser
            260                 265                 270

Val Ser Thr Val His
            275

<210> SEQ ID NO 3
<211> LENGTH: 243
<212> TYPE: PRT
<213> ORGANISM: Homo sapiens

<400> SEQUENCE: 3

Met Gln Phe Arg Leu Phe Ser Phe Ala Leu Ile Ile Leu Asn Cys Met
 1               5                  10                  15

Asp Tyr Ser His Cys Gln Gly Asn Arg Trp Arg Arg Ser Lys Arg Ala
                20                  25                  30

Ser Tyr Val Ser Asn Pro Ile Cys Lys Gly Cys Leu Ser Cys Ser Lys
             35                  40                  45

Asp Asn Gly Cys Ser Arg Cys Gln Gln Lys Leu Phe Phe Phe Leu Arg
        50                  55                  60

Arg Glu Gly Met Arg Gln Tyr Gly Glu Cys Leu His Ser Cys Pro Ser
 65                  70                  75                  80

Gly Tyr Tyr Gly His Arg Ala Pro Asp Met Asn Arg Cys Ala Arg Cys
                 85                  90                  95

Arg Ile Glu Asn Cys Asp Ser Cys Phe Ser Lys Asp Phe Cys Thr Lys
                100                 105                 110

Cys Lys Val Gly Phe Tyr Leu His Arg Gly Arg Cys Phe Asp Glu Cys
                115                 120                 125

Pro Asp Gly Phe Ala Pro Leu Glu Glu Thr Met Glu Cys Val Glu Gly
        130                 135                 140
```

```
Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
            165                 170                 175

Val Lys Lys Pro Val Lys Asp Thr Ile Leu Cys Pro Thr Ile Ala Glu
            180                 185                 190

Ser Arg Arg Cys Lys Met Thr Met Arg His Cys Pro Gly Gly Lys Arg
            195                 200                 205

Thr Pro Lys Ala Lys Glu Lys Arg Asn Lys Lys Lys Arg Lys Leu
210                 215                 220

Ile Glu Arg Ala Gln Glu Gln His Ser Val Phe Leu Ala Thr Asp Arg
225                 230                 235                 240

Ala Asn Gln

<210> SEQ ID NO 4
<211> LENGTH: 243
<212> TYPE: PRT
<213> ORGANISM: Mus musculus

<400> SEQUENCE: 4

Met Arg Phe Cys Leu Phe Ser Phe Ala Leu Ile Ile Leu Asn Cys Met
1               5                   10                  15

Asp Tyr Ser Gln Cys Gln Gly Asn Arg Trp Arg Asn Lys Arg Ala
            20                  25                  30

Ser Tyr Val Ser Asn Pro Ile Cys Lys Gly Cys Leu Ser Cys Ser Lys
            35                  40                  45

Asp Asn Gly Cys Ser Arg Cys Gln Gln Lys Leu Phe Phe Phe Leu Arg
50                  55                  60

Arg Glu Gly Met Arg Gln Tyr Gly Glu Cys Leu His Ser Cys Pro Ser
65                  70                  75                  80

Gly Tyr Tyr Gly His Arg Ala Pro Asp Met Asn Arg Cys Ala Arg Cys
                85                  90                  95

Arg Ile Glu Asn Cys Asp Ser Cys Phe Ser Lys Asp Phe Cys Thr Lys
            100                 105                 110

Cys Lys Val Gly Phe Tyr Leu His Arg Gly Arg Cys Phe Asp Glu Cys
            115                 120                 125

Pro Asp Gly Phe Ala Pro Leu Asp Glu Thr Met Glu Cys Val Glu Gly
130                 135                 140

Cys Glu Val Gly His Trp Ser Glu Trp Gly Thr Cys Ser Arg Asn Asn
145                 150                 155                 160

Arg Thr Cys Gly Phe Lys Trp Gly Leu Glu Thr Arg Thr Arg Gln Ile
            165                 170                 175

Val Lys Lys Pro Ala Lys Asp Thr Ile Pro Cys Pro Thr Ile Ala Glu
            180                 185                 190

Ser Arg Arg Cys Lys Met Ala Met Arg His Cys Pro Gly Gly Lys Arg
            195                 200                 205

Thr Pro Lys Ala Lys Glu Lys Arg Asn Lys Lys Lys Arg Arg Lys Leu
210                 215                 220

Ile Glu Arg Ala Gln Glu Gln His Ser Val Phe Leu Ala Thr Asp Arg
225                 230                 235                 240

Val Asn Gln

<210> SEQ ID NO 5
<211> LENGTH: 292
<212> TYPE: PRT
```

<213> ORGANISM: Homo sapiens

<400> SEQUENCE: 5

```
Met His Leu Arg Leu Ile Ser Trp Leu Phe Ile Ile Leu Asn Phe Met
1               5                   10                  15

Glu Tyr Ile Gly Ser Gln Asn Ala Ser Arg Gly Arg Arg Gln Arg Arg
            20                  25                  30

Met His Pro Asn Val Ser Gln Gly Cys Gln Gly Gly Cys Ala Thr Cys
        35                  40                  45

Ser Asp Tyr Asn Gly Cys Leu Ser Cys Lys Pro Arg Leu Phe Phe Ala
    50                  55                  60

Leu Glu Arg Ile Gly Met Lys Gln Ile Gly Val Cys Leu Ser Ser Cys
65                  70                  75                  80

Pro Ser Gly Tyr Tyr Gly Thr Arg Tyr Pro Asp Ile Asn Lys Cys Thr
                85                  90                  95

Lys Cys Lys Ala Asp Cys Asp Thr Cys Phe Asn Lys Asn Phe Cys Thr
            100                 105                 110

Lys Cys Lys Ser Gly Phe Tyr Leu His Leu Gly Lys Cys Leu Asp Asn
        115                 120                 125

Cys Pro Glu Gly Leu Glu Ala Asn Asn His Thr Met Glu Cys Val Ser
    130                 135                 140

Ile Val His Cys Glu Val Ser Glu Trp Asn Pro Trp Ser Pro Cys Thr
145                 150                 155                 160

Lys Lys Gly Lys Thr Cys Gly Phe Lys Arg Gly Thr Glu Thr Arg Val
                165                 170                 175

Arg Glu Ile Ile Gln His Pro Ser Ala Lys Gly Asn Leu Cys Pro Pro
            180                 185                 190

Thr Asn Glu Thr Arg Lys Cys Thr Val Gln Arg Lys Lys Cys Gln Lys
        195                 200                 205

Gly Glu Arg Gly Lys Lys Gly Arg Glu Arg Lys Arg Lys Lys Pro Asn
    210                 215                 220

Lys Gly Glu Ser Lys Glu Ala Ile Pro Asp Ser Lys Ser Leu Glu Ser
225                 230                 235                 240

Ser Lys Glu Ile Pro Glu Gln Arg Glu Asn Lys Gln Gln Gln Lys Lys
                245                 250                 255

Arg Lys Val Gln Asp Lys Gln Lys Ser Gly Ile Glu Val Thr Leu Ala
            260                 265                 270

Glu Gly Leu Thr Ser Val Ser Gln Arg Thr Gln Pro Thr Pro Cys Arg
        275                 280                 285

Arg Arg Tyr Leu
    290
```

<210> SEQ ID NO 6
<211> LENGTH: 176
<212> TYPE: PRT
<213> ORGANISM: Homo sapiens

<400> SEQUENCE: 6

```
Met Arg Gln Tyr Gly Glu Cys Leu His Ser Cys Pro Ser Gly Tyr Tyr
1               5                   10                  15

Gly His Arg Ala Pro Asp Met Asn Arg Cys Ala Arg Cys Arg Ile Glu
            20                  25                  30

Asn Cys Asp Ser Cys Phe Ser Lys Asp Phe Cys Thr Lys Cys Lys Val
        35                  40                  45

Gly Phe Tyr Leu His Arg Gly Arg Cys Phe Asp Glu Cys Pro Asp Gly
```

```
                50              55              60
Phe Ala Pro Leu Glu Glu Thr Met Glu Cys Val Gly Cys Glu Val
 65                  70                  75                  80

Gly His Trp Ser Glu Trp Gly Thr Cys Ser Arg Asn Asn Arg Thr Cys
                 85                  90                  95

Gly Phe Lys Trp Gly Leu Glu Thr Arg Thr Arg Gln Ile Val Lys Lys
                100                 105                 110

Pro Val Lys Asp Thr Ile Leu Cys Pro Thr Ile Ala Glu Ser Arg Arg
            115                 120                 125

Cys Lys Met Thr Met Arg His Cys Pro Gly Gly Lys Arg Thr Pro Lys
130                 135                 140

Ala Lys Glu Lys Arg Asn Lys Lys Lys Arg Lys Leu Ile Glu Arg
145                 150                 155                 160

Ala Gln Glu Gln His Ser Val Phe Leu Ala Thr Asp Arg Ala Asn Gln
                165                 170                 175
```

```
<210> SEQ ID NO 7
<211> LENGTH: 177
<212> TYPE: PRT
<213> ORGANISM: Homo sapiens

<400> SEQUENCE: 7
```

```
Phe Arg Leu Phe Ser Phe Ala Leu Ile Ile Leu Asn Cys Met Asp Tyr
 1               5                  10                  15

Ser His Cys Gln Gly Asn Arg Trp Arg Ser Lys Arg Gly Cys Arg
                 20                  25                  30

Ile Glu Asn Cys Asp Ser Cys Phe Ser Lys Asp Phe Cys Thr Lys Cys
             35                  40                  45

Lys Val Gly Phe Tyr Leu His Arg Gly Arg Cys Phe Asp Glu Cys Pro
 50                  55                  60

Asp Gly Phe Ala Pro Leu Glu Glu Thr Met Glu Cys Val Gly Cys Glu
 65                  70                  75                  80

Val Gly His Trp Ser Glu Trp Gly Thr Cys Ser Arg Asn Asn Arg Thr
                 85                  90                  95

Cys Gly Phe Lys Trp Gly Leu Glu Thr Arg Thr Arg Gln Ile Val Lys
                100                 105                 110

Lys Pro Val Lys Asp Thr Ile Leu Cys Pro Thr Ile Ala Glu Ser Arg
            115                 120                 125

Arg Cys Lys Met Thr Met Arg His Cys Pro Gly Gly Lys Arg Thr Pro
130                 135                 140

Lys Ala Lys Glu Lys Arg Asn Lys Lys Lys Arg Lys Leu Ile Glu
145                 150                 155                 160

Arg Ala Gln Glu Gln His Ser Val Phe Leu Ala Thr Asp Arg Ala Asn
                165                 170                 175

Gln
```

```
<210> SEQ ID NO 8
<211> LENGTH: 567
<212> TYPE: DNA
<213> ORGANISM: Mus musculus

<400> SEQUENCE: 8
atggacaacc tgggtgagac cttcctcagc ctggaggatg gcctggactc ttctgacacc    60
gctggtctgc tggcctcctg ggactggaaa agcagagcca ggcccttgga gctggtccag   120
gagtccccca ctcaaaagcct ctccccagct ccttctctgg agtcctactc tgaggtcgca   180
```

```
ctgccctgcg ggcacagtgg ggccagcaca ggaggcagcg atggctacgg cagtcacgag      240
gctgccggct tagtcgagct ggattacagc atgttggctt ttcaacctcc ctatctacac      300
actgctggtg gcctcaaagg ccagaaaggc agcaaagtca agatgtctgt ccagcggaga      360
cggaaggcca gcgagagaga gaaactcagg atgcggacct tagccgatgc cctccacacg      420
ctccggaatt acctgccgcc tgtctacagc agagaggcc aaccgctcac caagatccag       480
acactcaagt acaccatcaa gtacatcggg gaactcacag acctcctcaa cagcagcggg      540
agagagccca ggccacagag tgtgtga                                          567
```

```
<210> SEQ ID NO 9
<211> LENGTH: 582
<212> TYPE: DNA
<213> ORGANISM: Homo sapiens

<400> SEQUENCE: 9
```

```
atggacaacc tgcgcgagac tttcctcagc ctcgaggatg gcttgggctc ctctgacagc       60
cctggcctgc tgtcttcctg ggactggaag acagggcag ggcccttga gctgaatcag       120 gcctccccct ctcagagcct ttccccggct ccatcgctgg aatcctattc ttcttctccc      180
tgtccagctg tggctgggct gccctgtgag cacggcgggg ccagcagtgg gggcagcgaa      240
ggctgcagtg tcggtggggc cagtggcctg tagaggtgg actacaatat gttagctttc      300
cagcccaccc accttcaggg cggtggtggc cccaaggccc agaagggcac caaagtcagg      360
atgtctgtcc agcggaggcg gaaagccagc gagagggaga agctcaggat gaggaccttg      420
gcagatgccc tgcacaccct ccggaattac ctgccacctg tctacagcca gagaggccag      480
cctctcacca agatccagac actcaagtac accatcaagt acatcgggga actcacagac      540
ctccttaacc gcggcagaga gcccagagcc agagcgcgt ga                          582
```

```
<210> SEQ ID NO 10
<211> LENGTH: 232
<212> TYPE: PRT
<213> ORGANISM: Mus musculus

<400> SEQUENCE: 10
```

Met Glu Arg Cys Pro Ser Leu Gly Val Thr Leu Tyr Ala Leu Val Val
1               5                   10                  15

Val Leu Gly Leu Arg Ala Ala Pro Ala Gly Gly Gln His Tyr Leu His
                20                  25                  30

Ile Arg Pro Ala Pro Ser Asp Asn Leu Pro Leu Val Asp Leu Ile Glu
            35                  40                  45

His Pro Asp Pro Ile Phe Asp Pro Lys Glu Lys Asp Leu Asn Glu Thr
        50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Pro Ala Gly
                85                  90                  95

Gly Ala Glu Asp Leu Ala Glu Leu Asp Gln Leu Leu Arg Gln Arg Pro
            100                 105                 110

Ser Gly Ala Met Pro Ser Glu Ile Lys Gly Leu Glu Phe Ser Glu Gly
        115                 120                 125

Leu Ala Gln Gly Lys Lys Gln Arg Leu Ser Lys Leu Arg Arg Lys
130                 135                 140

Leu Gln Met Trp Leu Trp Ser Gln Thr Phe Cys Pro Val Leu Tyr Ala

```
                        145                 150                 155                 160
Trp Asn Asp Leu Gly Ser Arg Phe Trp Pro Arg Tyr Val Lys Val Gly
                    165                 170                 175

Ser Cys Phe Ser Lys Arg Ser Cys Ser Val Pro Glu Gly Met Val Cys
                    180                 185                 190

Lys Pro Ser Lys Ser Val His Leu Thr Val Leu Arg Trp Arg Cys Gln
                    195                 200                 205

Arg Arg Gly Gly Gln Arg Cys Gly Trp Ile Pro Ile Gln Tyr Pro Ile
                    210                 215                 220

Ile Ser Glu Cys Lys Cys Ser Cys
225                 230

<210> SEQ ID NO 11
<211> LENGTH: 232
<212> TYPE: PRT
<213> ORGANISM: Homo sapiens

<400> SEQUENCE: 11

Met Glu Arg Cys Pro Ser Leu Gly Val Thr Leu Tyr Ala Leu Val Val
1               5                   10                  15

Val Leu Gly Leu Arg Ala Thr Pro Ala Gly Gly Gln His Tyr Leu His
                20                  25                  30

Ile Arg Pro Ala Pro Ser Asp Asn Leu Pro Leu Val Asp Leu Ile Glu
                35                  40                  45

His Pro Asp Pro Ile Phe Asp Pro Lys Glu Lys Asp Leu Asn Glu Thr
            50                  55                  60

Leu Leu Arg Ser Leu Leu Gly Gly His Tyr Asp Pro Gly Phe Met Ala
65                  70                  75                  80

Thr Ser Pro Pro Glu Asp Arg Pro Gly Gly Gly Gly Ala Ala Gly
                    85                  90                  95

Gly Ala Glu Asp Leu Ala Glu Leu Asp Gln Leu Leu Arg Gln Arg Pro
                100                 105                 110

Ser Gly Ala Met Pro Ser Glu Ile Lys Gly Leu Glu Phe Ser Glu Gly
                115                 120                 125

Leu Ala Gln Gly Lys Lys Gln Arg Leu Ser Lys Lys Leu Arg Arg Lys
                130                 135                 140

Leu Gln Met Trp Leu Trp Ser Gln Thr Phe Cys Pro Val Leu Tyr Ala
145                 150                 155                 160

Trp Asn Asp Leu Gly Ser Arg Phe Trp Pro Arg Tyr Val Lys Val Gly
                    165                 170                 175

Ser Cys Phe Ser Lys Arg Ser Cys Ser Val Pro Glu Gly Met Val Cys
                    180                 185                 190

Lys Pro Ser Lys Ser Val His Leu Thr Val Leu Arg Trp Arg Cys Gln
                    195                 200                 205

Arg Arg Gly Gly Gln Arg Cys Gly Trp Ile Pro Ile Gln Tyr Pro Ile
                    210                 215                 220

Ile Ser Glu Cys Lys Cys Ser Cys
225                 230
```